United States Patent
Bernard et al.

(10) Patent No.: US 9,815,888 B2
(45) Date of Patent: Nov. 14, 2017

(54) THERAPEUTIC USE OF SPECIFIC LIGAND IN MSRV ASSOCIATED DISEASES

(71) Applicant: GENEURO SA, Plan-les-Ouates (CH)

(72) Inventors: Corinne Bernard, Saint Julien en Genevois (FR); Alois Bernhardt Lang, Bern (CH); Herve Perron, Saint Genis les Ollieres (FR); Jean-Baptiste Bertrand, Lyons (FR)

(73) Assignee: GENEURO SA, Plan-les-Ouates (CH)

( * ) Notice: Subject to any disclaimer, the term of this patent is extended or adjusted under 35 U.S.C. 154(b) by 0 days.

(21) Appl. No.: 15/367,864

(22) Filed: Dec. 2, 2016

(65) Prior Publication Data

US 2017/0107274 A1    Apr. 20, 2017

Related U.S. Application Data

(62) Division of application No. 14/221,963, filed on Mar. 21, 2014, now Pat. No. 9,550,824, which is a division of application No. 12/997,486, filed as application No. PCT/EP2009/058663 on Jul. 8, 2009, now Pat. No. 8,715,656.

(60) Provisional application No. 61/213,189, filed on May 15, 2009, provisional application No. 61/202,581, filed on Mar. 13, 2009, provisional application No. 61/129,613, filed on Jul. 8, 2008.

(51) Int. Cl.
*A61K 39/395*     (2006.01)
*C07K 16/10*     (2006.01)
*A61K 39/00*     (2006.01)

(52) U.S. Cl.
CPC .... *C07K 16/1036* (2013.01); *A61K 2039/505* (2013.01); *C07K 2317/24* (2013.01); *C07K 2317/56* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | |
|---|---|---|
| 2003/0185827 A1 | 10/2003 | Rodriguez et al. |
| 2007/0141054 A1 | 6/2007 | Kataoka et al. |
| 2007/0190599 A1 | 8/2007 | Nakano et al. |
| 2008/0038279 A1 | 2/2008 | Marche et al. |
| 2009/0110682 A1 | 4/2009 | Yanagisawa et al. |

FOREIGN PATENT DOCUMENTS

| | | |
|---|---|---|
| EP | 1 829 962 A1 | 9/2007 |
| WO | 01/31021 A1 | 5/2001 |
| WO | 2004/106383 A1 | 12/2004 |
| WO | 2005/080437 A1 | 9/2005 |
| WO | 2006006693 A1 | 1/2006 |
| WO | 2006028197 A1 | 3/2006 |
| WO | 2006137354 A1 | 12/2006 |
| WO | 2006138627 A2 | 12/2006 |
| WO | 2008/113916 A2 | 9/2008 |

OTHER PUBLICATIONS

Dolei. MSRV/HERV-W/syncytin and its linkage to multiple sclerosis: the usability and the hazard of a human endogenous retrovirus. J Neurovirol. Apr. 2005;11 (2):232-5. Review.
Gohil. Multiple Sclerosis: Progress, but No Cure. PT. Sep. 2015;40(9):604-5.
Perron et al., "Monoclonal antibody against envelope protein from Human Endogenous Retrovirus "W" (MSRV-ENV or Syncytin) inhibits TLR4-initated immunotoxicity cascade in human peripheral blood mononuclear cells and displays therapeutic effects in novel pre-clinical models for Multiple Sclerosis," 8th International Symposium on NeuroVirology, 2007, pp. 112-113.
Blond et al., "An Envelope Glycoprotein of the Human Endogenous Retrovirus HERV-W Is Expressed in the Human Placenta and Fuses Cells Expressing the Type D Mammalian Retrovirus Receptor," Journal of Virology, 2000, vol. 74, No. 7, pp. 3321-3329.
Lang et al., "The therapeutic potential of monoclonal anti-human endogenous retrovirus W (HERV-W) envelope protein antibody in multiple sclerosis: Results from a new EAE-animal model," Human Antibodies, 2008, vol. 17, p. 21.
Perron et al., "Endogenous retroviral genes, Herpesviruses and gender in Multiple Sclerosis," Journal of the Neurological Sciences, 2009, vol. 286, pp. 65-72.
Nov. 9, 2009 International Search Report issued in International Patent Application No. PCT/EP2009/058663.
Jan. 11, 2011 International Preliminary Report on Patentability issued in International Patent Application No. PCT/EP2009/058663.
GenBank: BG148606.1, Feb. 1, 2001, "uu84f12.y1 Soares_mouse_NMGB_bcell Mus musculus cDNA clone Image: 3383207 5-similar to SW:KV6K_MOUSE P04945 IG Kappa Chain V-VI Region NG2-6.1;, mRNA sequence".
Hinton et al., An engineered human IgG1 antibody with longer serum half-life, J Immunol. Jan. 1, 2006; 76 (1):346-56.
Jan. 7, 2016 Office Action issued in U.S. Appl. No. 14/221,963.
Sep. 2, 2016 Notice of Allowance issued in U.S. Appl. No. 14/221,963.

*Primary Examiner* — Michelle S Horning
(74) *Attorney, Agent, or Firm* — Oliff PLC

(57) ABSTRACT

A ligand includes each of the complementary-determining regions (CDRs) set forth in SEQ ID No. 1, SEQ ID No. 2, SEQ ID No. 3 SEQ ID No. 4, SEQ ID No. 5 and SEQ ID No. 6 or any sequence having either number of substituted aminoacids within said sequences as indicated in the following, from 0 to 3 in CDR1 (SEQ ID No.1), from 0 to 2 in CDR2 (SEQ ID No.2), from 0 to 2 in CDR3 (SEQ ID No.3), from 0 to 1 in CDR4 (SEQ ID No.4), from 0 to 4 in CDR5 (SEQ ID No.5), from 0 to 2 in CDR6 (SEQ ID No.6), or aminoacids substituted with other aminoacids having equivalent chemical functions and properties, within said sequences SEQ ID No. 1 to SEQ ID No. 6.

14 Claims, 33 Drawing Sheets

(A)

Figure 2:
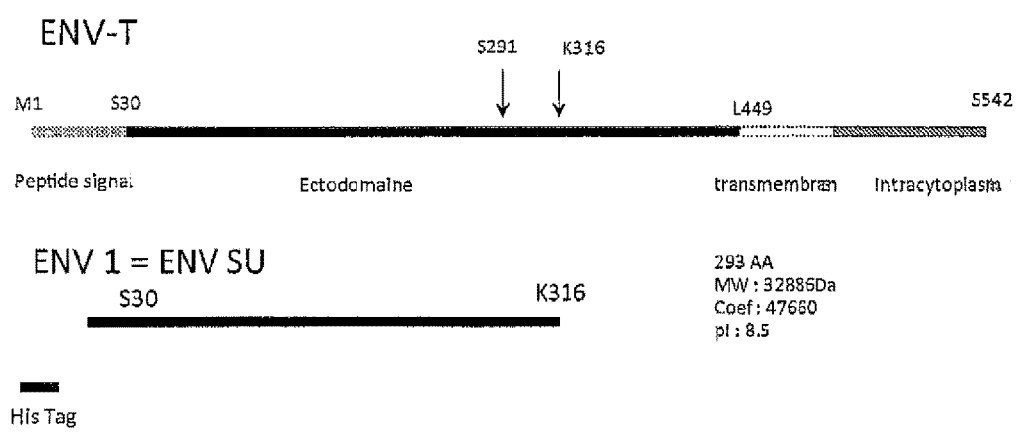

QIVLTQSPAIMSASPGEKVTISCSASSSVSYMYWYQQKPGSSPKAWIYRT
SNLASGVPGRFSGSGSGTSYSLTISSMEAEDAATYYCQQYQSLPLTFGSG
TKLEIK (SEQ ID NO: 7)

(B)

QVQLQQSGAELVRPGAPVTLSCKASGYTFTDYEMHWVKQTPVHGLEWIGA
VAPETGGTAYNQKFKGKATLTAAKSSSTAYMELRSLTSEDSAVYYCTSIV
VPFAYWGQGTLVTVSA (SEQ ID NO: 8)

FIGURE 1

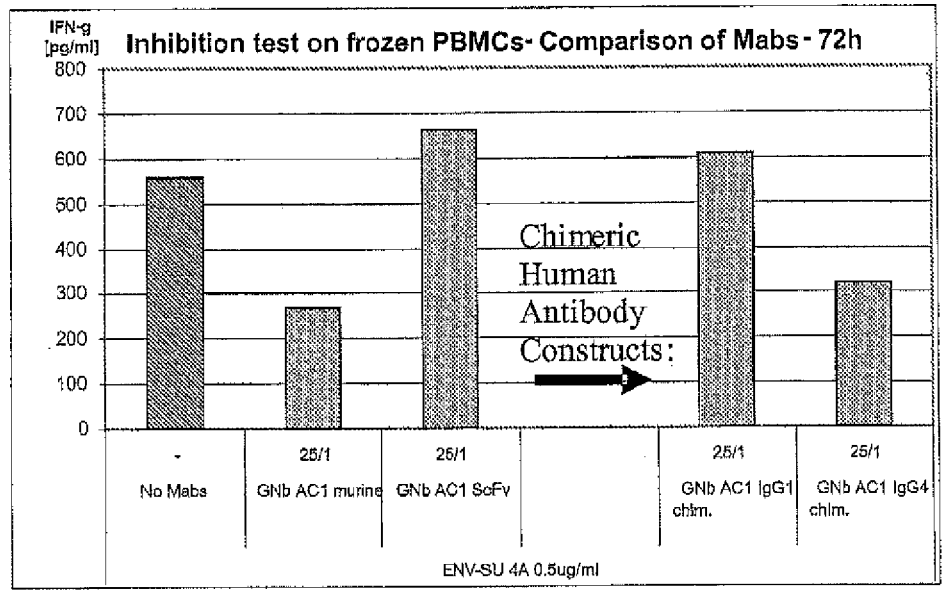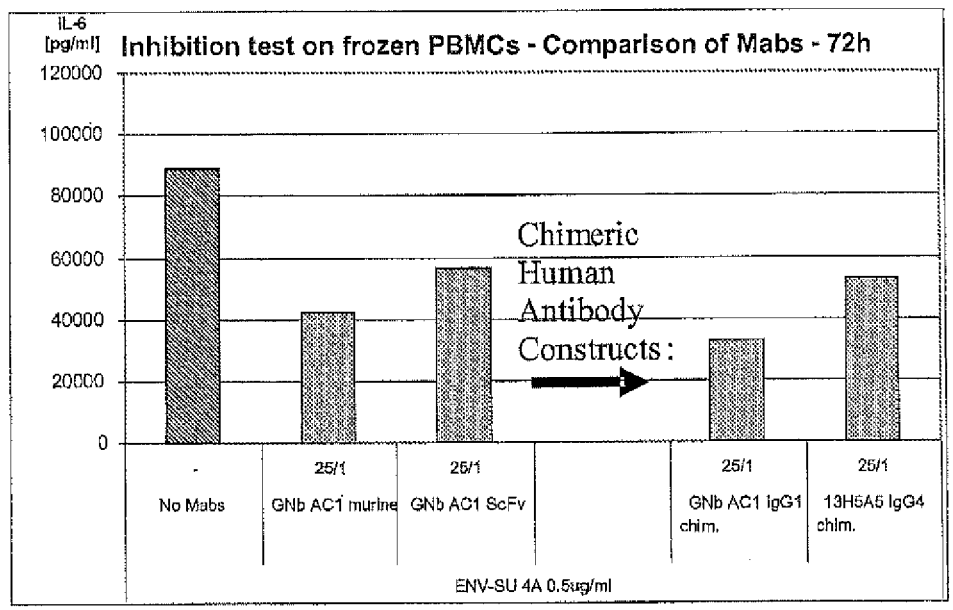
FIGURE 7

15A: Kabat and Chothia definitions:
QVQLQQSGAELVRPGASVTLSCKASGYTPT <u>DYEMH</u> WVKQTPVHGLEWIG
<u>AVAPETGGTAYWQKFKG</u>KATLTAAKSSSTAYMELRSLTSEDSAVYYCTS
<u>TVVPFAY</u> WGQGTLVTVSA (SEQ ID NOS: 33-35)

15B: Preferred (combined) Definition:
QVQLQQSGAELVRPGASVTLSCKAS <u>GYTPTDYEMH</u> WVKQTPVHGLEWIG
<u>AVAPETGGTAYWQKFKG</u>KATLTAAKSSSTAYMELRSLTSEDSAVYYCTS
<u>TVVPFAY</u> WGQGTLVTVSA (SEQ ID NOS: 33-35)

FIGURE 15

QIVLTQSPAIMSASPGEKVTISC<u>SASSSVSYMY</u>WYQQKPGSSPKAWIY<u>RTSNL
AS</u>GVPGRFSGSGSGTSYSLTISSMEAEDAATYYC<u>QQYQSLPLT</u>
FGSGTKLEIKR  (SEQ ID NOS: 36-38)

FIGURE 16

H2 Heavy chain :
QVQLVQSGAEVKKPGSSVKVSCKASGYTET<u>DYEMH</u>WVRQAPGQGLEW<sup>I</sup><u>GAVAPE</u>
<u>TGGTAYNQKFKGR</u><sup>A</sup>TITADKSTSTAYMELSSLRSEDTAVYYC<sup>TS</sup><u>TVVPFAY</u>WGQGT
LVTVSS (SEQ ID NO: 40)

VK3 Light chain :
<sup>Q</sup>IQ<sup>L</sup>TQSPSSLSASVGDRVTITC<u>SASSSVSYMY</u>WQQKPGKAPK<sup>AW</sup><u>IYRTSNLAS</u>GV
PSRFSGSGSGTD<sup>Y</sup>TLTISSLQPEDFATYYC<u>QQYQSLPLT</u>FGGGTKVEIK(SEQ ID NO: 48)

FIGURE 23

THERAPEUTIC USE OF SPECIFIC LIGAND IN MSRV ASSOCIATED DISEASES

This is a Division of application Ser. No. 14/221,963, filed Mar. 21, 2014, which is a Division of application Ser. No. 12/997,486, filed Mar. 22, 2011, which in turn is a National Stage of PCT/EP2009/058663, filed Jul. 8, 2009, which claims the benefit of U.S. Provisional Application Nos. 61/129,613 filed Jul. 8, 2008, 61/202,581 filed Mar. 13, 2009, and 61/213,189 filed May 15, 2009. The disclosures of the prior applications are hereby incorporated by reference herein in their entireties.

The object of the present invention is a ligand which displays significant binding to a target molecule, the anti-ligand.

According to the present invention, the "anti-ligand" is the MSRV-ENV (envelope) protein, MSRV for "Multiple Sclerosis associated retrovirus (Perron, et al. (1997). "Molecular identification of a novel retrovirus repeatedly isolated from patients with multiple sclerosis. The Collaborative Research Group on Multiple Sclerosis." Proc Natl Acad Sci USA 94(14): 7583-8.). "MSRV-ENV protein" shall be understood as the complete or partial protein product encoded by MSRV env genes as defined in Komurian-Pradel, F, et al. (1999). Virology 260(1): 1-9, and Rolland A, et al. (2006) J Immunol 176(12): 7636-44 or any molecule mimicking the antigenic or binding properties of MRSV-ENV (mimotope). <<ENV-T>> corresponds to the complete protein, which is detailed in example 2 (residues 1 to 542), and <<ENV-SU>> also named ENV-1 corresponds to S30 to K316 sequence as is detailed in example 2. Env-SU is also referred to in Rolland A, et al. (2006) J Immunol 176(12): 7636-44. As usual for retroviruses, MSRV, shows variability in its envelope protein—ENV—(Perron, H et al. (2000) J Neurovirol 6: S67-75; Voisset, C., O. Bouton, et al. (2000) AIDS Res Hum Retroviruses 16(8): 731-40). Mimotopes mimicking MSRV ENV partial protein fragments have been shown to exist and to be selectively bound by antibodies from patients with Multiple Sclerosis (Jolivet-Reynaud, C., H. Perron, et al. (1999). "Specificities of multiple sclerosis cerebrospinal fluid and serum antibodies against mimotopes." Clin Immunol 93(3): 283-93

More particularly, the ligand of the present invention comprises each of the complementary-determining regions (CDRs) having the amino acid sequences SEQ ID No. 1, SEQ ID No. 2, SEQ ID No. 3, SEQ ID No. 4, SEQ ID No. 5 and SEQ ID No. 6 or any sequence having either:

a number of substituted aminoacids within said sequences as indicated in the following, and known to be feasible for obtaining functionally equivalent aminoacid sequences (Huang 1986; Zabin, Horvath et al. 1991; Edgar and Schwartz 1992; Sardana, Emini et al. 1992; Xu, Kapfer et al. 1992; Lamande and Bateman 1993; Verdoliva, Ruvo et al. 1995; Yu, Schurr et al. 1995; Wehrmann, Van Vliet et al. 1996; Ullmann, Hauswald et al. 1997; Minuth, Kramer et al. 1998; Ullmann, Hauswald et al. 2000; Janke, Martin et al. 2003): from 0 to 3 in CDR1 (SEQ ID No.1), from 0 to 2 in CDR2 (SEQ ID No. 2), from 0 to 2 in CDR3 (SEQ ID No. 3), from 0 to 1 in CDR4 (SEQ ID No. 4), From 0 to 4 in CDR5 (SEQ ID No. 5), from 0 to 2 in CDR6 (SEQ ID No. 6), or aminoacids substituted with other aminoacids having equivalent chemical functions and properties, as well known by the skilled man in the art (also called "aminoacid similarity") as indicated, for an example, in the following list of similar aminoacids (one letter code): G or A, F or Y, D or E, N or Q, K or R or H, S or T, C or M, V or L or I, W or P, and/or substituted according to previous art (Huang 1986; Zabin, Horvath et al. 1991; Edgar and Schwartz 1992; Sardana, Emini et al. 1992; Xu, Kapfer et al. 1992; Lamande and Bateman 1993; Verdoliva, Ruvo et al. 1995; Yu, Schurr et al. 1995; Wehrmann, Van Vliet et al. 1996; Ullmann, Hauswald et al. 1997; Minuth, Kramer et al. 1998; Ullmann, Hauswald et al. 2000; Janke, Martin et al. 2003) within said sequences SEQ ID No.1 to SEQ ID No. 6.

These variants are the result of deletions, additions or substitutions of amino acids in the peptides of SEQ ID Nos. 1 to 6 and are also encompassed by the present invention and can be obtained by methods known in the art such as by site directed mutagenesis or by chemical synthesis.

The ligands of the present invention have the ability to bind to the antiligand of the present invention.

According to the present invention, by the expression "bind" or "binding" it shall be understood that the ligand recognizes significantly the anti-ligand according to the criteria given in example 5.

In another aspect of the invention, said ligand, comprises a light chain variable region (VL) comprising the complementary-determining regions (CDRs) having the amino acid sequences SEQ ID No. 1, SEQ ID No. 2 and SEQ ID No. 3 or any sequence having at least 80% of identity and more preferably 90% of identity with said sequences, and a heavy chain variable region (VH) domain comprising the CDRs having the amino acid sequences SEQ ID No. 4, SEQ ID No. 5 and SEQ ID No. 6 or any sequence having at least 80% of identity and more preferably 90% of identity with said sequences.

In a further aspect the ligand of the invention comprises a light chain variable region (VL) having the amino acid sequences set forth in SEQ ID No. 7, or any sequence having at least 75% of identity and more preferably 80% and even more preferably 90% of identity with said sequence and a heavy chain variable region (VH) having the amino acid sequence set forth in SEQ ID No. 8 or any sequence having at least 75% of identity and more preferably 80% and even more preferably 90% of identity with said sequence.

The variants of these VH and VL sequences according to the present invention significantly bind to the antiligand.

"Sequence identity" means, for example, that in a sequence having 80% sequence identity, 80% identical amino acids are present in the same position upon alignment of the sequences, which alignment can be performed by known methods in the art such as those described in Sequence—Evolution—Function Computational Approaches in Comparative genomics. Koonon E. et al., 2003: Kluwer Academic Publishers or according to default parameters of "Mac Vector" Software (UK) instruction book.

The ligand of the present invention can also be defined as being comprised within a recombinant scFV protein.

According to further aspects of the invention, the ligand can be comprised in a Fab fragment, in an antibody, said antibody can be a polyclonal, monoclonal, oligoclonal, a chimerized, engineered or a humanized antibody. In a particular aspect of the invention, the antibody comprising the ligand is a human IgG, and more particularly and IgG1 or an IgG4.

Polyclonal, oligoclonal, monoclonal antibodies can be produced by classical methods such as those described by Kohler and Milstein (1975) or using the procedures described in Sambrook et al, A Guide to Molecular Cloning, A Laboratory Manual, 2$^{nd}$ edition (1989) using the anti-ligands described above.

More particularly, the anti-ligand of the present invention that is used to obtain the antibodies is the anti-ligand consisting of SEQ ID No. 20 or of SEQ ID No. 32 or any sequence having at least 75% sequence identity to the sequences set forth in SEQ ID No. 20 or SEQ ID No. 32 or any sequence 100% complementary thereof.

In particular under the form of a peptide linked to a carrier protein such as serum albumin or KLH commonly used for immunization.

The invention also relates to a pharmaceutical composition comprising the ligand of the invention as an active ingredient. This ligand can also be present in the pharmaceutical composition in the form of a ScFv, a Fab fragment or of an antibody.

The pharmaceutical composition of the invention is used for treating MSRV associated diseases.

Within the meaning of the present invention "treatment" encompasses either prophylactic or curative treatments.

The pharmaceutical composition of the present invention is administered in amounts that will be therapeutically effective and immunogenic and as known in the art, the dosage that is administered depends on the individual to be treated.

In a further aspect, the invention deals with a method of treatment comprising administrating the ligand, the ScFv, the Fab fragment or the antibody or the ligand in any molecular or suitable therapeutic vector maintaining its binding properties as disclosed above or the pharmaceutical composition as described above.

The method of treatment of the invention aims at treating MSRV associated diseases.

MSRV, is a human retrovirus first isolated from patients with multiple Sclerosis (Perron, H., B. Lalande, et al. (1991), Lancet 337(8745): 862-3; Perron, H., J. A. Garson, et al. (1997), Proc Natl Acad Sci USA 94(14): 7583-8). Associated diseases or syndromes are defined by the presence in corresponding patients either (i) of specific MSRV RNA or antigens, preferably detected in body fluids (blood, cerebrospinal fluid, urine . . . ), either (ii) of elevated DNA or RNA copy number in cells or tissues from organs with lesions or dysfunctions, either (iii) of specific MSRV proteins or antigens in cells or tissues involved in the process of the disease or of the clinical syndrome, or (iv) of MSRV proteins or antigens in body fluids of individuals with the disease or expressing the clinical syndrome (as described in example 8, see below and others below). As MSRV has genetic homology with the Human Endogenous Retroviral type W (HERV-W) family (Blond et al., 1999; Dolei, 2005; Dolei and Perron, 2008) alternative or complementary definition of MSRV-associated diseases can also be obtained with HERV-W nucleic acids, antigens or proteins used for the same detection tests (Antony et al., 2004; Arru et al., 2007; Karlsson et al., 2004; Mameli et al., 2007). Moreover, MSRV expression can be associated with upregulation of certain HERV-W copies co-detected in pathogenic lesions (Mameli et al., 2009). Thus the definition of MSRV-associated diseases implicitly comprises association with HERV-W elements.

MSRV-associated disease is selected from the group comprising multiple sclerosis, schizophrenia, clinically isolated syndrome (CIS, with neurological symptom), chronic inflammatory demyelinating polyneuropathy, epilepsy, psoriasis, cancer, inflammatory pancreatitis and diabetes such as type 1 or type 2 diabetes, when associated with inflammation or immune dysregulation and with the presence of MSRV expression products as defined above.

In a particular embodiment, the method of treatment of MSRV-associated diseases comprises the administration of the IgG4 or IgG1 antibody as a chronic treatment with regularly repeated injections.

In another aspect the invention deals with a nucleic acid molecule comprising at least one full length nucleic acid sequence set forth in SEQ ID No. 13, SEQ ID No. 14, SEQ ID No. 15, SEQ ID No. 16, SEQ ID No. 17, SEQ ID No. 18 or any sequence having at least 70% and more preferably 80% and even more preferably 90% of identity with said sequences or any sequence 100% complementary thereof.

"Sequence identity" means, for example, that in a sequence having 80% sequence identity, 80% identical nucleotides are present in the same position upon alignment of the sequences, which alignment can be performed by known methods in the art. (see above)

In a preferred embodiment of the above aspect of the invention, the nucleic acid molecule comprises each of the sequences set forth in SEQ ID No. 13, SEQ ID No. 14, SEQ ID No. 15, SEQ ID No. 16, SEQ ID No. 17 and SEQ ID No. 18 or any sequence having at least 70% and more preferably 80% and even more preferably 90% of identity with said sequences or any sequence 100% complementary thereof.

In a further aspect of the invention, the nucleic acid encodes a VH chain, and more particularly, is represented by SEQ ID No. 10 or 12 or any sequence having at least 70% and more preferably 80% and even more preferably 90% of identity with said sequences or any sequence 100% complementary thereof, without limitation to previously described percentages of substitutions, insertions and deletions maintaining antigenic and binding properties of the original Ligand or anti-Ligand molecules (Huang 1986; Zabin, Horvath et al. 1991; Edgar and Schwartz 1992; Sardana, Emini et al. 1992; Xu, Kapfer et al. 1992; Lamande and Bateman 1993; Verdoliva, Ruvo et al. 1995; Yu, Schurr et al. 1995; Wehrmann, Van Vliet et al. 1996; Ullmann, Hauswald et al. 1997; Minuth, Kramer et al. 1998; Ullmann, Hauswald et al. 2000; Janke, Martin et al. 2003).

The nucleic acid sequence can also encode a VL chain that is represented by sequences SEQ ID No. 9 or 11 or any sequence having at least 70% and more preferably 80% and even more preferably 90% of identity with said sequences or any sequence 100% complementary thereof without limitation to previously described percentages of substitutions, insertions and deletions maintaining antigenic and binding properties of the original Ligand or anti-Ligand molecules (Huang 1986; Zabin, Horvath et al. 1991; Edgar and Schwartz 1992; Sardana, Emini et al. 1992; Xu, Kapfer et al. 1992; Lamande and Bateman 1993; Verdoliva, Ruvo et al. 1995; Yu, Schurr et al. 1995; Wehrmann, Van Vliet et al. 1996; Ullmann, Hauswald et al. 1997; Minuth, Kramer et al. 1998; Ullmann, Hauswald et al. 2000; Janke, Martin et al. 2003).

Any nucleic acids hybridizing under stringent conditions with nucleic acids encoding at least one of the peptides according to the invention is also embraced by the invention. As used herein, the term "stringent conditions" refers to conditions which permit hybridization between the probe sequences and the nucleotide sequence to be detected. Suitable stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The present invention also relates to a chimeric gene comprising, functionally linked to one another, at least one promoter which is functional in a host organism, a nucleic acid according to the invention, and a terminator element that is functional in the same host organism. The various elements which a chimeric gene may contain are, firstly, elements regulating transcription, translation and maturation of proteins, such as a promoter, a sequence encoding a signal peptide or a transit peptide, or a terminator element constituting a polyadenylation signal and, secondly, a polynucleotide encoding a protein. The expression "functionally linked to one another" means that said elements of the chimeric gene are linked to one another in such a way that the function of one of these elements is affected by that of another. By way of example, a promoter is functionally linked to a coding sequence when it is capable of affecting the expression of said coding sequence. The construction of the chimeric gene according to the invention and the assembly of its various elements can be carried out using techniques well known to those skilled in the art, in particular those described in Sambrook et al. (1989, Molecular Cloning: A Laboratory Manual, Nolan C. ed., New York: Cold Spring Harbor Laboratory Press). The choice of the regulatory elements constituting the chimeric gene depends essentially on the host organism in which they must function, and those skilled in the art are capable of selecting regulatory elements which are functional in a given host organism. The term "functional" is intended to mean capable of functioning in a given host organism.

The promoters which the chimeric gene according to the invention may contain are either constitutive or inducible. By way of example, a universally potent promoter used for expression in Mammalian cells is pCMV (Cytomegalovirus promoter).

According to the invention, the chimeric gene may also comprise other regulatory sequences, which are located between the promoter and the coding sequence, such as transcription activators (enhancers).

The present invention also relates to a cloning and/or expression vector comprising a chimeric gene according to the invention. The vector according to the invention is of use for transforming a host organism and expressing in this organism a ligand. This vector may be a plasmid, a cosmid, a bacteriophage or a virus. Preferentially, the transformation vector according to the invention is a plasmid. Generally, the main qualities of this vector should be an ability to maintain itself and to self-replicate in the cells of the host organism, in particular by virtue of the presence of an origin of replication, and to express a ligand therein. For the purpose of stable transformation of a host organism, the vector may also integrate into the genome. The composition of the vector may then be limited to the elements required for synthesizing the ligand in the hosts. The choice of such a vector, and also the techniques of insertion of the chimeric gene according to the invention into this vector, are thoroughly described in Sambrook et al. (1989, Molecular Cloning: A Laboratory Manual, Nolan C. ed., New York: Cold Spring Harbor Laboratory Press) and are part of the general knowledge of those skilled in the art. Advantageously, the vector used in the present invention also contains, in addition to the chimeric gene according to the invention, a chimeric gene encoding a selectable marker. This selectable marker makes it possible to select the host organisms which are effectively transformed, i.e. those which incorporated the vector. Mention may be made of genes encoding readily identifiable enzymes such as the GUS enzyme, or genes encoding pigments or enzymes regulating the production of pigments in the transformed cells. Such selectable marker genes are in particular described in patent applications WO 91/02071, WO 95/06128, WO 96/38567 and WO 97/04103.

The present invention also relates to transformed host organisms containing at least one chimeric gene according to the invention, either integrated into their genome or carried on an extrachromosomal genetic element, for example a plasmid. The term "host organism" is intended to mean any lower or higher monocellular or pluricellular organism into which the chimeric gene according to the invention may be introduced in order to produce a ligand according to the invention. Preferably, the host organism is CHO (Chinese Hamster Ovary) or HEK (Human Epthelium Kidney) cells.

The expression "transformed host organism" is intended to mean a host organism which has incorporated into its genome, or in an extrachromosomal genetic element, for example a plasmid, at least one chimeric gene according to the invention, and consequently produces a ligand in its tissues, or in a culture medium. To obtain the host organisms according to the invention, those skilled in the art may use one of the many known transformation methods.

One of these methods consists in bringing the cells or tissues of the host organisms to be transformed into contact with polyethylene glycol (PEG) and with the vectors according to the invention (Chang and Cohen, 1979, Mol. Gen. Genet. 168(1), 111-115; Mercenier and Chassy, 1988, Biochimie 70(4), 503-517). Electroporation is another method, which consists in subjecting the cells or tissues to be transformed and the vectors of the invention to an electric field (Andreason and Evans, 1988, Biotechniques 6(7), 650-660; Shigekawa and Dower, 1989, Aust. J. Biotechnol. 3(1), 56-62). Another method consists in directly injecting the vectors into the cells or the tissues by microinjection (Gordon and Ruddle, 1985, Gene 33(2), 121-136). Advantageously, the "biolistic" method may be used. It consists in bombarding cells or tissues with particles onto which the vectors of the invention are adsorbed (Bruce et al., 1989, Proc. Natl. Acad. Sci. USA 86(24), 9692-9696; Klein et al., 1992, Biotechnology 10(3), 286-291; U.S. Pat. No. 4,945, 050).

The invention also encompasses a method for the production of the ligand, the ScFv, the Fab fragment or the antibodies described above comprising the step of culturing the host cell described above under conditions that allow the synthesis of ligand, Fab fragment or antibody.

The ligand of the invention is characterized by its binding properties to an anti-ligand. In a specific form the anti-ligand of the invention is characterized in that it consists in the amino acid sequence defined by SEQ ID No. 20, with preferred selection represented by SEQ ID No. 32.

A method of detection in a biological sample of the antiligand, using the ligand in the form of a ScFv, a Fab fragment or an antibody according to the present invention, is also part of the present invention. The method comprises the steps of:

(a) contacting the sample with the ligand according to the invention, the ScFv, the Fab fragment or an antibody as described above, (b) detecting the presence of anti-ligand in the sample.

Figure 17:
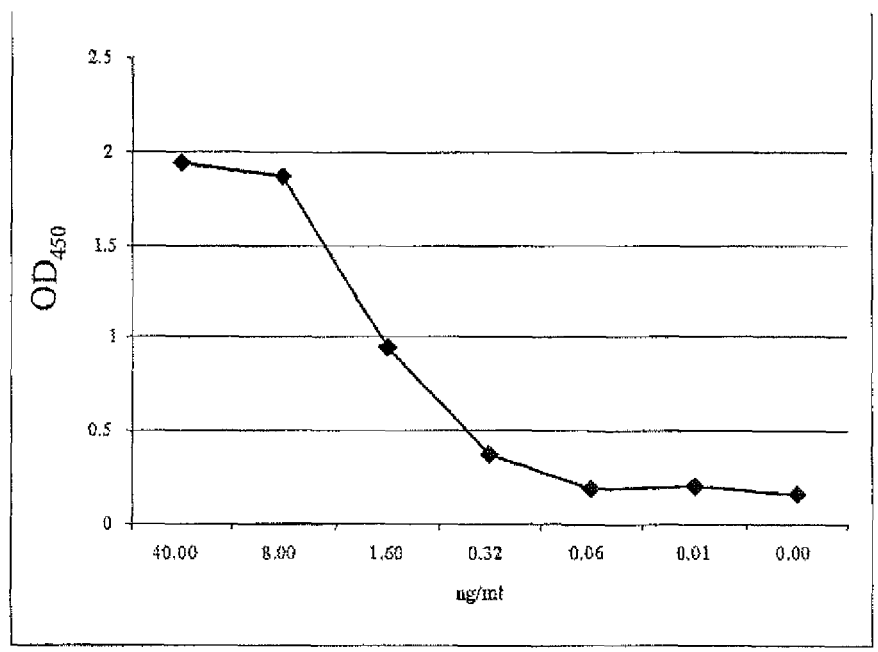

Said method of detection can be completed by an additional step of contacting the sample with a ligand that specifically binds to MSRV GAG antigen, encoded by MSRV gag gene as described in "Komurian-Pradel et al. Virology, 1999; 260(1), pages 1-9".

According to another aspect, the present invention also deals with an immunoassay kit for the detection of the anti-ligand in a biological sample, said kit comprising a ligand according to the invention, a ScFV, a Fab fragment or an antibody as described above, and reagents for the detection of specific binding of anti-ligand to the above ligand, Fab fragment or antigen, said kit also comprising all the reagents necessary for the immunological reaction.

Said kit can additionally comprises a ligand that specifically binds to GAG antigen, as previously defined.

According to another aspect, the present invention also deals with the use of such immunoassay kit, as described above, in the detection of an MSRV-associated disease selected from the group comprising multiple sclerosis, schizophrenia, clinically isolated syndrome, chronic inflammatory demyelinating polyneuropathy, epilepsy, psoriasis, cancer, inflammatory pancreatitis and diabetes, and more particularly type 1 diabetes or type 2 diabetes.

The biological sample can be sera, urine, saliva, biopsy material and the like.

The design of immunoassays is conventional in the art and protocols such as the use of solid supports or immunoprecipitation are well known techniques. The antibody can be labeled for detection purposes using enzymatic, fluorescent, chemiluminescent, radioactive or dye labels. Assays that amplify the signals from the immune complex such as assays using biotin and avidin or streptavidin and enzyme-linked immunoassays such as ELISA or sandwich assays are part of the present invention.

FIGURES

FIG. 1: (A) VL amino acid sequence, (B) VH amino acid sequence, the CDR sequences are underlined FIG. 2: structure of complete ENV protein (ENV-T) and surface cleavage fragment (ENV 1 or ENV-SU)

FIG. 3: Optic density measure by colorimetry with peroxydase substrate comparing murine GNb AC1 antibody Ligand (murine IgG1 perox) and recombinant ScFv Fragment with Ligand (ScFv VH+VL biot) only.

The concentration of the coating antibody and of each detection Ligand was 5 µg/ml each; streptavidin-peroxidase conjugate dilution was 1/2000.

FIG. 4: Optic density measure by colorimetry with peroxydase substrate comparing murine GNb AC1 anibody Ligand and Fab binding Fragment with Ligand only. The concentration of each detection Ligand or IgG1 was 10 g/ml+Jackson peroxidase anti-Fab or anti-IgG diluted at 1/250. Different ENV-T concentrations were tested.

FIG. 5: test of GNbAC1 and chimeric antibodies IgG1 and IgG4 according to the invention on serial dilution of ENV antigen (ENV-T). The concentration of antibodies was 1 mg/ml and the secondary peroxydase-labeled antibody anti IgG 1/250. 2G5E12 antibody is an irrelevant antibody that does not bind to ENV antigen, used here as a negative control.

FIG. 6: Test of GNbAC1 and chimeric constructions IgG1 and IgG4 on constant antigen concentration (ENV-T) on two lots of ligands (A) lot 1, (B) lot 2. The concentration of antigen was of 1 to 0.0078 original murine monoclonal antibody (GNb AC1), indicated as mulgG, the human IgG1 or IgG4 constructs with the Ligand (indicated as hulgG1 and hulgG4. µg/ml. The dilution of the Jackson anti-mouse or anti-human IgG secondary antibody was: 1/250.

FIG. 7: GNbAC1, ScFv, IgG1 and IgG4 chimeric human antibody constructs with Ligand: inhibition of PBMCs pro-inflammatory activation by ENV antigen (ENV SU) as represented by the reduction of IL-6. The ratio between the antibody or ScFv and ENV antigen was 25/1.

FIG. 8: ApoH-ELISA results. Sera from the European multicenter study on Multiple Sclerosis were tested blindly in an independent laboratory.

FIG. 9: MSRV-ENV and GAG antigeneamia in patients with schizophrenia and controls. Antibodies used are 2A12A5 and 6A2B2 for ENV and 2G5E12 for GAG.

FIG. 10: Optical density (OD) of ApoH-ELISA for the detection of MSRV-ENV antigen with 6A2B2 specific monoclonal antibody.

FIG. 11: Clinical follow up of humanized SCID mice developing acute neuroinflammation and demyelization (experimental allergic encephalomyelitis, an animal model of Multiple Sclerosis): comparison of clinical outcome of groups treated with different antibodies compared to non treated groups. The original murine monoclonal antibody (GNb AC1) is indicated as mulgG, the human IgG1 or IgG4 constructs with the Ligand are indicated as hulgG1 and hulgG4.

FIG. 12: survival curves of humanized SCID mice developing acute neuroinflammation and demyelization (experimental allergic encephalomyelitis, an animal model of Multiple Sclerosis): comparison of clinical outcome of groups treated with different antibodies compared to non treated groups. The original murine monoclonal antibody (GNb AC1) is indicated as mulgG, the human IgG1 or IgG4 constructs with the Ligand are indicated as hulgG1 and hulgG4.

FIG. 13: Weight curves of each NOD-SCID mouse tested in the present experiment.

The dose of ENV protein injected for each mouse is indicated in brackets. The last injection of ENV protein emulsified in IFA and PTX (P14) is indicated by the arrow. The mice are named M1 to M6, according to the dose of ENV they have received, which is indicated next to the code between brackets (from 0 to 20 micrograms) in the graphical legend. Interruption of the curves corresponds to the day of the animal death in the corresponding category.

FIG. 14: Blood glucose (Glycemia) concentrations in control (control) and ENV-injected NOD-SCID mice (ENV): comparison between the day of the first injection (P0) and one week after the last injection (P30). The glycemia measured at P30 is expressed as a percentage of that measured at P0 (Y-axis) in mock-Injected and ENV-Injected groups (X axis:—Controls and "ENV").

FIG. 15: CDR definition of GNb AC1 antibody heavy chain

15A: Aminoacids identified according to Chothia definition are presented with lower letter size. Aminoacids identified according to Kabat definition are presented with underlined letters.

15B: According to the preferred Definition combining both determination, the original murine CDR regions to be considered for functional ligand grafting into human IgG4 antibody variable Heavy chain are underlined.

FIG. 16: CDR definition of GNb AC1 antibody light chain.

CDR identified according to Kabat definition are underlined CDR identified according to Contact definition (not standard) have lower size letters.

FIG. 17: Binding activity of chimeric GNb AC1 antibody to immobilized ENV protein. Conditions are described in the text of corresponding example. The Y axis represents the Optic density (OD) measure for each point by colorimetry and correlate the quantity of antibody bound to the target ENV protein. The X axis represents the concentration of ENV recombinant protein used for coating the corresponding wells of the microplate and, after washing, obtain a wide quantitative spectrum of corresponding plate-immobilized protein.

Figure 18:
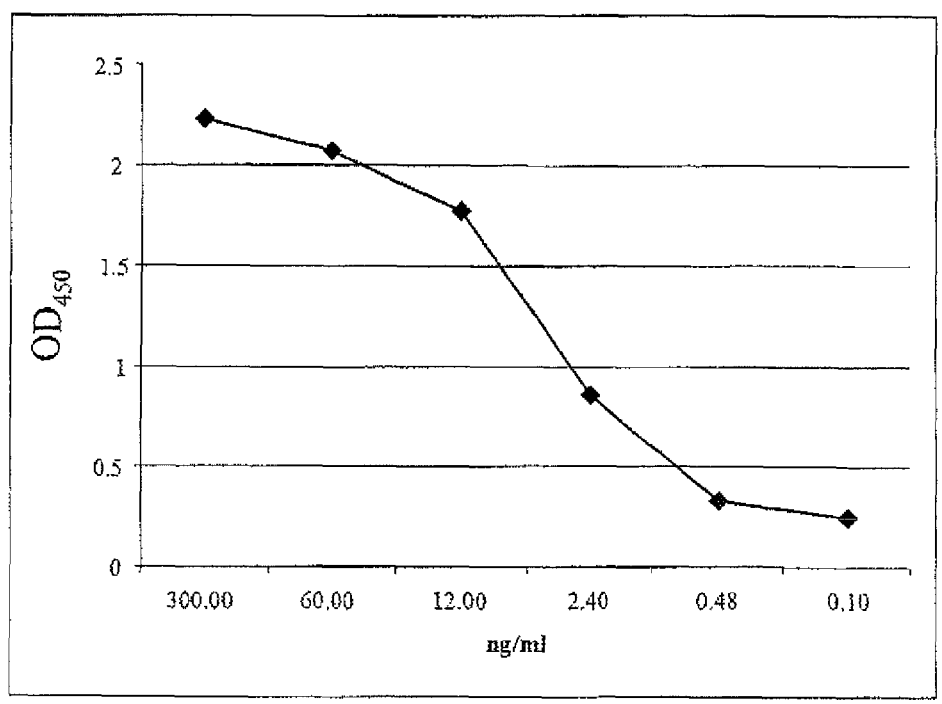

FIG. 18: Binding activity of humanized antibody H2/VK3 to immobilized ENV. Conditions are described in the text of corresponding example. The Y axis represents the Optic density (OD) measure for each point by colorimetry and correlate the quantity of antibody bound to the target ENV protein. The X axis represents the concentration of ENV recombinant protein used for coating the corresponding wells of the microplate and, after washing, obtain a wide quantitative spectrum of corresponding plate-immobilized protein of corresponding plate-immobilized protein.

Figure 19:
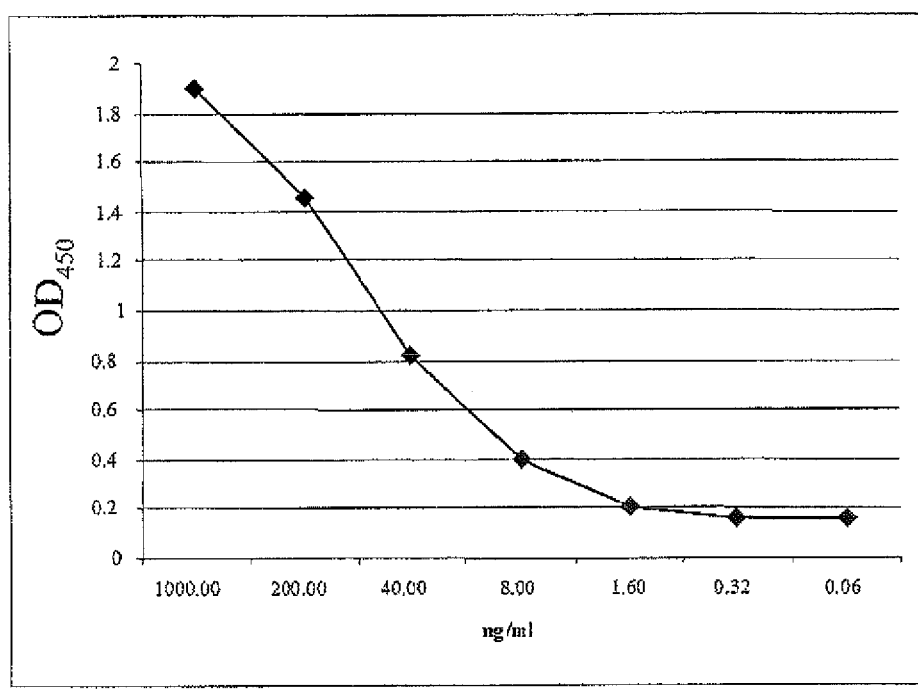

FIG. 19: Binding activity of humanized antibody H4/VK3 to immobilized ENV. Conditions are described in the text of corresponding example. The Y axis represents the Optic density (OD) measure for each point by colorimetry and correlate the quantity of antibody bound to the target ENV protein. The X axis represents the concentration of ENV recombinant protein used for coating the corresponding wells of the microplate and, after washing, obtain a wide quantitative spectrum of corresponding plate-immobilized protein.

Figure 20:
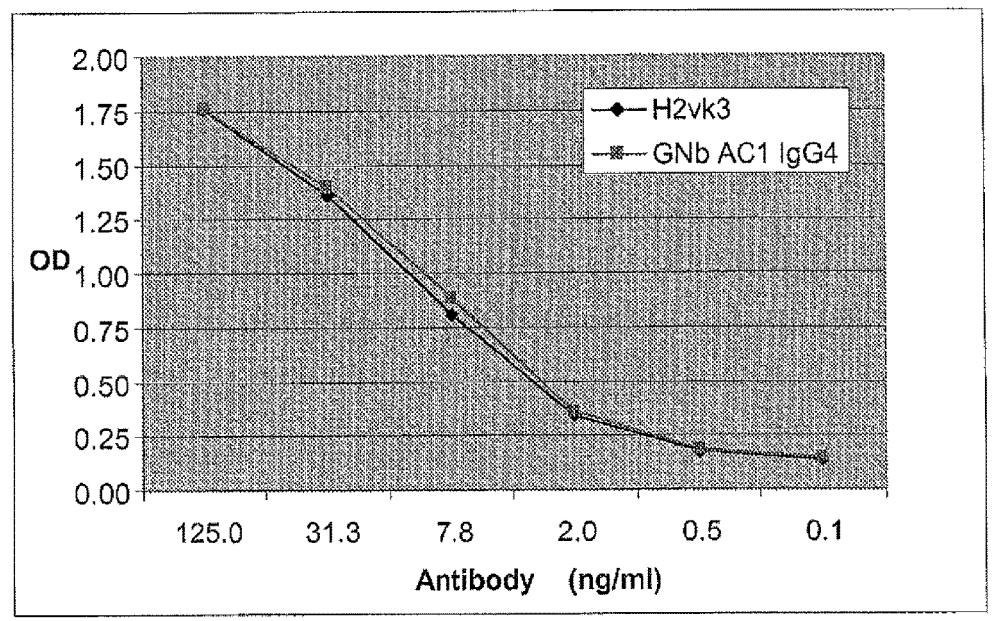

FIG. 20: Comparison of binding activity of humanized antibody H2/VK3 (H2vk3) and chimeric antibody (GNbAC1 IgG4) to immobilized ENV. Conditions are described in the text of corresponding example. The Y axis represents the Optic density (OD) measure for each point by colorimetry and correlate the quantity of antibody bound to the target ENV protein The X axis represents the concentration of ENV recombinant protein used for coating the corresponding wells of the microplate and, after washing, obtain a wide quantitative spectrum of corresponding plate-immobilized protein.

Figure 21:
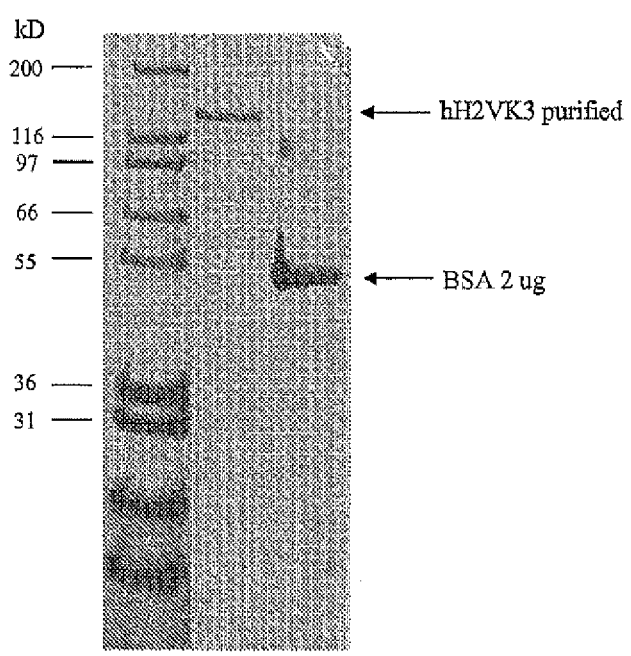
Figure 22:
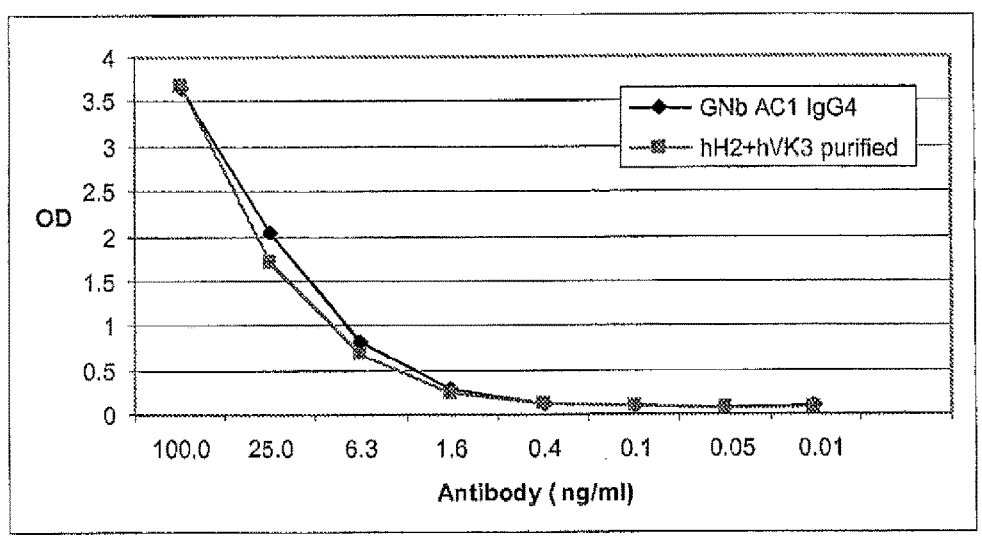

FIG. 21: Purified H2VK3 antibody in non-reducing gel Conditions are described in the text of corresponding example. On the left, KD numbers indicate the levels (Bars) at which standard proteins with defined molecular weight (KD) have migrated in the gel, as shown in the left lane of the picture. The purified H2/VK3 antibody is shown (arrow) as a single band in the middle lane of the picture, with Bovine serum Albumin (standard in Antibody buffers, as a control shown by arrow at a different molecular weight), shown in the right lane of the picture;

FIG. 22: Comparison of binding activities of purified H2/VK3 (hH2+hVK3 purified) and purified chimeric antibody (GNbAC1 IgG4) to immobilized ENV (0.5 microg/ml).
The X axis represents The IgG4 chimeric or Selected Humanized antibody concentration in nanog/ml. The Y axis represents the Optic density measured by colorimetry, correlating the quantity of antibody bound to the immobilized constant concentration of ENV protein in the assay.

FIG. 23: Amino acid sequences of the humanized antibody H2 heavy chain and VK3 light chain.
The aminoacids in superscript bold letters represent murine aminoacids kept in the framework, based on their consensus position with human antibody sequences analyzed in databases.

Figure 24:
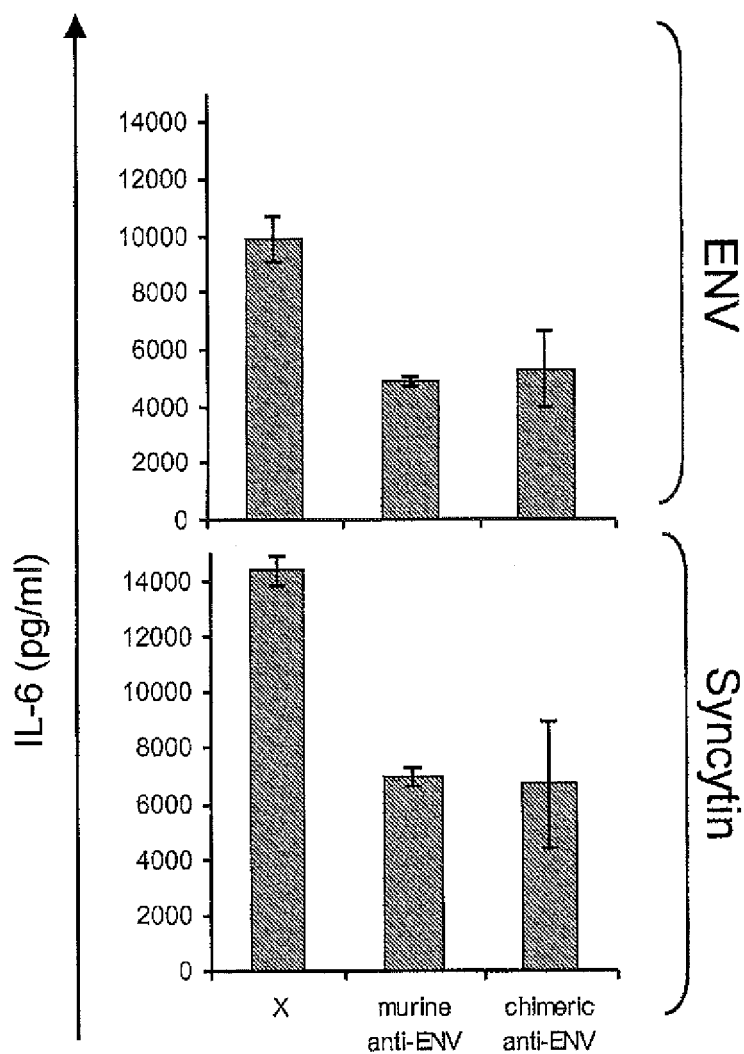

FIG. 24: Pro-Inflammatory cytokines are strongly upregulated by stimulation of astrocyte cells with HERV-W ENV related proteins Results are presented as the mean of triplicates values.ENV: MSRV-ENV; Syncytin: HERV-W ENV from Chromosome 7q copy; X: Irrelevant antibody (control Isotype); Murine anti-ENV: GNb AC1 murine antibody; Chimeric anti-ENV: GNb AC1Chimeric Human IgG4; Pg/ml: Picograms per Milliliter FIG. 25: Peripheral Blood Mononuclear Cell Cultures
Results are presented as the mean of triplicates values.ENV: MSRV-ENV; Syncytin: HERV-W ENV from Chromosome 7q copy; X: Irrelevant antibody (control Isotype); Murine anti-ENV: GNb AC1 murine antibody; Chimeric anti-ENV: GNb AC1Chimeric Human IgG4; Pg/ml: Picograms per Milliliter FIG. 26: Detection of Human glycosylated reated HERV-W ENV proteins with three forms of the GNb AC1 Ligand (Murine, Chimeric and humanized antibody). A) Detection of Human glycosylated reated HERV-W ENV proteins with the GNb AC1 Murine antibody. B): Detection of Human glycosylated reated HERV-W ENV proteins with the GNb AC1 Chimeric antibody; C): Detection of Human glycosylated reated HERV-W ENV proteins with the humanized antibody. Y axis: Optic density; X axis: Bacterial MSRV-ENV Protein (ENV-T 7A batch); Bacterial MSRV-ENV Surface fragment (ENV-SU4A batch); Human Glycosylated Syncytin; Human Glycosylated MSRV-ENV protein (ENV-T P1 batch).

Figure 27:
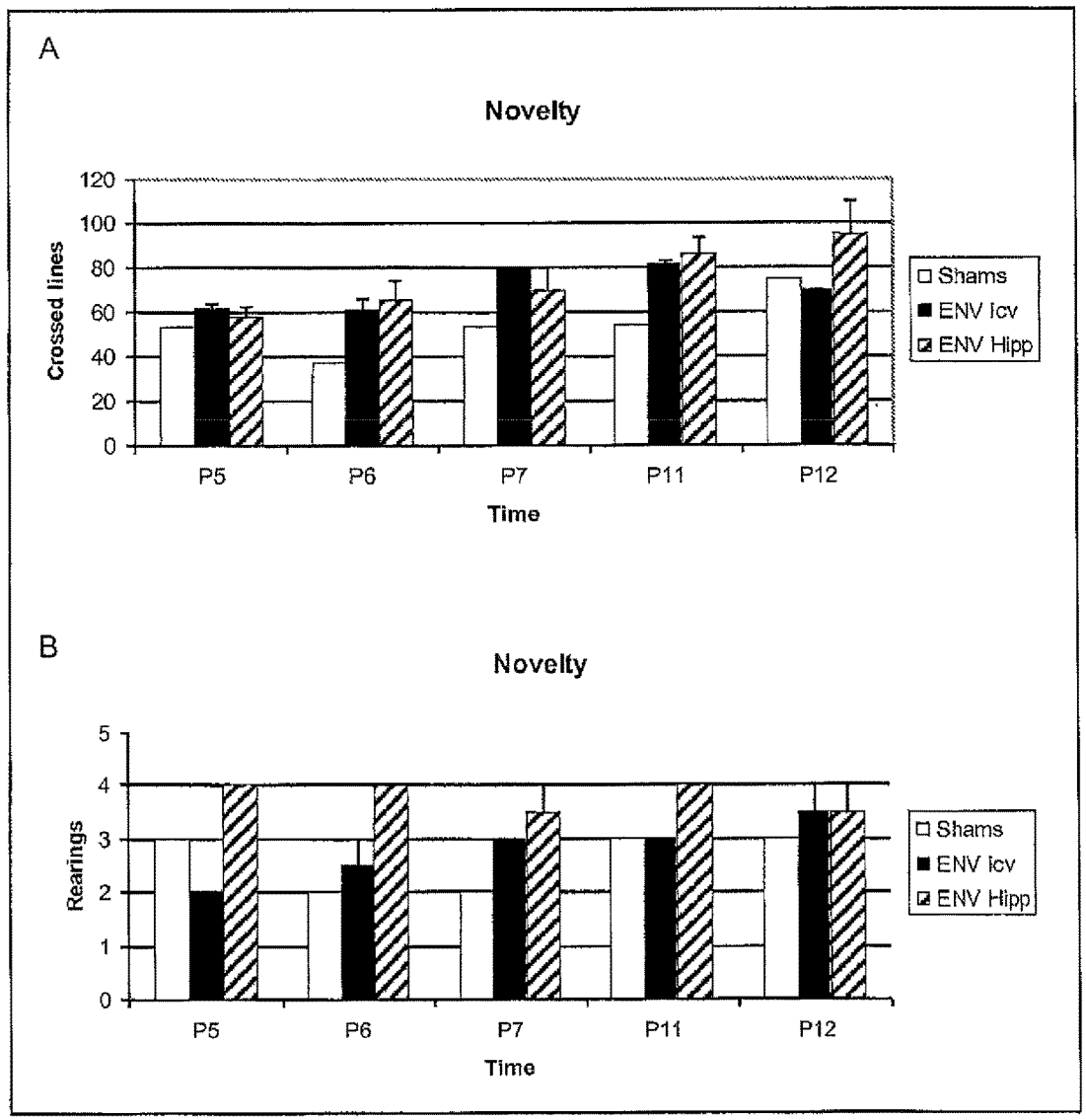

FIG. 27: Neurobehavioral scoring of Rats injected intracerebrally with MSRV ENV of Mock Solution (sham):
Horizontal—represented by crossed lines in Y axis—(A) and vertical—represented by rearings in Y axis—(B) locomotor activity after exposure to novelty at several time points after intracerebral injection (P5, P6, P7, P11 and P12) in sham (PBS Solution), ENV-icv (ENV injected Intra-Cerebral Ventricles) and ENV-hipp rats.

Figure 28:
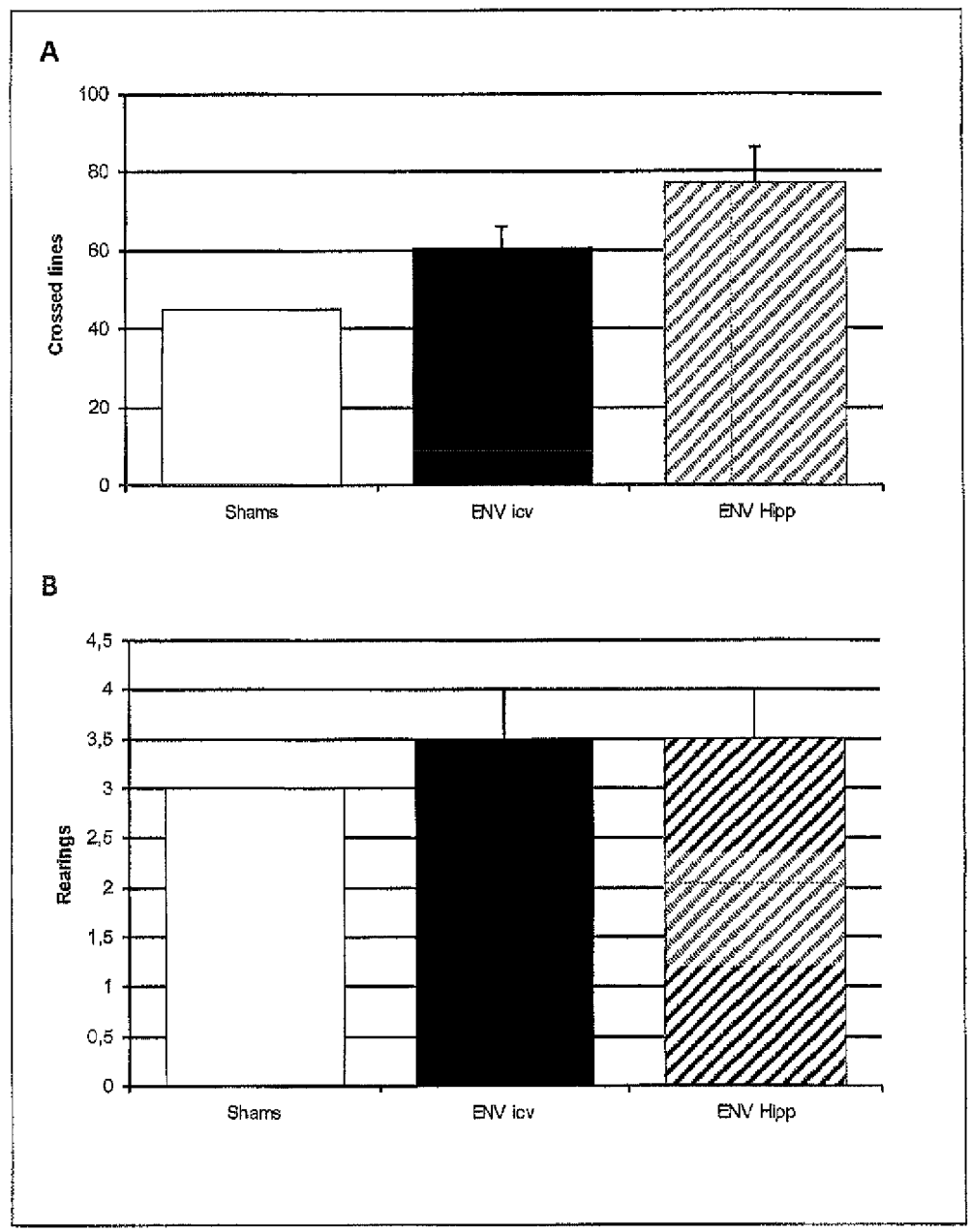

FIG. 28: Neurobehavioral scoring of Rats injected intracerebrally with MSRV ENV of Mock Solution (sham):
Horizontal—represented on Y axis by the number of crossed lines—(A) and vertical—represented on Y axis by the number of rearings—(B) locomotor activity after saline injection in sham, ENV-icv and ENV-hipp rats at P11.

Figure 29:
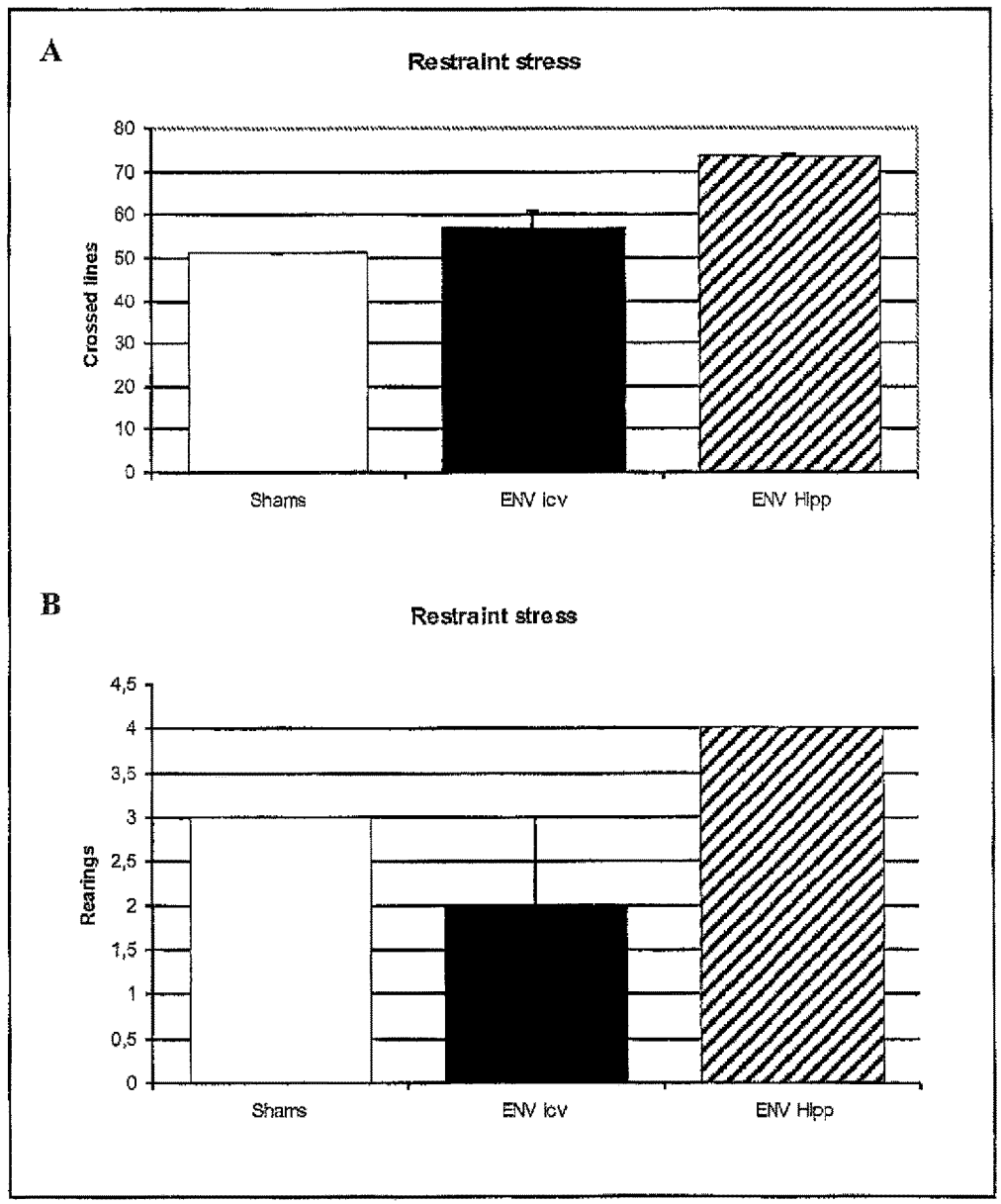

FIG. 29: Neurobehavioral scoring of Rats injected intracerebrally with MSRV ENV of Mock Solution (sham):
Horizontal—represented on Y axis by the number of crossed lines—(A) and vertical—represented on Y axis by the number of rearings—(B) locomotor activity after restraint stress in sham, ENV-icv and ENV-hipp rats at P13.

Figure 30:
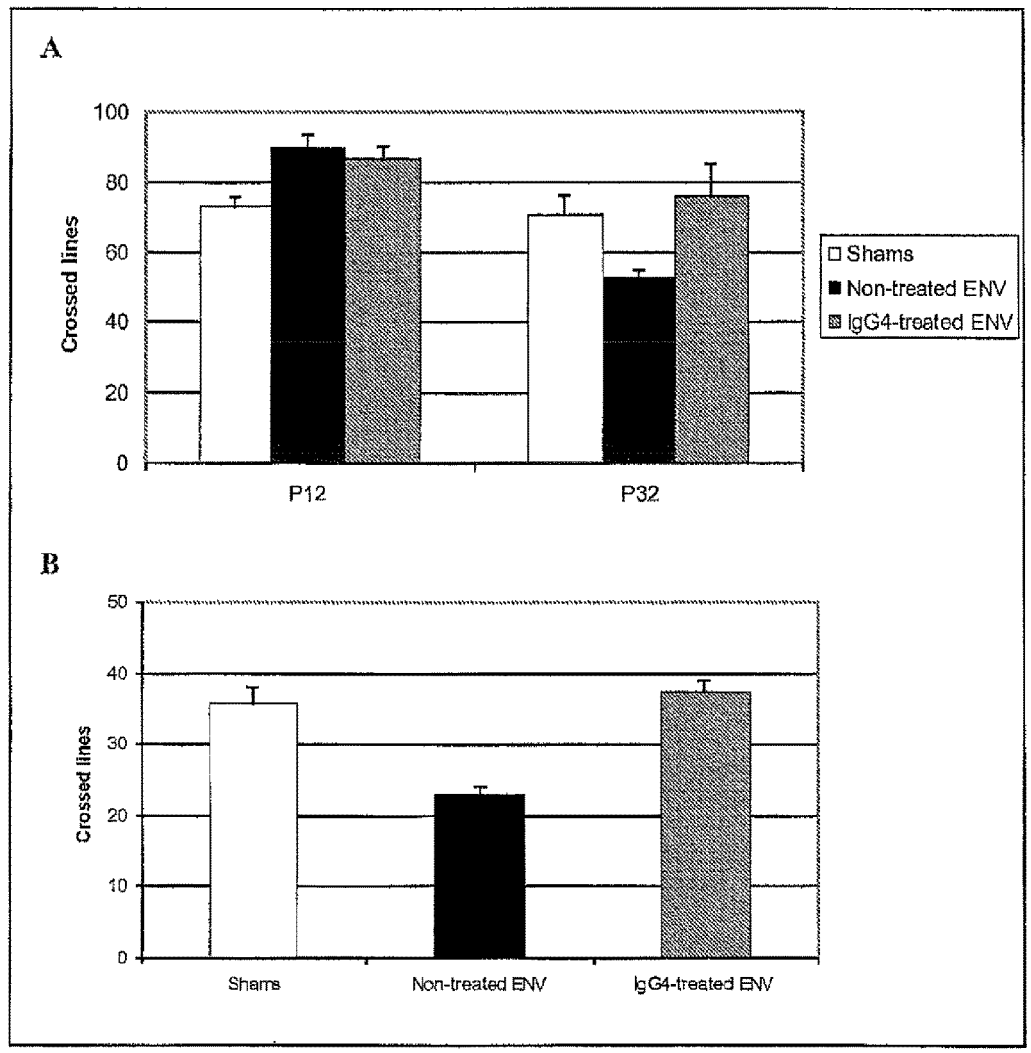

FIG. 30: Neurobehavioral scoring of Rats injected intracerebrally with MSRV ENV showing therapeutic effect of The IgG4 GNbAC1 Ligand:
(A) Horizontal locomotor activity measured in an open-field after exposure to novelty at P12 and at P32—as indicated in the X axis—in sham rats, non-treated rats injected with ENV (ENV+), and IgG4-treated ENV+ rats, as indicated in the legend
(B) Confirmation of IgG4 Ligand therapeutic effect observed at P32 with horizontal locomotor activity after restraint stress; It is measured—number of crossed lines in the Y axis—in an open-field after a restraint stress after recall systemic injection of ENV protein in sham rats, non-treated ENV+ rats and IgG4-treated ENV+ rats, as indicated in the X axis.

Figure 31:
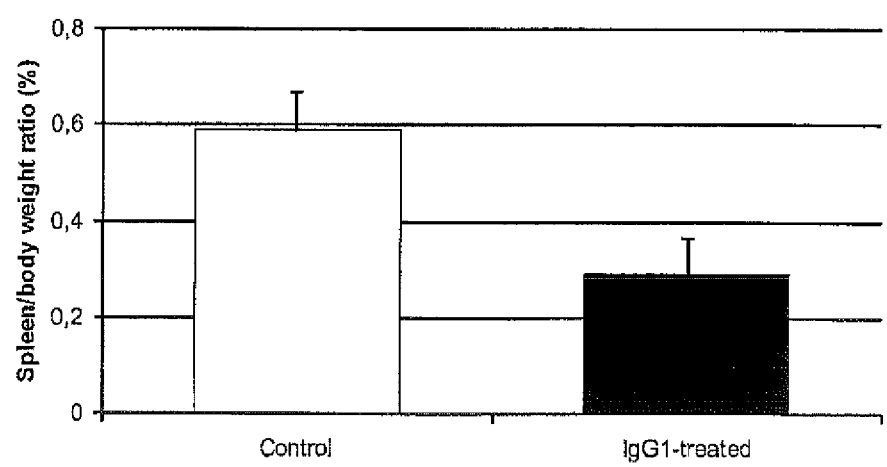

FIG. 31: Study of "ENV-positive"lymphoma-grafted Nude mice showing therapeutic effect of The IgG1 GNbAC1 Ligand Splenic index (Y axis) calculated on control and IgG1-treated mice (X-axis) 19 days after the injection of Lymphoma cells. The splenic index was calculated as follows: [(spleen weight/body weight)×100]. Non overlapping error bards indicate statistical significance.

Figure 32:
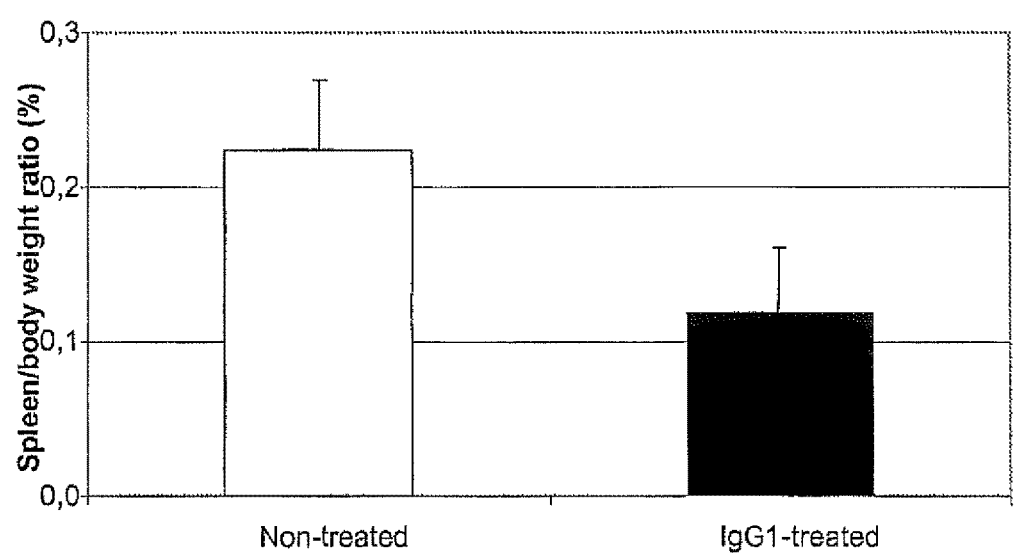

FIG. 32: Study of "ENV-positive"lymphoma-grafted SCID mice showing therapeutic effect of The IgG1 GNbAC1 Ligand Spleen/body weight ratio (Y-axis) calculated on non-tretated and IgG1-treated SCID mice 7 days after the injection of B-lymphoma cells. The spleen/body weight ratio was calculated as follows: [(spleen weight/body weight)×100].

Figure 33:
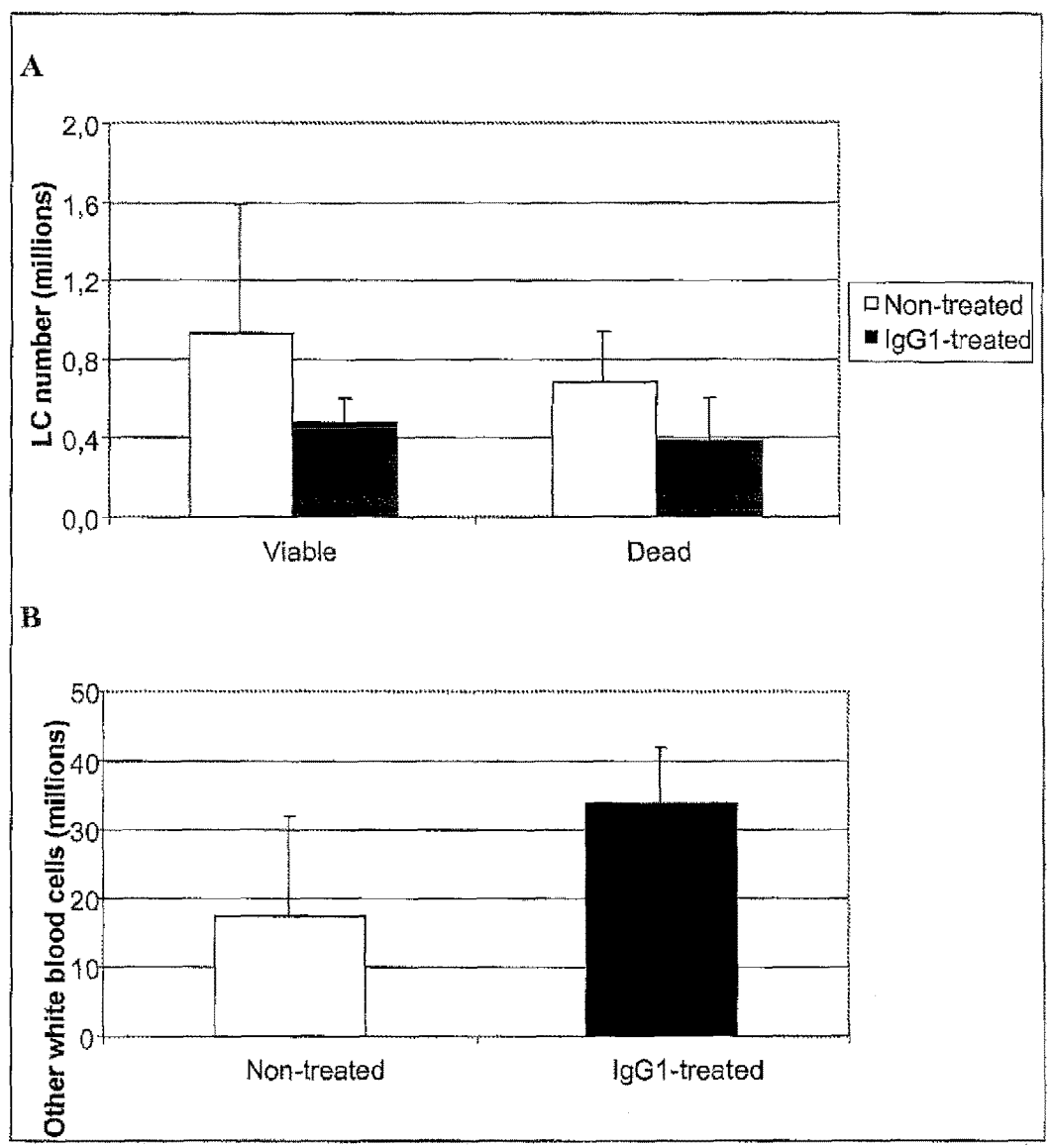

FIG. 33: Study of "ENV-positive"lymphoma-grafted SCID mice showing therapeutic effect of The IgG1 GNbAC1 Ligand Number of viable and dead lymphoblastoid cells—Y axis—(A), and of other white blood cells (B) in the peritoneal fluid collected in control and IgG1-treated mice—X axis—, 7 days after the injection of lymphoma cells and 6 days after antibody injection.

The following examples serve to illustrate the invention without limiting in any way the present invention.

EXAMPLES

Example 1

Analysis of Murine Specific Antibody (GNbAC1): Identification of the Sequence and Structure of a Molecular Ligand Specific for MSRV ENV Protein and its Equivalents A murine hybridoma was obtained after fusion of mouse myeloma and splenic cells from a Balb-C mouse immunised with a recombinant MSRV protein produced in *E. coli* and purified from an MSRV "ENV" clone, as described in 'Komurian-Pradel, F., G. Paranhos-Baccala, et al. (1999), Virology 260(1): 1-9).

The PCR amplification of VH and VL regions from this IgG1/Kappa (GNbAC1) producing hybridoma was made according to the following protocol.

Poly(A+) RNAs were extracted and purified from $5 \times 10^7$ hybridoma cells producing IgG1/Kappa using a mRNA purification kit (Amersham Bioscience) according to the manufacturer's instructions. Reverse transcription was performed from 800 ng mRNA using a RT-PCR kit (Amersham Bioscience) according to the manufacturer instructions. The cDNA encoding variable region gene sequences of light (VL) and heavy (VH) chains was obtained using the rapid amplification of cDNA ends (RACE) method, as previously described (Ruberti et al., 1994, J. Immunol. Methods 173, 33-39).

The forward primer was the following SEQ ID No. 21 (RACEforward), backward primers were the following: SEQ ID No. 22 (CL_Ala130_Fwd) VL amplification, and SEQ ID No. 23 (CH1_Pro119_Fwd) for VH amplification, with the letter code R=A/G, K=G/T, H=A/T/C. Backward primers CL_Ala130_Backward and CH1_Pro119_Backward, deduced from consensus sequences published by Kabat et al. (1991) Sequences of proteins of immunological interest. National Institute of Health Bethesda, Md.), are specific of N-terminal extremities of mouse kappa/CL domain and IgG/CH1 domain, respectively.

PCR products were obtained using the Taq DNA polymerase and directly ligated into the pCR®2.1-TOPO® vector using a TA cloning kit (Invitrogen) according to the manufacturer instructions. The sequences of cloned DNAs were determined by sequencing on ABI310 automatic sequencer using a Dye Terminator Cycle Sequencing Ready Reaction Kit (Applied Biosystems).

These PCR amplifications, followed by cloning and sequencing steps provided the sequences of VL and VH chains as represented SEQ ID No. 7 and 8, respectively, by their aminoacid sequences deduced from the original nucleotide sequences. In addition, the analysis of these aminoacid sequences has allowed the identification of the complementary determining regions (CDR) involved in the ligand specificity (according to Kabat (Wu and Kabat 1970, An analysis of the sequences of the variable regions of Bence Jones proteins and myeloma light chains and their implications for antibody complementarity. J. Exp. Med. 132:211-250; Kabat et al. 1987, 1991, Sequences of proteins of immunological interest; $4^{th}$ edn. US Govt. Printing Off. No. 165-492) or by structure according to Chothia (Chothia and Lesk 1987, Canonical structures for the hypervariable regions of immunoglobulins. J. Mol. Biol. 196:901-917; Chothia et al. 1989, Conformations of immunoglobulin hypervariable regions. Nature 342: 877-883).

The three CDR sequences are identified on the VH aminoacid sequence (FIG. 1 B) and correspond to SEQ ID No. 4, SEQ ID No. 5 and SEQ ID NO. 6 and three CDR sequences are identified on the VL aminoacid sequence (FIG. 1 A) correspond to SEQ ID No. 1, SEQ ID No. 2 and SEQ ID NO. 3. These six CDR sequences represent the core "minimum" sequences required for the binding specificity of the Ligand and, therefore, are comprised in any composition or molecular construct retaining the activity of the presently identified specific Ligand. Nonetheless, it is known from the man skilled in the art that few aminoacids can be substituted with equivalent properties, thus retaining the specificity of the original Ligand sequences and making it an equivalent Ligand. Such variations are known to be possible within a maximum range of 10-12%.

Example 2

Example of an MSRV ENV Antigen, Production and Purification for Mouse Immunisation in Order to Obtain Anti-ENV Reactive Splenocytes for the Generation of Specific Hybridomas Source: plasmid pV14 from MSRV virion (Perron, Jouvin-Marche et al. 2001) comprising the protein sequence corresponding to the Database accession number (NCBI-Entrez/Genbank): AF331500.1, FIG. 2 represents the structure of complete ENV protein (ENV-T, SEQ ID No. 19) and surface cleavage fragment (ENV 1 or ENV-SU, SEQ ID No.24). In FIG. 2 the Signal peptide starts at residue #1 (Methionine) and ends at residue #29 (Threonine).

Production Method:

After ligation of the ENV-T coding sequence provided by Geneart (USA) into the expression plasmid the expression vector pET-15b supplied by Novagen (EMD Chemicals, Inc., Gibbstown, N.J., UNITED STATES) according to the supplier instructions and transformation of bacteria BL21 *E. coli* strain by classical CaCl2 permeabilisation as described in "DNA Isolation and Sequencing" (Essential Techniques Series) by Bruce A. Roe, Judy S. Crabtree and Akbar S. Khan Published by John Wiley & Sons, ISBN 0-471-97324-0 QP625.N89R64 1996 John Wiley & Sons and in "Molecular Biology Techniques: An Intensive Laboratory Course (Paperback) by Katharine G. Field (Author), Walt Ream (Author), the transformed bacteria is grown in LB medium in presence of 30 µg/mL kanamycin at 37° C. until the optical density The expression of protein is then induced by 1 mM IPTG and the culture continues further at 37° C. during 4 hours.

Extraction Method:

After centrifugation at 5000 g 20 minutes 4° C., the bacterial pellet is resuspended in 20 mL/L of culture of lysis buffer (Tris 20 mM pH7.5; NaCl 0.15M; leupeptine 1 µg/mL, pepstatine 1 µg/mL, PMSF 1 mM, MgCl2 2 mM, lysozyme 50 µg/mL). The solution is incubated 30 min at 4° C. with agitation and then sonicated on ice/ethanol (4 steps of 7 min at 80% 0.5). DNase 1 mM is added and the solution is incubated one hour at 4° C. with agitation. The suspension is centrifuged at 40 000 g during 30 min at 4° C.

The pellet is resuspended in 7.5 mL/L of culture of a solubilization buffer (Tris 20 mM pH 7.5, NaCl 150 mM, urea 2M, SDS 1.5%, βmercaptoethanol 50 mM). The solution is incubated 2 hours at 8° C. with agitation.

The suspension is then centrifuged at 40 000 g during 30 min at 10° C.

Purification Method:

The urea supernatant is diluted 5 times in a buffer Tris 20 mM pH7.5, NaCl 150 mM, SDS 1.5%.

Purification is performed onto 1 mL/L of culture by affinity chromatography with Ni Sepharose Fast Flow column (Amersham BioScience). Supernatant is loaded at 2 mL/mn onto the resin after equilibration with a buffer Tris 20 mM pH7.5, NaCl 150 mM, urea 500 mM, SDS 1.5%, β-mercaptoethanol 10 mM. The elution of Env is performed by steps at 30 and 50 mM Imidazole.

The purification is performed with desalting column (Amersham BioScience, 25 mL of resin). The pool from the affinity chromatography is loaded at 2 mL/min onto the resin after equilibration with a buffer Tris 20 mM pH7.5, NaCl 150 mM, SDS 1.5%, DTT 10 mM. Proteins are eluted with the same buffer.

After that, proteins are loaded at 1 mL/min onto SUPERDEX 200 gel filtration (Amersham Bioscience) equilibrated with buffer Tris 20 mM pH7.5, NaCl 150 mM, SDS 1.5%, DTT 10 mM. Proteins are eluted with the same buffer.

Endotoxins removal:

The purification is performed with Acticlean column (Amersham Bioscience, 8 mL of resin). The pool is loaded at 1 mL/min onto the resin after equilibration with a buffer Tris 20 mM pH7.5, NaCl 150 mM, SDS 1.5%, DTT 10 mM. Proteins are eluted with the same buffer.

Quality controls of the batch

Mass spectrometry MALDI-TOFF: cannot be used because of the SDS.

N-Terminal sequencing: ALPYXTFLFT

Endotoxins assay: <5 UE/mL

Batch Characteristics:

Apparent solubility: 100%

Purity: >90%

Concentration: 0.05 mg/ml

Storage: −80° C.

Quantity: 1.5 mg

Buffer: Tris 20 mM pH 7.5, NaCl 150 mM, SDS 1.5%, DTT10 mM

Example 3

In Vitro Evidence of Ligand Binding Activity Specific for MSRV ENV Antigen

I—Objective

We have evaluated the affinity of the Ligand for the recombinant anti-Ligand under the form of an ScFv recombinant protein from cloned VH+VL sequences, or under the form of an Fab fragment cleaved from the original murine GNbAC1 (containing cleaved VH+VL chains devoid of murine antibody function and structure) by immunoassay techniques (ELISA). This Ligand was compared to the original murine GNbAC1, and to molecular constructs inserting the Ligand in human IgG1 or IgG4 constant chains and appropriate sequences for their use as pharmacological vectors.

II—Material and Methods a) VH and VL Cloning:

Cloning and Nucleotide Sequencing of GNb AC1 Variable Region of Light (VL) and Heavy (VH) Chains Poly(A+) RNAs were extracted and purified from $5 \times 10^7$ hybridoma cells producing GNb AC1 antibody using a mRNA purification kit (Amersham Bioscience) according to the manufacturer's instructions. Reverse transcription was performed from 800 ng mRNA using a RT-PCR kit (Amersham Bioscience) according to the manufacturer instructions.

The cDNA encoding variable region gene sequences of light (VL) and heavy (VH) chains was obtained using the rapid amplification of cDNA ends (RACE) method, as previously described (Ruberti et al., 1994, The use of the RACE method to clone hybridoma cDNA when V region primers fail. *J. Immunol. Methods* 173, 33-39). Forward primer was the following: RACE aller, (SEQ ID No. 21). Backward primers were the following: CL_Ala130_retour (SEQ ID No. 25) for VL amplification, and CH1_Pro119_retour (SEQ ID No. 26) for VH amplification, with the letter code R=A/G, K=G/T, H=A/T/C. Backward primers CL_Ala130_retour and CH1_Pro119_retour, deduced from consensus sequences published by Kabat et al. (1991, Sequences of proteins of immunological interest. National Institute of Health Bethesda, Md.), are specific of N-terminal extremities of mouse kappa/CL domain and IgG/CH1 domain, respectively.

PCR products were obtained using the Taq DNA polymerase and directly ligated into the pCR®2.1-TOPO® vector using a TA cloning kit (Invitrogen) according to the manufacturer instructions. The sequences of cloned DNAs were determined by sequencing on ABI310 automatic sequencer using a Dye Terminator Cycle Sequencing Ready Reaction Kit (Applied Biosystems).

b) ScFv Construction and Expression:

The ScFV was obtained according to techniques described in "Mallano A, et al. 2008, Generation and characterization of a human single-chain fragment variable (scFv) antibody against cytosine deaminase from Yeast. M. BMC Biotechnol. September 10; 8:68".

c) Fab from GNb AC1 Antibody

The Fab was obtained according to techniques described in "Lefranc G, Lefranc M P. Antibody engineering and perspectives in therapy. Biochimie. 1990 September; 72(9): 639-51.>>

II-1 Material

II-1a Monoclonal Antibodies

The Ligand, human IgG molecular constructs or GNbAC1 were produced and purified at the following concentrations:

TABLE 1 concentration of the different ligand, ScFV, Fab and antibodies

| Name | Concentration |
|---|---|
| GNbAC1 | 5.91/ml |
| Ligand in human IgG1 | 1 mgml |
| Ligand in human IgG4 | 2 mg/ml |

TABLE 1-continued concentration of the different ligand, ScFV, Fab and antibodies

| Name | Concentration |
|---|---|
| Murine Fab | 1 mg/ml |
| Recombinant ScFv | 1 mg/ml |

II-1b Recombinant Proteins

Both MSRV complete ENV protein (ENV-T) and surface domain fragment (ENV-SU) recombinant proteins, were produced by Protein Expert in *E. coli* and further purified as described in example 2.

TABLE 2 concentration of the recombinant proteins

| Protein Name | Concentration | Endotoxin |
|---|---|---|
| ENV-T | 0.15 mg/ml | <5 UI/ml |
| ENV-SU | 0.20 mg/ml | <5 UI/ml |

II-1c Sandwich ELISA

Microwells were washed 3 times with 250 µl per well of PBST 0.05% (Phosphate Buffer saline with 0.05% of TWEEN 20; Sigma P7949). After the last, plates were inverted and blotted on absorbent paper to remove any residual buffer.

Microwells were washed 3 times with 250 µl per well of PBST 0.05% (Phosphate Buffer saline with 0.05% of Tween20; Sigma P7949). After the last, plates were inverted and blotted on absorbent paper to remove any residual buffer.

200 µl per well of PBST 0.05%+5% milk were added. Plates were sealed and incubated 1 hour at AT under light agitation.

Microwells were washed 3 times with 250 microl per well of PBST 0.05%. After the last, plates were inverted and blotted on absorbent paper to remove any residual buffer.

Microwells were incubated with 100 µl per well of ENV antigen (ENV-T or ENV-SU) diluted in PBST 0.05%. Plates were sealed and incubated 2 hours at room temperature under light agitation.

Microwells were washed 3 times with 250 µl per well of PBST 0.05%. After the last, plates were inverted and blotted on absorbent paper to remove any residual buffer.

100 µl per well of detection antibody (GNbAC1 or recombinant fragment ScFv) diluted in PBST 0.05%+ 5% milk were added. Plates were sealed and incubated 1 hour at room temperature under light agitation. GNbAC1 was peroxydase labelled and ScFv biotin labelled by Squarix, Germany.

Microwells were washed 4 times with 250 µl per well of PBST 0.05%. After the last, plates were inverted and blotted on absorbent paper to remove any residual buffer.

100 µl par well of Substrate Solution (1 tablet of o-Phenylenediamine (OPD) diluted in 10 ml of 0.05M Phosphate Citrate Buffer pH5+10 µl $H_2O_2$ 30% (prepared at the last moment) were added. Plates were incubated 30 min at room temperature in the dark.

50 µl per well of Stop Solution 2N H2SO4 were added The absorbance was read at 490 nm within 30 minutes of stopping reaction.

II-1d Direct ELISA on Microplates Coated with ENV Antigen (ENV-T or ENV-SU as Described Above)

Microwells were coated with 100 µl per well of ENV antigen diluted in 50 mM Sodium Bicarbonate, pH 9.6. Plate were sealed and incubated 2 hours at 37° C. under light agitation.

Microwells were washed 4 times with 250 µl per well of PBS (Phosphate Buffer Saline). After the last, plates were inverted and blotted on absorbent paper to remove any residual buffer.

100 µl per well of detection antibody according to the present invention (GNbAC1 or its Fab fragment) diluted in PBS+BSA 1% (PBS with 1% of Bovine Serum Albumin) were added. Plate were sealed and incubated 1 hour at room temperature under light agitation.

Microwells were washed 4 times with 250 µl per well of PBS. After the last, plates were inverted and blotted on absorbent paper to remove any residual buffer.

100 µl per well of secondary detection antibody diluted in PBS+BSA 1% (anti IgG Jackson—diluted 1/250; either, IgG anti human perox Jackson 115-035-146 or, IgG anti mouse perox Jackson 115-035-062, in adequacy with the primary antibody) were added. Plate were sealed and incubated 1 hour at room temperature under light agitation.

Microwells were washed 6 times with 250 µl per well of PBS. After the last, plates were inverted and blotted on absorbent paper to remove any residual buffer.

100 µl par well of Substrate Solution (1 tablet of o-Phenylenediamine (OPD) diluted in 10 ml of 0.05M Phosphate Citrate Buffer pH5+10 µl H2O2 30%, prepared at the last moment) were added. Plates were incubated 30 min at room temperature in the dark.

50 µl per well of Stop Solution 2N $H_2SO_4$ were added. The absorbance was read at 490 nm within 30 minutes of stopping reaction.

III—Results

III-1 Sandwich ELISA: Murine IgG1 (GNbAC1) and ScFv

TABLE 3

Concentrations of coating antibody versus Peroxydase or Biotin detection Ligand for each concentration of antigen or control buffer.

| | 3C1D5 lot 060405CS02 IgG1GNbAC1 peroxydase Labelled | 3C1D5 lot 060405CS02 ScFvbiotine Labelled |
|---|---|---|
| Env SU 0.5 µg/ml | 2.695 | 1.289 |
| Env SU 0.1 µg/ml | 1.036 | 0.656 |
| Env SU 0.02 µg/ml | 0.294 | 0.455 |
| PBST 0.05% | 0.101 | 0.411 |
| Env T 0.5 µg/ml | 1.807 | 1.085 |
| Env T 0.1 µg/ml | 0.862 | 0.594 |
| Env T 0.02 µg/ml | 0.215 | 0.443 |
| PBST 0.05% | 0.143 | 0.420 |

Results correspond to measured optic densities.
PBST: Phosphate Buffer Saline with 0.05% TWEEN 20

Figure 3:
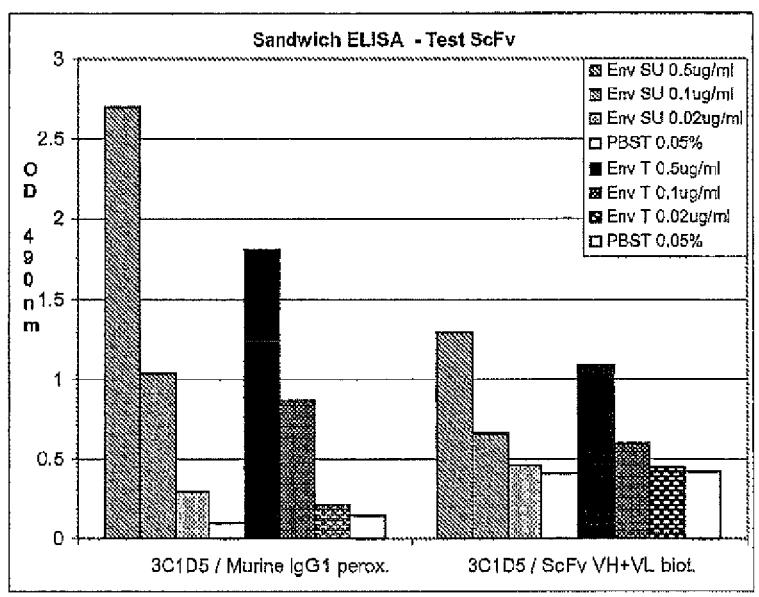

The results with the ELISA performed in parallel with the ScFv and the original GNbAC1 are presented with different conditions in FIG. 3.

The concentration of the coating antibody and detection Ligand was 5 µg/ml each; streptavidin-peroxidase conjugate dilution was 1/2000.

We analyzed GNbAC1 and the recombinant ScFv as detection Ligands in a sandwich ELISA against the ENV-SU and ENV-T recombinant proteins. As we can see in FIG. 3, at the same concentration, the MAb and the ScFv are able to detect the ENV proteins, with an OD over one-half of the IgG for the ScFv, when the IgG is divalent and the ScFv is monovalent. Therefore, relatively to the number of binding sites per molecule, the isolated Ligand has yielded better results than the complete murine IgG. Thus, antibody functions are not necessary and such improved results with the isolated Ligand were unexpected.

III-2 Direct ELISA: GNb Ac1 and Fab

TABLE 4

Concentrations of coating antibody versus Peroxydase-labeled detection Ligands (direct labelling) for each concentration of antigen or control buffer.

|  | Fab: 100 µg/ml | GNb Ac1: 10 µg/ml |
|---|---|---|
| Env T 0.5 µg/ml | 2.83 | 3.00 |
| Env T 0.25 µg/ml | 1.85 | 2.75 |
| Env 0.125 µg/ml | 1.19 | 8 |
| Env T 0.0625 µg/ml | 0.77 | NA |
| Env T 0.013125 µg/ml | 0.56 | 0.51 |
| Env T 0.015625 µg/ml | 0.56 | 0.37 |
| Env T 0.0078125 µg/ml | 0.48 | 0.26 |

Results correspond to measured optic densities.
NA: Not Applicable measure (technical troubleshooting).

Figure 4:
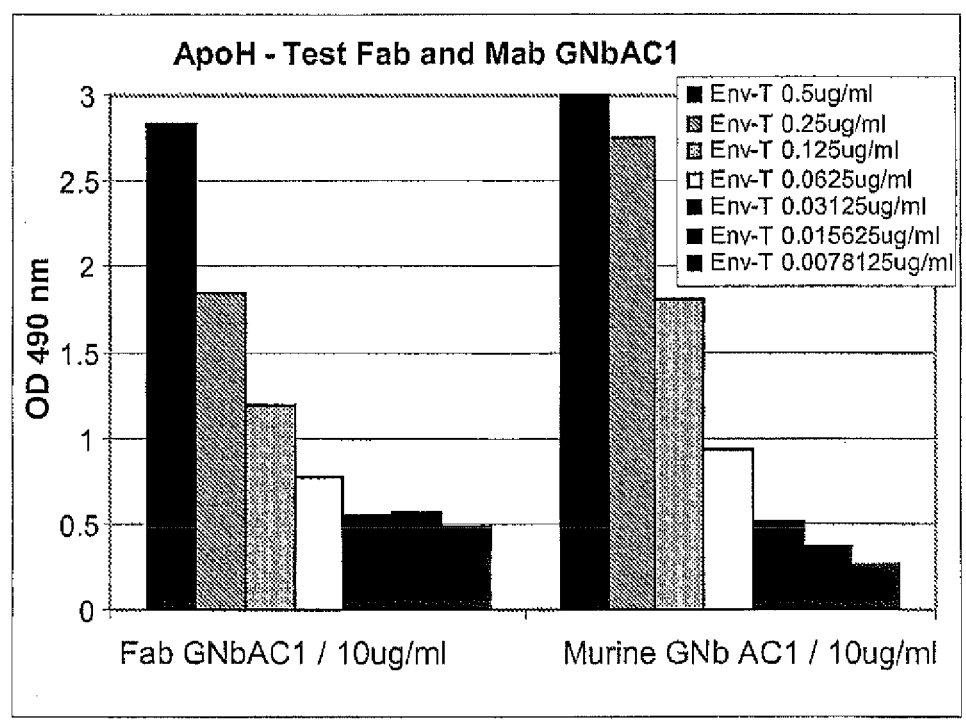

We analyzed the murine IgG1 and its Fab fragment as detection Ligands in a sandwich ELISA against the ENV-T recombinant protein. As we can see in FIG. 4, at the same concentration, the monovalent Fab detects the ENV protein with an optic density superior or equal to the divalent IgG. Here again, we see that the isolated Ligand surprisingly yields better results than the complete IgG.

We can thus conclude that, repeatedly, the antibody functions were not necessary and that the Ligand itself is more efficient than the "natural" murine IgG.

Example 4

Design, Construction and In Vitro Analysis of Molecular Constructs with Human IgG1 and IgG4 Constant Chains and Ligand After having evidenced the unexpected improved performance of the isolated Ligand comprising monovalent binding sites with either natural (Fab) or recombinant (scFv) VH and VL sequences in immunoassay detection of the target antigen, we have designed and constructed recombinant sequences for the production of chimeric human IgG1 or IgG4 molecules comprising the Ligand sequences (VH+VL). Thus, we have produced complete antibodies as molecular vectors for the Ligand and evaluated them by immunoassays in comparison with the original murine IgG.

In order to produce these recombinant antibody vectors with the inserted Ligand, clones were adapted for their expression in CHO cells and antibodies were produced and purified by "Polymmun", Vienna, Austria. The technical conditions for the productions of these antibodies with appropriate vectors are summarized below:

Establishing of the Recombinant CHO Cell Lines GNbAC1_IgG1 and GNbAC1_IgG4

This section describes the source of genes of the recombinant monoclonal antibody GNb AC1 expressed recombinantly as chimeric human/mouse IgG1 and IgG4, whereby the constant regions are human and the variable regions are the original VH and VL sequences as described in SEQ ID No.8 and SEQ ID No.7 respectively Expression Plasmids Chimeric GNb AC1 IgG1 Light Chains (LC)

Basically, this expression plasmid is the commercially available pCIneo (Promega), which was used in the first step to insert the codon optimised (optimisation of codon usage for expression in CHO cells, designed by GENEART, also including optimisation of the mRNA structure) human kappa light chain backbone including an immunoglobulin kappa signal sequenced and the human c-kappa-constant region with intermediate restriction sites to insert any variable light chain region. According to the primary sequence of VL (SEQ ID No.7) a synthetic nucleotide insert was synthesized at GENEART AG (Regensburg, Germany) including restriction sites in the 3' end of the signal sequence and in the 5' site of the kappa light chain region to insert the optimised variable region—VL codons—(SEQ ID No.27) into the BsiWI und AccIII opened eukaryotic expression vector carrying the codon optimised human kappa light chain backbone—IgG1L codons—under control of the CMV promoter. Additionally, the vector contains the neomycin phosphotransferase for selection of CHO cells with G418. SEQ ID No.28 indicates the nucleotide sequence of the construct associating optimised "IgG1L codons and VL codons" used for expression into CHO cells.

Chimeric GNb AC1 IgG1 Heavy Chains (HC)

The cloning vector for generation of the GNb AC1 IgG1 eukaryotic expression vector consists of two eukaryotic expression cassettes with identical regulatory regions. This vector already contains a codon optimised (optimisation of codon usage for expression in CHO cells, designed by GENEART, also including optimisation of the mRNA structure) human IgG1 backbone including the signal region of an immunoglobulin heavy chain and the human IgG1 constant region with intermediate restriction sites to insert any variable heavy chain region.

The information for the amino-acid sequence of the variable region (VH) of the mouse monoclonal antibody GNb AC1 is presented in SEQID No. 8. According to that primary sequence a synthetic nucleotide insert was synthesized at GENEART including restriction sites (in the 3' end of the signal sequence and in the 5' site of the gamma chain CH1 region, to insert the optimised variable heavy region (SEQ ID No.29)—VH codons—into the AgeI und NheI opened eukaryotic expression vector carrying codon optimised human IgG1 backbone under control of the SV40 promoter. Additionally, the vector contains the mouse dihydrofolate reductase as second expression cassette for use as selection/amplification marker in animal cell culture. SEQ ID No.30 represents the nucleotide sequence of the construct associating optimised human IgG1H-backbone codons and optimised VH codons" used for expression into CHO cells.

Chimeric GNb AC1 IgG4 Heavy Chain (HC)

The cloning vector for generation of the GNb AC1 IgG4 eukaryotic expression vector consists of two expression cassettes with the identical regulatory regions and is the same as for the IgG1 construct.

However, since no human IgG4 constant region was available the whole heavy chain including the signal sequence, the mouse GNb AC1 variable Heavy (VH) region and the human IgG4 constant region was synthesised by GENEART.

SEQ ID No. 31 shows the nucleotide sequence of the coding region of the chimeric GNb AC1 IgG4 optimised heavy chain (IgG4H codons). Afterwards, the insert was introduced into the NotI und SacII opened eukaryotic expression vector resulting in the construct, shown in SEQ ID No.32, which associates the optimised IgG4H codons and the optimised VH codons used for expression into CHO cells.

All plasmids were cloned at GENEART and afterwards transformed into E. coli strain TOP10 The recombinant bacteria were propagated in 50 ml LB/Amp-medium and plasmids were isolated with the Promega PureYield™ Plasmid Midiprep Systems. Yield and purity of plasmids were controlled photometrically with and quotient of optical density at 260 nm and 280 nm, determined to be at least 1.5.

Establishing of the Recombinant Cho Cell Lines GNb AC1_IgG1 and GNb AC1_IgG4

Transfection Procedure

Dihydrofolate reductase deficient Chinese Hamster Ovary Cells (referred to as CHO dhfr−, ATCC no. CRL 9096) were chosen as the parental cell line for the generation of the final expression line. These cells—originating from the American Type Culture Collection (ATCC)—were propagated in "cultivation medium" consisting of DMEM supplemented with 4 mM L-glutamine, 0.1 mM hypoxanthine, 0.016 mM thymidine (HT), 0.25 g/l soy peptone, 0.1% Pluronic F-68 and protein-free supplement (Polymun Scientific) with a splitting ratio 1:6 twice a week.

$5 \times 10^6$ cells washed once with basal medium and resuspended in 10 ml complete medium were used for transfection. Polyplexes were formed by incubation of 900 µl of polyethylenimine (1 mg/ml PEI linear, MW: 25,000, Polysciences Inc.) with 12 µg HC and 12 µg LC plasmid in a total volume of 2 ml for 30 minutes at RT. Interaction of polyplexes with CHO cells in 12 ml lasted for four hours before centrifugation at 170 g, discarding the supernatant and resuspending the cells in "cultivation medium". After 24 hours, the complete medium was replaced by 50 ml selection medium composed of DMEM supplemented with 4 mM L-glutamine, 0.25 g/l soy peptone, 0.1% Pluronic F-68, protein-free supplement (Polymun Scientific) and 0.5 µg/ml G418. 100 µl of the cell suspension were seeded per well in five 96-well plates. 4 Transfection experiments ("IgG1H codons+VH codons" construct co-transfected with "IgGiL codons+VL codons" for Chimeric GNbAC1-IgG1; "IgG4H codons+VH codons" construct co-transfected with "IgG1L codons+VL codons" for Chimeric GNbAC1-IgG4) generated a total of 20×96 well plates (corresponding to 1920 wells) per IgG subtype.

After 10 to 14 days, formed clones were fed with 100 µl of "amplification medium" consisting of 0.048 µM MTX in selection medium. Growing clones were fed with another 100 µl of amplification medium again containing 0.048 µM MTX and afterwards analysed in a double sandwich ELISA. The ELISA used anti human gamma specific polyclonal serum for coating and anti human kappa chain HRP coupled polyclonal antibody for detection.

Selected high producer clones were adapted to 0.19 µM MTX in selection medium.

Table 5 describes the selection for best producers of GNb AC1 IgG1 and GNb AC1 IgG4 at 0.096 and 0.19 µM MTX in T25 Roux flasks and Spinner vessels.

In case of GNb AC1_IgG1 we decided for clone 6B6 and in case of GNb AC1_IgG4 we decided for clone 7C1. In case of GNb AC1_IgG1 cryopreservation of three clones, GNb AC1_IgG1_6B6, GNb AC1_IgG1_8H2 and GNb AC1_IgG1_18A8 and in case of GNb AC1-IgG4 cryopreservation of two clones, GNb AC1_IgG4_6C1 and GNb AC1_gG4_7C1 was done. The best clone was subcloned by limiting dilution method as, e.g., described in "Molecular Cloning: A Laboratory Manual (Third Edition) Joseph Sambrook, Peter MacCallum Cancer Institute, Melbourne, Australia; David Russell, Cold Spring Harbour Laboratory Books".

Subcloning of Best Producing Transfectants GNb AC1_IgG1_6B6 and GNb AC1_IgG4_7C1

Subcloning was performed in 96-well plates with 90, 30 and 10 cells per well in amplification medium with, in case of GNb AC1_IgG1_6B6: 0.19 µM Methotrexate (Sigma, MTX) and 50% GNb AC1_IgG1_6B6 culture supernatant 0.2 µm filtered, in case of GNb AC1_IgG4_7C1: 0.19 µM MTX and 50% GNb AC1_IgG4_7C1 culture supernatant 0.2 µm filtererd. Growing wells were adapted to 0.38 µM MTX in 96-well plates, analysed by ELISA and propagated in T25 flasks for further screening and adaptation to 0.77 µM MTX.

Table 6 describes the selection for best producers of GNb AC1 IgG1_6B6- and GNb AC1 IgG4_7C1-subclones at 0.77 µM MTX in T25 Roux flasks and Spinner vessels.

The best producer in case of GNb AC1_IgG1_6B6 was clone GNb AC1_IgG1_6B6_10E4 and in case of GNb AC1_IgG4_7C1 clone GNb AC1_IgG4_7C1_15B7. These two clones were chosen for further cell line development.

Cryopreservation of two GNb AC1-IgG1 clones: GNb AC1-IgG1_6B6_1D1, GNb AC_IgG1_6B6_10E4 and two GNb AC1-IgG4 clones: GNb AC1-IgG4_7C1_3E11, GNb AC1-IgG4_7C1_15B7 was done.

Subcloning of Best Producing Subclones GNb AC1-IgG1_6B6_10E4 and GNb AC1-IgG4_7C1_15B7

A final subcloning procedure was performed again in 96 well plates with 90, 30 and 10 cells per well in amplification medium in case of GNb AC1_IgG1_6B6_10E4 with 0.77 µM MTX and 50% GNb AC1_IgG1_6B6_10E4 culture supernatant 0.2 µm filtered, in case of GNb AC1_IgG4_7C1_15B7 with 0.77 µM MTX and 50% GNb AC1_IgG4_7C1_15B7 culture supernatant 0.2 µm filtered. Growing wells were analysed by ELSA, best producers were propagated to T25 flasks and spinner flasks (Sp125) for further screening.

Table 7 describes the selection for best producers of GNb AC1 IgG1_6B6_10E4- and GNb AC1 IgG4_7C1_15B7-subclones at 0.77 µM MTX in T25 Roux flasks and spinner flasks.

In case of GNb AC1_IgG1 two clones GNb AC1_IgG1_6B6_10E4_18C7 and GNb AC1_IgG1_6B6_10E4_18D12, in case of GNb AC1_IgG4 two clones GNb AC1_IgG4_7C1_15B7_3E4 and GNb AC1_IgG4_7C1_15B7_5G10 were cryo preserved after from spinner cultures.

TABLE 5 selected wells after transfection and adaptation to different levels of MTX

| | cell count E+05 c/ml | titre µg/ml | days | spec. titre pg/c*d$^£$ |
|---|---|---|---|---|
| GNb AC1-IgG1: 0.096 µM MTX: | | | | |
| In T25: | | | | |
| 6B6 | 6.9 | 14.2 | 4 | 5.2 |
| 8H2 | 5.6 | 4.0 | 3 | 2.3 |
| 18A8 | 3.8 | 3.3 | 3 | 2.9 |
| In Sp125 | | | | |
| 6B6 | 2.6 | 11.5 | 4 | 11.3 |
| 8H2 | 5.0 | 3.5 | 3 | 3.1 |
| 18A8 | 4.2 | 4.0 | 3 | 2.4 |

TABLE 5-continued selected wells after transfection and adaptation to different levels of MTX after adaptation to 0.19 µM MTX:

| In T25: | | | | |
|---|---|---|---|---|
| 6B6 | 5.3 | 7.4 | 3 | 4.7 |
| 8H2 | 4.2 | 4.0 | 3 | 3.2 |
| 18A8 | 5.5 | 3.4 | 3 | 2.0 |

| | cell count E+05 c/ml | titre µg/ml | days | Spec. titre [pg/c*d] |
|---|---|---|---|---|
| GNb AC1-IgG4: 0.096 µM MTX: | | | | |
| In T25: | | | | |
| 61C | 4.1 | 9.6 | 3 | 7.9 |
| 7C1 | 2.3 | 3.7 | 3 | 5.4 |
| In Sp125: | | | | |
| 6C1 | 5.5 | 14.3 | 3 | 8.6 |
| 7C1 | 4.5 | 10.9 | 3 | 8.2 |
| after adaptation to 0.19 µM MTX: | | | | |
| In T25: | | | | |
| 6C1 | 3.6 | 11.8 | 3 | 10.8 |
| 7C1 | 4.7 | 12.5 | 3 | 8.8 |

£picogram per cell and day.
*Picogram/cell

TABLE 6 selected subclones after first subcloning at 0.77 µM MTX

| | cell count E+05 c/ml | titre µg/ml | days | Spec. titre [pg/c*d] |
|---|---|---|---|---|
| GNb AC1-IgG1: | | | | |
| In T25: | | | | |
| GNb AC1-IgG1_6B6_1D1 | 4.8 | 23.4 | 4 | 12.1 |
| GNb AC1-IgG1_6B6-10E4 | 3.4 | 11.9 | 3 | 11.8 |
| In Sp125: | | | | |
| GNb AC1-IgG1_6B6_1D1 | 4.0 | 12.9 | 3 | 10.8 |
| GNb AC1-IgG1_6B6-10E4 | 3.5 | 10.9 | 3 | 10.4 |
| GNb AC1-IgG4: | | | | |
| In T25: | | | | |
| GNb AC1-IgG1_7C1_3E11 | 3.8 | 7.8 | 3 | 7.0 |
| GNb AC1-IgG4_7C1_15B7 | 3.1 | 11.5 | 4 | 9.3 |
| In Sp125: | | | | |
| GNb AC1-IgG1_7C1_3E11 | 5.1 | 16.7 | 3 | 10.9 |
| GNb AC1-IgG4_7C1_15B7 | 4.5 | 14.7 | 3 | 11.0 |

TABLE 7

Selected subclones after second (final) subcloning at 0.77 µM MTX:

| | cell count E+05 c/ml | titre µg/ml | days | Spec. titre [pg/c*d] |
|---|---|---|---|---|
| GNb AC1-IgG1: | | | | |
| GNb AC1-IgG1_6B6_10$^E$4_ . . . : | | | | |
| In T25: | | | | |
| 18C7 | 7.2 | 18.5 | 4 | 6.4 |
| 18D12 | 9.6 | 18.4 | 4 | 4.8 |
| In Sp125: | | | | |
| 18C7 (160608) | 4.1 | 21.6 | 4 | 13.3 |
| 18D12 (160608) | 4.0 | 15.0 | 4 | 9.5 |
| 18C7 (190608) | 6.2 | 20.9 | 3 | 11.3 |
| 18D12 (190608) | 6.5 | 15.7 | 3 | 8.1 |
| 18C7 (230608) | 4.7 | 20.9 | 4 | 11.1 |
| 18D12 (230608) | 5.3 | 18.6 | 4 | 8.7 |
| 18C7 (260608) | 2.7 | 11.2 | 3 | 13.8 |
| 18D12 (260608) | 3.5 | 10.6 | 3 | 10.1 |
| GNb AC1-IgG4: | | | | |
| GNb AC1-IgG4_7C1_15B7_ . . . : | | | | |
| In T25: | | | | |
| 3E4 | 4.1 | 25.6 | 4 | 15.6 |
| 5G10 | 5.2 | 30.5 | 4 | 14.8 |
| In Sp125: | | | | |
| 3E4 (160608) | 3.0 | 20.0 | 4 | 16.6 |
| 5G10 (160608) | 3.4 | 20.2 | 4 | 14.7 |
| 3E4 (190608) | 4.3 | 20.9 | 3 | 16.2 |
| 5G10 (190608) | 4.2 | 23.2 | 3 | 18.5 |
| 3E4 (230608) | 3.3 | 20.8 | 4 | 15.9 |
| 5G10 (230608) | 3.0 | 21.4 | 4 | 18.1 |
| 3E4 (260608) | 2.5 | 16.7 | 3 | 22.1 |
| 5G10 (260608) | 2.6 | 16.4 | 3 | 21.3 |

Recombinant IgG1 AND IgG4 antibody vectors were thus produced with inserted Ligand comprising the six CDR sequences as described in example 1. These vectors comprising the six CDRs are analysed the following example, in order to determine the positive and negative influence of the vectors and, thus propose a selection and/or and adequate use for each of them.

Example 5

Study of the Ligand and of its Human IgG1 and IgG4 Chimeric Constructs, Versus the Original Murine IgG1: In Vitro Affinity Material and methods were the same as described in examples 3 and 4.

5.a. ELISA with Different Concentrations of MSRV-ENV Complete Protein (ENV-T)

TABLE 8

Optical densities (OD) measured by ELISA with different ligands (1 microgram) or irrelevant control (2G5E12) on different concentrations (left column, in micrograms) of anti-Ligand (ENV-T) coated onto microtiter plate wells.

| [ENV-T 7A] | GNbAC1 chimeric IgG1 lot2 | GNbAC1 chimeric IgC4 lot 2 | GNbAC1 Murine 060413CS01 | 2G5E12 Murine 010227FP01 |
|---|---|---|---|---|
| | 3 | 3 | 2.998 | 0.082 |
| 0.5 | 3 | 2.889 | 2.899 | 0.12 |

TABLE 8-continued

Optical densities (OD) measured by ELISA with different ligands (1 microgram) or irrelevant control (2G5E12) on different concentrations (left column, in micrograms) of anti-Ligand (ENV-T) coated onto microtiter plate wells.

| [ENV-T 7A] | GNbAC1 chimeric IgG1 lot2 | GNbAC1 chimeric IgC4 lot 2 | GNbAC1 Murine 060413CS01 | 2G5E12 Murine 010227FP01 |
|---|---|---|---|---|
| 0.25 | 2.891 | 2.524 | 2.837 | 0.093 |
| 0.125 | 2.393 | 1.985 | 2.285 | 0.111 |
| 0.0625 | 1.804 | 1.522 | 1.565 | 0.092 |
| 0.03125 | 1.562 | 1.367 | 1.341 | 0.066 |
| 0.0156 | 1.257 | 1.021 | 1.299 | 0.125 |
| 0.0078 | 0.815 | 0.692 | 0.625 | 0.114 |

Binding is revealed with peroxydase labeled anti-Ig antibody (1/250; Jackson-USA) and peroxydase substrate reaction. The average value of all OD from the irrelevant control is 0.1004 and their standard deviation (SD) is 0.0205, therefore a cut-of value can be determined, below which all values are non-specific with 99% confidence interval: average + 3*SD = 0.1618. All presented values with GNb AC1 constructs are therefore significant of a specific binding to the target protein.

Figure 5:
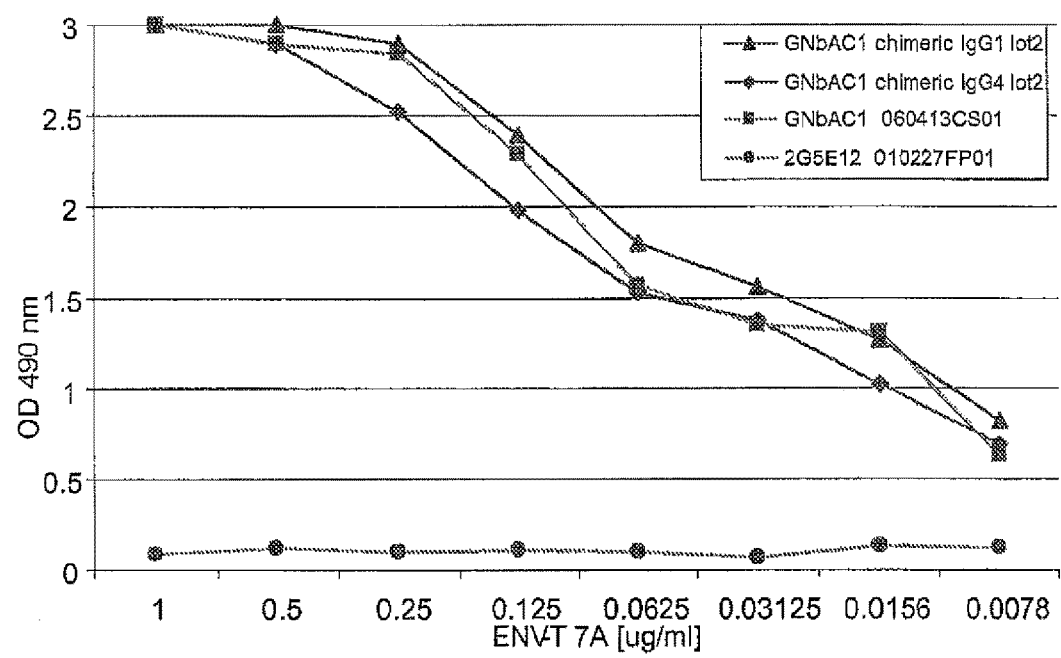

We analyzed antibody GNbAC1 and the chimeric version IgG1 and IgG4 as detection antibodies in a sandwich ELISA against the ENV recombinant protein. As we can see in FIG. 5 and Table 8, at the same concentration, the murine and chimeric MAbs are able to detect present concentrations of ENV proteins, with similar kinetics. The specificity and relative affinity of the new constructs (ligand in a human vector) are thus maintained and, both human IgG1 and IgG4 constructs with the Ligand have provided human chimeric antibodies able to detect picograms of the recombinant ENV protein. This is surprisingly good and confirms the optimization achieved throughout their whole design, construction and expression conditions. It also validates the selection of a stable and robust Ligand structure, as described in example 1.

Moreover, this experience provides a means to identify molecules equivalent to the Ligand through the significance of their binding between and the original anti-Ligand (ENV), as evidenced here with the Ligand (GNb AC1) versus an irrelevant "non-binding" ligand (2G5E12):

Env-T antigen is coated onto microtiter ELISA plate wells with serial dilutions ranging from 1 µg/ml to about 0.01 µg/ml.

The reference Ligand (GNbAC1) and an irrelevant ligand (2G5E12) are tested at 1 µg/ml and are revealed with a secondary antibody (here, anti-IgG peroxidase-labeled secondary antibody from Jackson Ltd, USA, diluted 1/250, hereafter referenced as anti mouse IgG (H+L) Jackson or anti human IgG; Jackson, USA).

The curve with the reference Ligand shows saturation of signal (optical density superior or equal to 3) at the highest ENV concentration and progressively decreases down to an optical density about 1.0-0.5, thus evidencing a dose-response curve typical of specific binding activity (above the calculated statistical cut-off value of 0.1618; see Table 8). In parallel, the irrelevant molecule (2G5E12), shows no dose-response curve (flat average curve) and oscillates between an optical density of 0.1 and 0.05 at any ENV concentration, below the calculated statistical cut-off value of 0.1618 (Table 8).

Thus, any molecule equivalent to the Ligand can thus be evidenced by either,

1) The existence of a dose-response-curve in this test, with the conditions of the present example, as shown in paragraph 5a, and 2) The absence of a flat curve, oscillating below a statistical cut-off calculated (Average+three standard deviations) from optical density values obtained with an irrelevant antibody (Cf. 2G5E12 in Table 8), compared to values above the cut-off obtained with reference GNbAC1 for an ENV concentration of 0.01 microgram (see Table 8);

or,

3) The existence of a dose-response-curve in a test as described below with Ligand serial dilutions and a fixed anti-Ligand concentration, in paragraph 5b (Table 9), and 4) The absence of a flat curve, oscillating below a statistical cut-off calculated (Average+three standard deviations) from optical density values obtained with an irrelevant antibody (Cf. 2G5E12 in Table 9), compared to values above the cut-off obtained with corresponding reference GNbAC1 at a concentration of 0.01 microgram/ml, in the same conditions as described in paragraph 5b (see Table 9).

5.b ELISA with Different MAbs Concentration

TABLE 9

Optical densities measured by ELISA with serial dilutions of the ligand and a fixed anti-Ligand concentration. (ENV-T; 0.01 microgramm) coated onto microtiter plate wells. Binding is revealed with peroxydase labeled anti-IgG antibody (1/250; Jackson-USA) and peroxydase substrate reaction.

| | | Anti-mouse IgG (H + L) Jackson 1/250 | | | | Anti human IgG Jackson 1/250 | | |
|---|---|---|---|---|---|---|---|---|
| Concentration | GNbAC1 murine | 2G5E12 | GNbAC1-IgG1 | GNbAC1-IgC4 | Buffer control | 2G5E12 | GNbAC1-IgG1 | GNbAC1-IgC4 |
| 1 | 2.065 | 0.077 | 0.738 | 0.753 | 0.05 | 0.046 | 1.78 | 1.696 |
| 0.5 | 1.926 | 0.085 | 0.586 | 0.43 | 0.047 | 0.056 | 1.724 | 1.741 |
| 0.25 | 2.149 | 0.069 | 0.365 | 0.374 | 0.046 | 0.049 | 1.535 | 1.499 |
| 0.125 | 2.029 | 0.071 | 0.221 | 0.238 | 0.048 | 0.046 | 1.544 | 1.248 |
| 0.0625 | 1.965 | 0.074 | 0.221 | 0.189 | 0.047 | 0.045 | 1.205 | 1.154 |
| 0.03125 | 1.728 | 0.074 | 0.171 | 0.156 | 0.047 | 0.047 | 0.906 | 0.929 |
| 0.0156 | 1.681 | 0.066 | 0.093 | 0.105 | 0.051 | 0.048 | 0.55 | 0.511 |
| 0.0078 | 0.964 | 0.072 | 0.073 | 0.087 | 0.061 | 0.073 | 0.276 | 0.372 |

With anti-mouse secondary antibody detection, the average value of all OD from the irrelevant control is 0.0735 and their standard deviation (SD) is 0.0057, therefore a cut-of value can be determined, below which all values are non-specific with 99% confidence interval: average+ 3*SD=0.0907. All presented values with corresponding murine GNb AC1 are therefore significant of a specific binding to the target protein.

With anti-human secondary antibody detection, the average value of all OD from the irrelevant control is 0.0513 and their standard deviation (SD) is 0.0094, therefore a cut-of value can be determined, below which all values are non-specific with 99% confidence interval: average+ 3*SD=0.0796. All presented values with GNb AC1 Chimeric constructs are therefore significant of a specific binding to the target protein.

Figure 6:
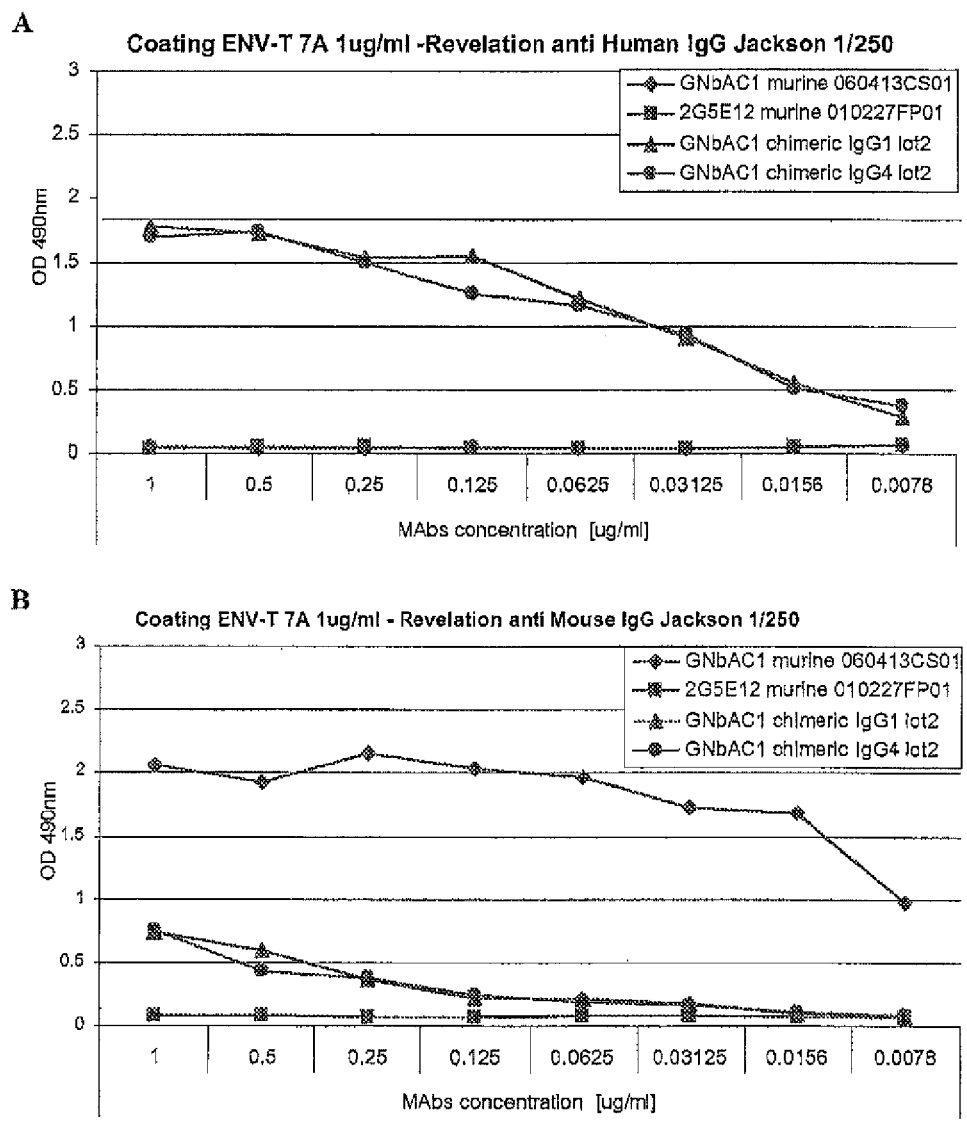

In FIG. 6, we can see that both murine IgG antibody GNbAC1 and chimeric versions IgG1 and IgG4 are efficient as detection antibodies in a sandwich ELISA against the ENV-T recombinant protein, with quantities as low as few nanograms of purified IgG for detecting less than few nanograms of ENV protein.

In addition, since the anti-human or mouse IgG did not cross-react with either the original murine antibody or the chimeric constructs with the human IgG1 or IgG4 backbones, the inserted Ligand (VH+VL) has not created any unwanted modification and is not detected in the human constructs, in these conditions.

5c: Affinity of the GNbAC1 to ENV-T

TABLE 10 determination of the binding affinity of the Ligand inserted in IgG4 and IgG1 antibody vectors (the units are indicated in the table)

|  | ENV-T at half of mAb det. [mg/l] | Env-concentration [M] | Affinity [M] | MM His-ENV-T [g/mole] |
|---|---|---|---|---|
| IgG1 | 0.25 | 1.07E−09 | 2.46E+08 | 61.440 |
| IgG4 | 0.35 | 5.70E−09 | 1.76E+08 | |

5.d: GNbAC1 Isoelectric Point

GNbAC1 isoelectric point was determined according to techniques described in <<Fractionation of complex protein mixtures by liquid-phase isoelectric focusing. Hey J, Posch A, Cohen A, Liu N, Harbers A. Methods Mol Biol. 2008; 424:225-39.>>.

The isoelectric point of the constructions IgG1 (pI 8.3) and IgG4 (pI 7.53) are very useful and will determine the stability and storage conditions for a therapeutic use. The neutral pI of the IgG4 is thus better for the formulation of a therapeutic MAb which can be as a chronic treatment with regularly repeated injections. Thus, the IgG4 is a favored construct from this point.

Example 6

Study of the Ligand and of its Human IgG1 and IgG4 Constructs, Versus GNbAC1: Inhibitory Activity on Pro-Inflammatory Cytokines in Human Peripheral Blood Mononuclear Cell (PBMC) Cultures Materials and Methods:
Culture Medium
The PBMCs were cultivated in RPMI Glutamax (Gibco)+ 10% FBS (Biowest S1810 South America)+1% non essential amino acids+1% pyruvate+1% penicillin-streptomycin, at 37° C. under 6.5% $CO_2$.
PBMCs Preparation from Buffy Coats
The Buffy coats are provided by the HUG.
The blood, diluted with PBS-FBS 2% (4 ml+31 ml), is smoothly put on 15 ml of Ficoll and centrifuged at 2850 rpm (1650 g)/20 min/room temperature/without break.
The PBMCs are then carefully collected and washed 3 times with PBS-SVF 2% and centrifuged at 1500 rpm/10 min.
The cells are then counted and frozen in SVF 90%+ DMSO 10%.
PBMCs Preparation from Frozen Cells
PBMCs kept at −80° C. are thawed at 37° C., washed 3 times with the medium and centrifuged at 1500 rpm/10 min.
The cells are then counted and diluted to a concentration of usually $1 \times 10^6$ cells/mi.
Inhibition Test
The ENV+MAbs mix is prepared before the PBMCs are thawed. The MAbs (Ratio chosen with ENV)+ENV (chosen concentration) are mixed in each well of 48 wells plates, in 100 ul of medium and incubated 1 hour at +4° C.
The PBMCs are then added in each well, for a final concentration of $1 \times 10^6$ cells/ml (0.5 ml or 1 ml final per well).
The cells are incubated 24, 48 or 72 hours at 37° C., 5% $CO_2$.
The supernatants are collected by centrifugation at 1400 rpm/10 min/RT and kept at −20° C.
Il-2d Cytokines Dosage
The cytokines are dosed with BD Pharmingen ELISA sets, for IL-6, IL-12p40, TNF-α and IFN-γ. The protocol of the supplier was followed.

TABLE 11 cytokine dosage in different PBMC (Peripheral Blood Mononuclear cells) culture supernatants with or without different ligands.

| Lot ENV | MAbs | Ratio MAbs/ENV-T | IL-6 pg/ml | Response (%) | Inhibition (%) | IFN-□ pg/ml 72 h | Response (%) | Inhibition (%) |
|---|---|---|---|---|---|---|---|---|
| ENV-SU4A 0.5 ug/ml | No Mabs | — | 88742 | 100 | — | 558 | 100 | — |
| | GNb AC1 murine IgG1 | 25/1 | 42250 | 48 | 52 | 270 | 48 | 52 |
| | GNb AC1 ScFv Chimeric Human | 25/1 | 56675 | 64 | 36 | 661 | 118 | −18 |
| | GNb AC1 IgG1 2008 | 25/1 | 32871 | 37 | 63 | 606 | 109 | −9 |

TABLE 11-continued cytokine dosage in different PBMC (Peripheral Blood Mononuclear cells) culture supernatants with or without different ligands.

| Lot ENV | MAbs | Ratio MAbs/ENV-T | IL-6 | | | IFN-☐ | | |
| --- | --- | --- | --- | --- | --- | --- | --- | --- |
| | | | pg/ml | Response (%) | Inhibition (%) | pg/ml | Response (%) | Inhibition (%) |
| | | | | | 72 h | | | |
| | GNb AC1 IgG4 2008 | 25/1 | 52954 | 60 | 40 | 318 | 57 | 43 |

We tested with cellular tests on PBMCs the potential of our antibodies or ScFv to inhibit the interaction between the ENV protein and the cells (via the TLR4 receptor), and thus the production of pro-inflammatory cytokines such as IL-6 (innate immunity) and IFN-γ (T-lymphocyte mediated immunity). The different molecules were tested at the same ratio (mol/mol) with the protein (25/1) so that we can compare their performance.

As can be seen in FIG. 7 and Table 11, all the Ligand molecules, either being of murine or recombinant origin (scFv or IgG1 and IgG4 constructions with the Ligand), have and keep their inhibitory properties, as represented by the reduction of pro-inflammatory cytokines (IL-6) produced by the PBMCs.

Nonetheless, it can be seen that GNb AC1 and recombinant human IgG4 with inserted Ligand, are efficient on lymphocyte activation (both reducing Interferon-gamma production), whereas scFV (most probably because monovalent, here) and IgG1 human construct were much less efficient on interferon gamma inhibition. Here, the fact that human IgG1 Fc region has proactive effects on human immune cells, clearly indicate that this property can counterbalance the inhibitory effects of the Ligand on this type of lymphocyte activation by ENV. With the same Ligand in human IgG4 vector (which is not immunologically proactive), displays the inhibitory effect of the divalent Ligand as in the original murine IgG.

For this reason, as for what is exposed in example 5.d section, IgG4 would be a preferred construct when immune functions of antibodies should be avoided. As it reveals to be the case here, the antibody functions are not necessary for the inhibitory effect (given that a divalent Ligand is produced, as monovalent scFV have poor efficiency) but also reveal deleterious to the inhibitory effect of the Ligand.

Concerning the effect on IL-6 production (from monocyte/macrophages and, possibly also, B-lymphocytes) IgG1 and IgG4 reveal rather equivalent and good inhibition, which differs from what was seen with Interferon-gamma. Interestingly, the monovalent scFv displays less but significant inhibition of this "innate immunity" cytokine. Thus, certain immune activations are well inhibited by both IgG1 and IgG4 human vectors with the Ligand, but IgG4 displays unique inhibition of both innate immunity (IL-6 results) and acquired immunity (IFN-gamma results) cells from human PBMC. Interestingly, IgG1 vector nonetheless provides stronger inhibition of innate immunity pro-inflammatory cytokines (represented here by the example of IL-6) and triggers some T-cell clones (as reflected by dosages of Interferon gamma), which could reveal useful in certain anti-viral defense mechanisms.

We thus confirm the high affinity and biological activity of the Ligand, in a pharmaceutical delivery form consisting of human antibody vectors with common binding affinities and specificities, but diverging immune effects depending on their isotype.

Example 7

Molecular Identification of the Ligand Binding Site on the Target ENV Protein (Anti-Ligand Binding Sequence)

The epitope mapping of the original murine IgG1/kappa (GNb AC1) has been achieved by Pepscan BV., The Netherlands.

From these results, the aminoacid sequence of the binding site of the Ligand is identified to be included within the sequence set forth in SEQ ID No. 20.

Included in the above sequence, the best target epitope consists in the C-terminal part of the cleaved SU (ENV1) domain in the complete ENV protein (ENV-T) and corresponds more particularly to the following aminoacid selected sequence sequence set forth in SEQ ID No. 32.

This anti-ligand sequence (and its selected sequence) is not exclusively, but also, comprised within the primary aminoacid sequence of MSRV envelope protein (ENV) as described in example 2.

Nonetheless, it is known from the man in the Art, that aminoacids may be substituted by their functional equivalent and, here, may provide a similar binding site with a different sequence. Moreover, "MSRV ENV" mimotopes have been described, which can bind efficiently to specific antibodies (Jolivet-Reynaud, C., H. Perron, et al. 1999. "Specificities of multiple sclerosis cerebrospinal fluid and serum antibodies against mimotopes." Clin Immunol 93; 3: 283-93.).

Example 8

Evidence of the Presence of the MSRV-ENV Target Antigen in Patients with MSRV-Associated Diseases: Examples of Associated Diseases or Pathological Syndromes in Multiple Sclerosis, Clinically Isolated (Neurological) Syndrome—CIS—, Chronic Inflammatory Demyelinating Polyneuropathy—CIDP—, Schizophrenia, and Epilepsia 8a. Multiple Sclerosis, Clinically Isolated Syndromes and Polyneuropathies:
Materials and Methods
Immunodosage of ENV Antigenaemia
Preliminary Serum Collection:
The study was approved by the ethical committees of the University Hospitals of Créteil and Grenoble, France. Neurological patients were included from both centres. All patients have given their written informed consent before inclusion. Healthy blood donors were recruited from the transfusion centres of Grenoble and Montpellier. Non neurological controls were obtained from Grenoble. Clinical data on patients are indicated in Results. Serum sample aliquots from MS patients and healthy controls were coded and sent to an independent laboratory for blind testing with ApoH ELISA using colorimetric read-out conditions.

European Multi-Center Serum Collection:

The study was approved by the ethical committees of the faculty of medicine, University of Würzburg in Germany, of the University of Sassari, of the Don Gnocchi's Hospital of Milan in Italy, of Marseille University Hospital in France and of the University of Pamplona in Spain. 74 patients with definite MS according to McDonald criteria (McDonald, Compston et al. 2001) and 14 patients with clinically isolated syndromes (CIS) were included. Corresponding clinical and treatment data are presented in Table 12 below. (McDonald, Compston et al. 2001). In case of MS relapse, blood samples were drawn prior to the beginning of the steroid treatment. Serum sample aliquots from MS patients and healthy controls were coded and sent to an independent laboratory for blind testing with ApoH ELISA using luminometric read-out conditions.

Sample collection: One tube (7 ml B&D dry tube) of blood was collected. The samplings were treated within 2 hours post collection. After blood clotting they were centrifuged for 10 min at 2800 g at 14° C. Serum was then collected and aliquoted in 250 µL in Eppendorf tubes. The aliquots were stored frozen at −20° C.

ApoH-ELISA Immunoassay

Colorimetric method: ApoH coated microtiter plates (APOH Technologies, Montpellier, France) were loaded with sera samples diluted in Tris-HCl 50 mM pH 7.6; the plates were incubated for 1.5 h at 37° C.; the plates were then washed four times with PBS; purified mouse anti-ENV mAb was diluted with PBS containing 5% BSA to a concentration of 10 µg/ml and added. The plates were incubated for 1 h at 37° C. and then washed four times with PBS. Peroxidase-labelled goat anti-mouse IgG (H+L; Sigma) diluted 1:5000 in PBS containing 5% BSA were added, plates were incubated for 1 h at 37° C. and then washed six times with PBS. OPD substrate solution was added and the plates were incubated for 30 min in the dark. Colour reaction was stopped with 2N $H_2SO_4$. The absorbance was read at 490 nm with a Tecan reader. The statistical cut-off value (C.O.) of this test was determined on series of negative sera from 50 healthy blood donors (BD), with the average of triplicates from individual sera as optical density (OD) result. The C.O. was thus calculated from statistically validated series of negative controls, as their average value plus three standard deviations (A+3SD; positivity significance $p<0.01$) and confirmed experimentally on a panel of reference positive and negative samples. The confidence interval for the determination of positivity with the test therefore represents 99.9%.

Luminometric method: Samples diluted in Tris-HCl 50 mM pH7.6 were loaded on ApoH-coated microplates (APOH Technologies, Montpellier, France). Microplates were incubated 1 h 30 min at 37° C., washed four times with PBS. Purified mouse anti-ENV mAb (1 µg/ml in PBS-BSA 5%), were added, microplates incubated 1 h at 37° C. and washed four times with PBS. Peroxidase-labelled goat anti-mouse antibody (Jackson, diluted 1/2000 in PBS-BSA 5%) was added, microplates incubated 1 h at 37° C. and washed six times with PBS. SuperSignal femto (Pierce) substrate solution was added and read with a TECAN reader.

Monoclonal Antibodies

Monoclonal antibodies (Mab) were developed by bioMerieux (Marcy l'Etoile, France) after immunising mice with recombinant MSRV envelope (ENV) protein expressed from cloned RT-PCR regions amplified from purified extra cellular MSRV virions. After mice sera testing by ELISA with ENV, spleen cells were fused with the non-secreting myeloma cell line Sp2/0-Ag14 in order to obtain hybridomas. Specific clones were selected by screening their antibody production in the same ELISA assay. Thus, about 40 MSRV/ENV protein-specific Mab were isolated and about 28 Mab were further selected and their binding specificity validated. Using the ApoH-ELISA technique on human sera, the best binding Mab was 2A12A5.

Results

MSRV ENV Protein Immunodosage in Serum.

We have developed an original microplate immunoassay, in which the capture phase relies upon the particularly efficient properties of Apolipoprotein-H (ApoH) in binding to microbial proteins when associated with envelope structures and/or lipids (Stefas et al., 1997; Stefas et al., 2001). ApoH permits a first low-affinity interaction with amino acid regions of the protein itself, which secondly activates an allosteric reaction causing covalent-like binding of ApoH C-terminus domain with lipid- or membrane-binding domains. Therefore, viral envelope proteins or virion particles can be captured irreversibly and, after washing steps eliminating the original sample, specific antigens can be detected by the addition of a monoclonal antibody targeting a still exposed epitope after the "ApoH" capture step.

For technical validation of the test, both MSRV virion, pelleted and purified from MS B-cell culture supernatants, according to previously described conditions (Perron et al., 1997a; Perron et al., 1997b), and purified recombinant MSRV envelope protein (ENV), were tested with serial dilutions and different anti-MSRV ENV Mab. Comparison was made with well known viruses, such as hepatitis C virus (HCV) and hepatitis B virus (HBV), detected by corresponding specific Mab. After additional trials with real serum samples, Mab 2A12A5 was shown to be most efficient for diagnostic immunodetection after the ApoH capture step and was kept for next studies.

First blind preliminary study: Multiple Sclerosis—MS— and Chronic Inflammatory Demyelinating Polyneuropathy—CIDP.

For a preliminary evaluation of this immunoassay in different groups of patients with various diseases, we first analysed the sera from 29 patients with MS, from 28 patients with other neurological diseases, from 60 patients with non-neurological diseases and from 50 healthy blood donors (total of 167 serum samples). Results are presented in Table 12, for MS and other neurological diseases.

TABLE 12

ENV-immunodetection test for the identification of MSRV-associated diseases or of MSRV-associated sub-groups of patients.

(a) Patients with Multiple Sclerosis (N = 29)

| Patient | Clinical form | Duration (years) | Ratio OD/CO |
|---|---|---|---|
| 1 | RP | 6 | 1.84 |
| 2 | RP | 1 | 1.64 |
| 3 | RR | 3 | 1.62 |
| 4 | RR | 4 | 1.54 |

TABLE 12-continued

ENV-immunodetection test for the identification of MSRV-associated diseases or of MSRV-associated sub-groups of patients.

| | | | |
|---|---|---|---|
| 5 | nr | 2 | 1.54 |
| 6 | nr | nr | 1.35 |
| 7 | nr | nr | 1.31 |
| 8 | nr | nr | 1.37 |
| 9 | 8 | 8 | 1.11 |
| 10 | 19 | 19 | 1.19 |
| 11 | 2 | 2 | 1.12 |
| 12 | nr | nr | 1.19 |
| 13 | nr | nr | 1.12 |
| 14 | nr | nr | 1.11 |
| 15 | nr | nr | 1.06 |
| 16 | 1 | 1 | 1.21 |
| 17 | 5 | 5 | 1.18 |
| 18 | 7 | 7 | 1.18 |
| 19 | 1 | 1 | 1.06 |
| 20 | 4 | 4 | 1.09 |
| 21 | 3 | 3 | 1.18 |
| 22 | 4 | 4 | 1.28 |
| 23 | 2 | 2 | 1.03 |
| 24 | 26 | 26 | 0.95 |
| 25 | 22 | 22 | 0.99 |
| 26 | 4 | 4 | 0.90 |
| 27 | 22 | 22 | 0.70 |
| 28 | 14 | 14 | 0.96 |
| 29 | 18 | 18 | 0.92 |

(b) Patients with OND (N = 20)

| Patient | Disease type | Ratio OD/CO |
|---|---|---|
| 1 | Epilepsia | 0.910 |
| 2 | Chronic Polymyositis | 0.940 |
| 3 | Primary cerebral tumour | 0.640 |
| 4 | Sciatica | 0.940 |
| 5 | Guillain-Barré Syndrome | 1.000 |
| 6 | Stroke | 0.840 |
| 7 | Primary cerebral tumour | 0.880 |
| 8 | Multisystem atrophy | 0.88 |
| 9 | Facial Palsy | 0.940 |
| 10 | Guillain-Barré Syndrome | 1.000 |
| 11 | Epilepsia | 0.930 |
| 12 | ALS | 0.680 |
| 13 | Guillain-Barré Syndrome | 0.830 |
| 14 | Cerebral Metastasis (Lung cancer) | 0.910 |
| 15 | Leigh's disease | 1.000 |
| 16 | Epilepsy | 0.800 |
| 17 | Traumatic medular | 0.810 |
| 18 | Cerebral Abcess (Listeria) | 0.930 |
| 19 | Epilepsia | 0.800 |
| 20 | Stroke | 0.960 |

(c) Patients with CIDP (N = 8)

| Patient | Ratio OD/CO |
|---|---|
| 1 | 1.13 |
| 2 | 1.27 |
| 3 | 1.06 |
| 4 | 1.08 |
| 5 | 1.06 |
| 6 | 0.90 |
| 7 | 0.86 |
| 8 | 0.93 |

APO-H ELISA Results on first serum series - Patients with Multiple Sclerosis (MS), Patients with other neurological diseases (OND), patients with Chronic Inflammatory Demyelinating Polyneuropathy (CIDP) and Healthy Blood Donors (BD). ELISA tests with APO-H capture step (Stefas et al., 1997) were performed with monoclonal IgG (2A12A5 for MSRV ENV), produced and screened for specificity by bioMérieux, Marcy L'Etoile, France. N = Number of patients, nr = Not recorded, OD = Optic Density, P = progressive, RP = Remitting Progressive, RR = Remitting Relapsing. CO = Cut-Off value determining the limit value below which test result is negative. It is determined from the series of Healthy Blood Donors, as show at bottom with their average value plus three times their standard deviation (99% confidence interval). Ratio OD/CO = OD divided by the CO of the experiment, differentiating positive results (>1) and negatives (<1).

Results equal to 1 are considered as "undetermined" and corresponding samples, or new sample from same individuals, must be tested again in a separate experiment for determination. The Mean value (average) and the standard deviation—s.d.—of all optic densities has been determined in each group and sub-group of subjects as indicated below:

BD (N=50): mean value 0.53, s.d. 0.16.

MS (N=29): mean value of positive MS (N=23) 1.27 s.d. 0.22, average of negative MS (N=6) 0.90 s.d. 0.25, mean value of all MS 1.20 s.d. 0.25.

OND (N=20): mean value of negative OND 0.88 s.d. 0.10.

CIDP (N=8): mean value of positive CIDP (N=5) 1.12 s.d. 0.09, average of negative CIDP (N=3) 0.9 s.d. 0.03, average of all CIDP 1.04 s.d. 0.13.

We analysed the sera from 29 MS patients from France (19 from Créteil, 10 from Grenoble) as a preliminary evaluation of this immunoassay in different groups of patients with various diseases. Results in MS patients are presented in Table 12a. Ten healthy blood donors were used as negative standards for the determination of the limit of positivity (cut-off or CO, threshold value under which no specific signal is detected). According to the statistical cut-off value of these series, 23 MS patients have significantly positive MSRV-ENV antigenaemia (mean OD=0.88), whereas 6 can be considered as negative, though rather close to the threshold (mean OD of "negative MS"=0.62). Interestingly, negative MS cases had longer duration of rather benign forms (#24, 25, 28) or were undergoing cyclophosphamide treatment protocol.

In parallel, we analysed the sera from 28 patients with other neurological diseases (OND) (12 from Créteil, 16 from Grenoble). Five patients had a positive result, thus representing about 18% of OND patients tested here. Nonetheless, all positive OND cases had a similar diagnosis: Chronic Inflammatory Demyelinating Polyneuropathy (CIDP), whereas OND patients with other diagnoses were all negative (or "undetermined" at the cut-off limit as for one case of acute Guillain-Barré's syndrome). Thus, results from OND patients are presented in Table 12b as OND without CIDP separately from CIDP patients (Table 12c). About a half of CIDP cases are positive but, given the present low numbers, we did not mean here to analyse "inflammatory" versus "non-inflammatory" neurological diseases.

Furthermore, we have tested in parallel sera from other non-neurological diseases (ONND) such as 15 patients with chronic hepatitis B virus infection as well as 15 patients with chronic hepatitis C virus infection. None of these 30 samples was found to be positive. Polyreactive sera from 30 patients with anti-DNA, anti-nucleus and anti-rheumatoid factor, usually interfering with numerous serological tests, did not yield any positive result either. Fifty sera from healthy blood donors were also tested in parallel. None was found to be positive.

Comparison of results from the MS group with any other group shows a significant difference, except for the CIDP sub-group. Optic density values from the complete MS and OND groups (including negative MS and CIDP), when compared with a non-parametric test (normality test failed), are quite significantly different (p=<0.001; Mann-Whitney's rank sum test T=517,000). When comparing the complete MS group with all CIDP cases, a statistical difference cannot be found any longer (p=0.053; Mann-Whitney's rank sum test T=99,000). No significant difference was either evidenced between OD values of "positive MS" and of "positive CIDP" (P=0.072; Mann-Whitney's rank sum test T=42, 000).

European Multi-Centre Serum Series with Blind Testing: Multiple Sclerosis—MS—and Clinically Isolated Syndrome—CIS.

In order to confirm the first results with a larger panel of MS patients from different geographical areas, we recruited sera within a multi-centre collaboration with neurological departments from different European countries. In these samples, we used a luminometric read-out in order to improve signal detection and differentiation with non-specific background "noise".

After internal evaluations of sera with the colorimetric method, comparison with luminometry read-out confirmed enhanced signal detection and dynamics. Thus, a sampling of sera for quadruplicate assay was made in randomly selected MS patients with all forms and durations of disease, mostly with ongoing specific treatment, but representing each geographical origin of the present clinical network. They were coded and sent for blind testing to a centralised laboratory (APO-H technologies, Montpellier, France). Non-coded sera (10 negative controls and 10 positive MS) were sent for technical validation for determination of the cut-off value. In addition, 14 sera from clinically isolated syndrome (CIS, single neurological episode and additional imaging and/or biological abnormalities) were sent coded and blind tested within this series. This was a first evaluation in CIS and was expected to comprise a majority of MS first episodes.

Figure 8:
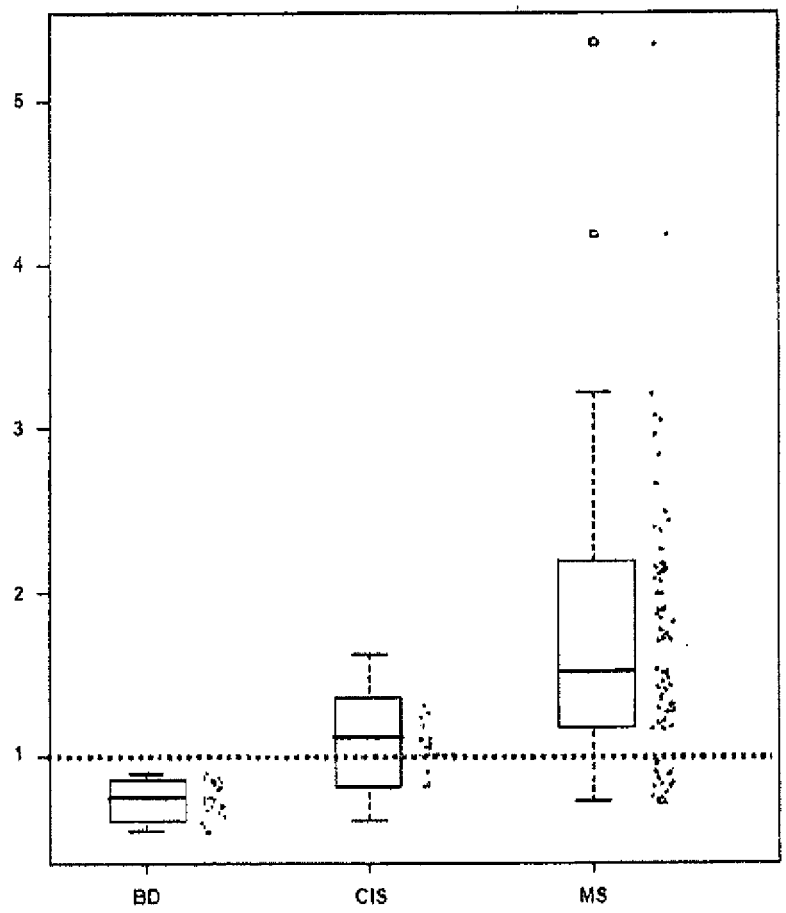

The results are presented in FIG. 8 (ApoH-ELISA results of sera from the European multicenter study tested blindly in an independent laboratory). They are expressed as the ratio of luminometry units (RLU) divided by the cut-off value determined within the same experiments, thus being comparable with the ratio of the previous series (Cf. Table 9). Indeed, the range of ratios (1 to 6) obtained here within "positive MS" sera with luminometry confirms the technical optimisation of signal dynamics compared to colorimetry (1 to 2).

ApoH-ELISA Results of Sera from the European Multicenter Study Tested Blindly in an Independent Laboratory.

The read out technique used was luminometry and the results are presented on the Y axis as the ratio of individual luminometry units (RLU) divided by the Cut-Off Value determined on series of reference negative sera within the same experiment. Thus, values>1 are positive.

Statistic analyses of APO-H ELISA luminometry results between groups gave the following results (Fisher test p values): (i) comparing BD vs. all MS, BD vs. all MS+CIS, BD vs. RRMS, BD vs. PPMS, BD vs. SPMS, BD vs. CIS: $p<0.001$; (ii) comparing CIS vs. RRMS: $p=0.759$, CIS vs. PPMS: $p=0.704$, CIS vs. SPMS: $p=0.749$, RRMS vs. PPMS, SPMS: $p=1$, PPMS vs. SPMS: $p=1$.

Here, 54 out of 74 non-selected MS cases (73%), originated from the different countries and regions of the study, had a positive antigenaemia for MSRV ENV protein, but none of the coded 26 BD (as for the 10 non-coded BD used as reference samples for the experiment). The present difference between MS and BD was highly significant (Chi-Square: $p<0.0001$), but separate "non-blind series" with larger numbers (over a hundred) detected few positive healthy or asymptomatic blood donors (4/103; not shown). Interestingly, 9 out of 14 CIS (about 64%) were positive, but with lower values.

Values from different groups (MS, BD, CIS) as well as from different sub-groups representing different forms of MS, primary progressive (PPMS), secondary progressive (SPMS) and relapsing-remitting (RRMS) were compared with Fischer's test. Results of the healthy blood donors were significantly different from all MS and CIS combinations (constantly $p<0.001$), whereas no significant difference in the detection of MSRV ENV antigenaemia was evidenced between any sub-group representing either possible (CIS) or definite MS, or different MS disease evolution forms (71% were positive in RRMS, 78% in PPMS, 70% in SPMS). Nonetheless, a slight tendency of heterogeneity in CIS versus MS sub-groups is illustrated by lower p values: $p=0.7$ to 0.75, versus $p=1$ between MS forms, the latter value revealing statistically identical result distribution.

8b. Psychiaric Disease Series: Schizrophrenia-SCZ.
Patients and Methods
Patients and Healthy Controls Patients, fulfilling DSM-IV (American Psychiatric Association: Diagnostic and statistical Manual of Mental Disorders, DSM-IV; 1994) criteria for schizophrenia were randomly selected at the end of a hospitalisation for an acute episode in a French university-affiliated-psychiatry department. Neurological disorder, acute or chronic infection, and positive serology for Human Immunodeficiency Viruses (HIV1+2), Hepatitis B and C Viruses were exclusion criteria. Age and gender distribution in these normal controls was not statistically different from the present patient's group. Psychotic symptoms were assessed with the French version of the Signs and Symptoms of psychotic illness scale—SSPI—(Houenou et al., 2007). Mood symptoms were assessed with the Bech and Rafaelsen mania rating scale and the Montgomery and Asberg depression rating scale—MADRS—(Bech et al., 1978; Montgomery and Asberg, 1979). The protocol was approved by local ethics committee. Signed informed consent was obtained from all subjects, after complete description of the study by the psychiatrist in charge of the clinical evaluations of patients.

Serum Collection

One tube (7 ml B&D dry tube) of blood was treated within 2 hours after collection: after clotting they were centrifuged 10 minutes at 2800 g and 14° C. Serum was collected, aliquoted in low binding tubes and stored at −80° C.

Immunoassay

ELISA tests with APO-H capture step (Stefas et al., 1997) were performed with monoclonal IgGs (2A12A5, 6A2B2 for MSRV ENV and 2G5E12 for MSRV GAG), produced and screened for specificity by bioMérieux, Marcy L'Etoile, France.

100 µl per well of samples diluted 1/10 in Tris-HCl 50 mM pH7.6 were loaded on ApoH-coated microplates (APOH Technologies, Montpellier-France). Microplates were incubated 2 hours at 37° C., washed four times with 250 µl of PBS per well. 100 µl per well of primary antibody (10 µg/ml in PBS-BSA 2%) were added, microplates incubated 1 hour at 37° C. and washed four times with PBST 0.05% plus twice with PBS. 100 µl per well of peroxidase-labeled antibody (anti-mouse Jackson, 1/250 in PBS-BSA 2%) were added, microplates incubated 1 hour at 37° C. and washed as previously. 100 µl of substrate solution (OPD) per well was added, microplates incubated 30 minutes in the dark and the reaction stopped with H2SO4 2N (50 µl/well). The absorbance was read at 490 nm with a Biotek reader.

Statistical Analyses:

They were performed with SigmaStat Software. Non parametric test Mann-Whitney Rank Sum test was selected for comparison of data series, since their distribution never fitted the Normal distribution (Normality Test failed). Chi-Square test was used to compare the prevalence of positive versus negative antigenaemia in each population, for each antigen and/or each antibody used. The cut-off value for each condition, under which results are, was calculated from statistical series of negative controls as their average value plus three standard deviations (M+3SD; significance of positivity: p<0.01) and confirmed on reference positive and negative samples.

Results 49 schizophrenic patients and 49 controls, matched for age (33+/−6.5 years) and sex (73% men, 27% women), have been included. Eight patients were included at first onset of schizophrenic disorder, whereas the majority (N=41) had severe chronic schizophrenia. They were euthymic at inclusion both for depressive scores (mean MADRS=5.6+6.6) and for manic score (mean Bech score=4.8+4.5). All patients but untreated one, took antipsychotic drugs (27% classical and 71% atypical antipsychotics. One third of the patients (N=13) were drug resistant according to Kane criteria (Kane 1996).

For MSRV GAG antigen, 49 controls and 49 schizophrenic patients were tested. For MSRV ENV 30 controls (due to technical limitations) and 49 schizophrenic patients were tested. Results of the immunoassay are expressed as mean optic density obtained on serum duplicates divided by the cut-off value, in order to make all series comparable with normalised values (FIG. 22 and table 10).

47% (N=23) and 43% (N=21) of schizophrenic subjects had positive MSRV ENV antigenaemia, respectively with 2A12A5 and 6A2B2 antibodies. 49% (N=24) of schizophrenic patients had positive MSRV GAG antigenaemia, one being positive and one being "borderline" for GAG only. Comparison with the healthy controls revealed a significant difference in the prevalence of positives (Chi-square test: p<0.001 for both ENV detections; p<0.0001 for GAG). Comparing ELISA values in patients versus controls with Mann-Whitney Rank Sum Test also confirmed highly significant differences (p<0.001; Table 2). Among controls, one subject had significantly positive antigenaemia. Interestingly, there was a positive correlation between the results for ENV protein and those obtained for GAG protein. Mann-Whitney Rank Sum test comparing ELISA values obtained with anti-ENV6A2B2 to those obtained to anti-GAG 2G5E12 revealed no significant difference (p=0.744), as for anti-ENV-2A12A5 compared to anti-GAG-2G5E12 (p=0.290), and for anti-ENV-6A2B2 compared to anti-ENV-2A12A5 (p=0.159). Therefore, these antibodies detected an equivalent and/or parallel expression of MSRV antigens:

"ENV" antigenaemia ELISA values varied among positives, as shown in Table 10 by the increased standard deviations (0.28 for 2A12A5 antibody, 0.48 for 6A2BA) compared to negative controls (0.09 and 0.08 respectively). This is confirming the detection of a dynamic production of MSRV antigens in certain patients with Schizophrenia.

TABLE 13

MSRV capsid (GAG) and envelope (ENV) dosages in the sera of schizophrenic (SCZ) patients and controls

| | MSRV ENV | | | | MSRV GAG | |
|---|---|---|---|---|---|---|
| | 2A12A5 antibody | | 6A2B2 antibody | | 2G5E12 antibody | |
| | SCZ | Controls | SCZ | Controls | SCZ | Controls |
| Number of positives per Sera in tested Populations | 23/49 46.94% | 1/30 3.33% | 21/49 42.86% | 0/30 0.00% | 24/49 48.98% | 2/49 4.08% |
| Number of Positives in SCZ versus BD: Chi-Square Test | CHI2 = 16.73 (P < 0.001) | | CHI2 = 17.51 (P < 0.001) | | CHI2 = 25.34 (P < 0.0001) | |

TABLE 13-continued

MSRV capsid (GAG) and envelope (ENV) dosages in the sera of schizophrenic (SCZ) patients and controls

| | MSRV ENV | | | | MSRV GAG | |
|---|---|---|---|---|---|---|
| | 2A12A5 antibody | | 6A2B2 antibody | | 2G5E12 antibody | |
| | Positive SCZ | Neg. controls | Positive SCZ | Neg. controls | Positive SCZ | Neg. controls |
| Standard deviation: Positive SCZ sera/ Negative Controls sera | 0.28 | 0.09 | 0.48 | 0.08 | 0.47 | 0.15 |
| Number of Positives in SCZ versus BD Mann-Whitney Rank Sum Test | T = 603,000 (P = <0.001) | | T = 638,000 (P = <0.001) | | T = 1451,500 (P = <0.001) | |

SCZ: Schizophrenic Patients;
BD: Blood

The Immunoassay (ELISA) test ratio (Y axis) is the average optic density measured on duplicate wells from the same serum divided by the cut-of value of the corresponding series (Cf. Materials and Methods). ENV antigen is dosed with either 2A12A5 monoclonal antibody or 6A2B2 monoclonal antibody and GAG is antigen dosed with 2G5E12 monoclonal antibody as indicated in respective columns with plotted values.

Figure 9:
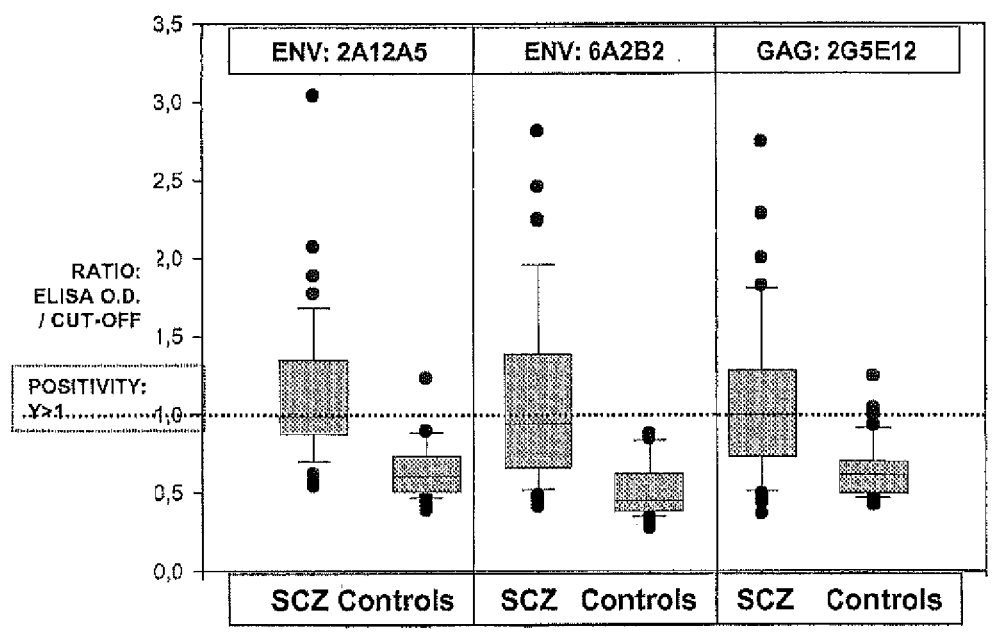

In FIG. 9, the average value and confidence intervals (0.01 and 0.001) are represented by bars and boxes, and the distribution of maximum and minimum values for each antigen and antibody (indicated on top of each column) are represented by points. The series of values from patients with Schizophrenia are indicated as "SCZ" at the bottom of corresponding plots, and those from healthy blood donors are labelled "Controls" (Bottom/X axis).

8c. Other Neurological Diseases: Epilepsy.

Figure 10:
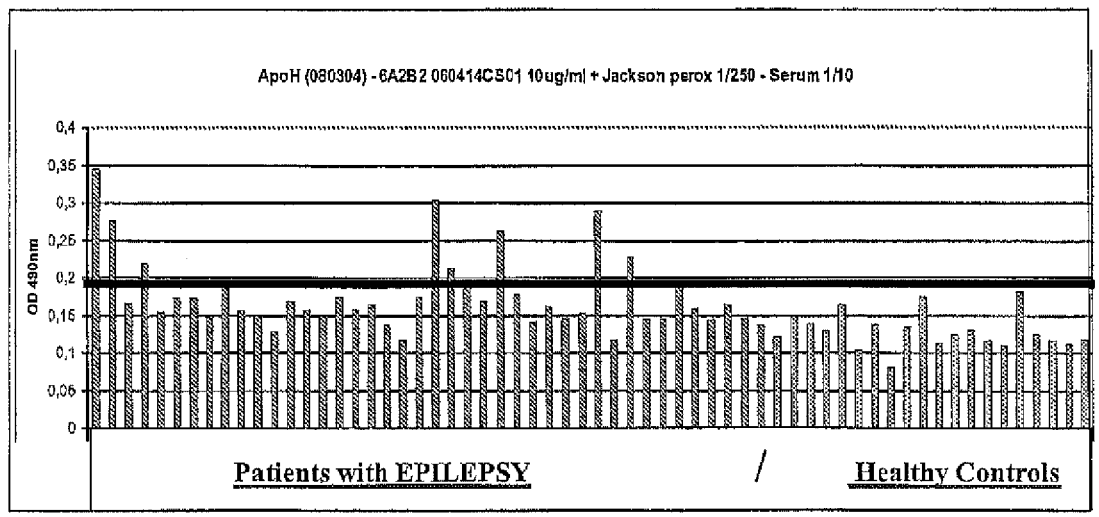

The ELISA tests were performed as described above (8b). Patients with Epilepsy and normal controls were tested in parallel for the presence of MSRV-ENV protein in their sera. The results are presented in FIG. 10.

Each vertical bar represents the mean OD of duplicate results from the serum of a single patient with epilepsy (38 from the left) or control (24 from the right).

The horizontal black bar represents the cut-off value of the test, above which the signal detected is specific of antigen presence in serum. It is determined by the average of results from the healthy blood donors (controls) plus three times their standard deviation.

Thus, here, we have detected a sub-group of 8 patients with MSRV-ENV associated Epilepsy, which may simply correspond to a subgroup with this particular aetiology among other cases with a different aetiological cause. Only MSRV positive epilepsy is relevant for the treatment with anti-ENV Ligand in, e.g. antibody vectors.

8d: Patients with Psoriasis.

Patients with Psoriasis have long been known to express similar retrovirus (Iversen, O. J. (1990), "The expression of retrovirus-like particles in psoriasis." J Invest Dermatol 95(5 Suppl): 41S-43S./Bjerke, J. R., G. Haukenes, et al. (1983), "Activated T lymphocytes, interferon, and retrovirus-like particles in psoriatic lesions." Arch Dermatol 119(12): 955-6). Therefore, their relevance for the present therapeutic vectors comprising the Ligand is obvious for the man skilled in the Art.

Example 9

In Vivo Efficiency of Pharmaceutical Vectors Comprising the Ligand and Retaining the Ligand Affinity with Activity Characteristics, Versus GNbAC1. In vivo Evidence of Anti-Inflammatory, Immunoprotecting and Neuroprotecting Effects of the Ligand, Delivered Under the Form of a Vectorised Ligand with an Appropriate Pharmacological Vector Compound: Example of Therapeutic Effect in Animal Models with Neuro-Inflammation, Demyelination and/or Neuronal Degeneration Materials and Methods:

MSRV/ENV-Induced EAE in Humanized SCID (huS-CID) Mouse Model.

Pathogen-free 6 to 8 week-old SCID mice were purchased from Charles River, France. Humanization of mice was achieved using PBMCs from healthy blood donors (Etablissement Français du Sang, Lyon, France), according to previously described protocol (Firouzi et al., 2003). In particular mice were gamma-irradiated and received anti-NK antibody prior to humanization with $50 \times 10^6$ human PBMCs by intraperitoneal (i.p.) injection. The quality of humanization was then controlled by specific detection of human immunoglobulin in mouse serum. When more than one donor per series is needed, all huSCID sub-groups were made comparable with the same proportion of mice humanized with each blood donation.

A delay of 2 weeks before inclusion in the EAE protocol (before first injection with myelin antigen) was necessary. Then, mice groups were either injected with myelin basic protein (MBP) and incomplete Freund's Adjuvant (IFA, comprising diluents only) for "mock-control" groups, or injected with MBP and purified endotoxin-free MSRV ENV protein homogenized in IFA diluents for "ENV-induced" EAE. When disease activity was monitored clinically and by MRI to have caused lesions and progressing clinical deficits, the effect of a selected anti-ENV Ligands compared to the original murine monoclonal antibody (GNb_AC1), was studied with injection in ill-mice (MBP-EAE induced by ENV in huSCID mice).

For the induction or "mock-induction" of EAE animals were first injected s.c. in the neck on day 0, either with 50 μg of human MBP+150 μg of MBP peptide (MBP peptide 87-99)+20 μg of recombinant ENV protein+IFA (ENV group) or with 50 μg of human MBP+150 μg of MBP peptide (MBP peptide 87-99)+IFA only (control group). 200 ng of pertussis toxin (PTX) per animal was also i.p. 2 days after in all groups. A second injection by the intraperitoneal (i.p.) route of the same components at the same dose (including the MBP peptide and human MBP complete protein), corresponding to the previous description for each group, was made on indicated day (Table 11). It was also accompanied by similar injection of 200 ng per animal of PTX. The third and last injection of the same immunogens was made s.c. in the opposite side of the neck on indicated day (Table 14), accompanied by similar injection of PTX.

TABLE 14

Antibody treatment evaluation pre-clinical series: description of the different groups and protocols for ENV-induced and control "MBP-EAE" in Hu-SCID mice.

| | | | Components | | MAh | Clinical assessment | |
|---|---|---|---|---|---|---|---|
| Groups | Description | Injected | FA | NV (20 μg) | (100 μg on days) | Clinical Score | MRI (days) |
| 1 | Control Mice | X | X | — | | daily | 17; 24; 31; 43; 50 |
| 2 | Control Mice | X | X | — | 19; 35 | daily | 17; 24; 31; 43; 50 |
| 3 | EAE mice | X | X | X | — | daily | 17; 24; 31; 43; 50 |
| 4 | EAE mice | X | X | X | 35 | daily | 17; 24; 31; 43; 50 |
| 5 | EAE mice | X | X | X | 19; 35 | daily | 17; 24; 31; 43; 50 |

For follow-up, animals were weighed 5 days per week and clinically scored. Clinical score was made according to the following criteria: 0=no signs; 1=tail paralysis or hyperreflexia of hind limb(s) or unilateral hind limb weakness; 2=bilateral hind limb or forelimb weakness; 3=plus unilateral paralysis or major deficit; 4=complete hindlimb or forelimb paralysis; 5=plus partial paralysis or major deficit of opposite limbs; 6=moribund or dead.

The total duration of the Hu-SCID experiments did not exceed two months, with the exception of the survival studies involving the mAb treated and control mice (four months).

MRI and Immunohistochemistry Analysis (Pictures not Shown in the Present Example):

Animals were monitored by MRI T2-Weighted analysis and post-mortem histology, which confirmed both the types of lesions with inflammation and demyelimation in the central nervous system, as well as imaging (MRI) striking improvement of inflammatory patterns in treated mice with clinical improvement.

Results:

SCID mice with human lymphoid system (grafted as indicated above) provide hybrid animals with a functional human immune system. These animals have here received three injections of MSRV ENV protein emulsified with MBP in oily diluents (IFA), at days indicated by the blue arrows. When the animals had elevated clinical score with ongoing neuroinflammation visualized by MRI (EAE), they were injected with a single dose (10 μg intraperitoneally) of the original murine monoclonal antibody (GNb AC1, indicated as mulgG on the FIG. 10) or of one of the human IgG1 or IgG4 constructs with the Ligand (indicated as hulgG1 and hulgG4 on FIG. 11). A group remained untreated, in order to compare with treated animals and the "mock-control" group injected with MBP in IFA without ENV remained healthy, but received an injection of the original murine antibody (GNbAC1) on the same day as the treated ill animals.

As can be seen from results illustrated in FIGS. 11 and 12, all the non treated mices died after 30 days and had severe clinical progression after the last of the three injections with MSRV ENV protein. Severe lesions were seen by histology and immunohistology, evidencing demyelination, lymphoid cell infiltration, neuronal death, blood brain barrier breakdown and astrogliosis. Interestingly, in Multiple Sclerosis, the blood brain barrier breakdown is also a hallmark of active CNS lesions.

Thus, the murine antibody or the chimeric human IgG 1 or 4 comprising the Ligand targeting ENV, could diffuse from intraperitoneal injection to the whole body and, in particular, to the active CNS lesions in ill animals.

Figure 11:
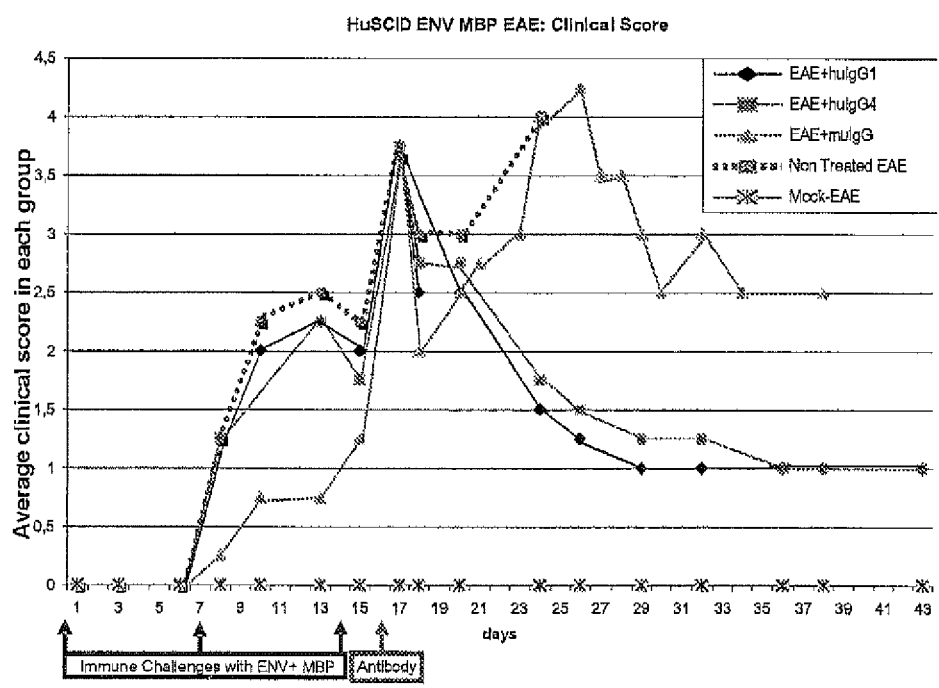
Figure 12:
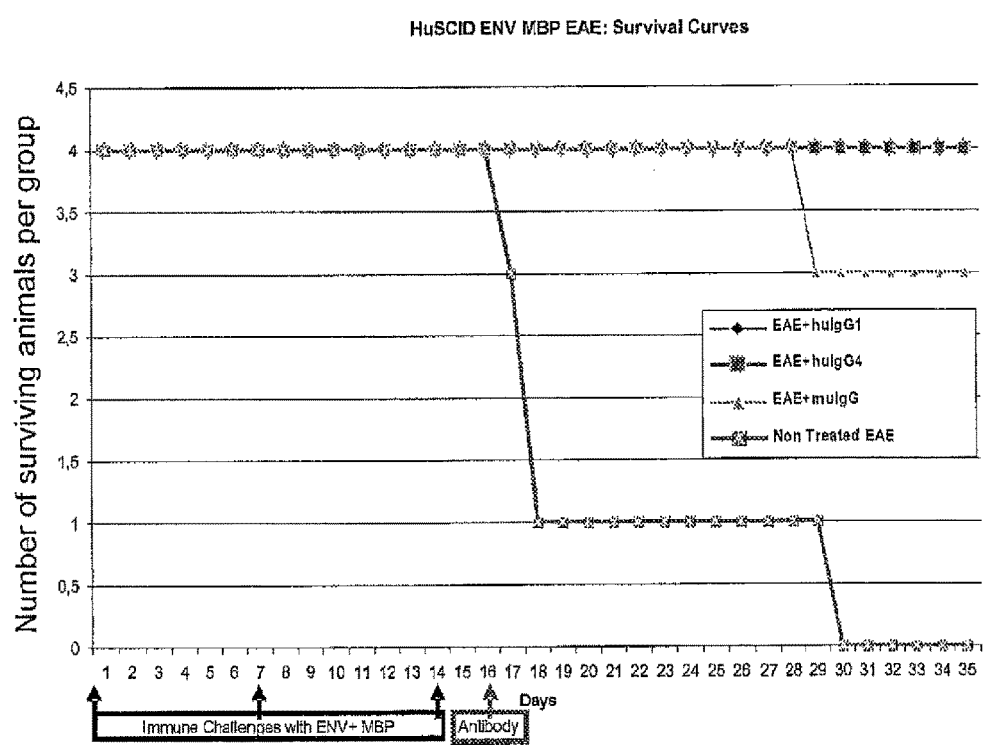

Strikingly, the survival curves show 100% of survival in animals treated with either IgG1 or IgG4 chimeric antibodies versus 0% in non treated ones at day 35. Surprisingly, the original murine IgG1/kappa (GNbAC1) has less efficiency when injected at the same dose, since one animal died at day 28. Moreover, the clinical curves in FIG. 11 show a very good and lasting improvement in animals treated with human IgG1 or 4 constructs, but only stabilization or mild improvement in animals treated with the original murine antibody.

Such a striking improvement of animals treated with Ligand in human IgG1 or IgG4 vectors, was also evidenced by MRI monitoring, compared to untreated controls.

Thus, the clinical efficiency of the human chimeric IgG 1 or 4 is confirmed on animal models showing neuroinflammation, demyelination, neuronal death, blood brain-barrier breakdown and astrogliosis in the Central Nervous System (CNS; Cf. Hu-SCID and C57/bl6 models injected with MSRV ENV protein). Surprisingly, the efficiency is improved, compared to the original murine IgG containing the same Ligand (VH+VL chains).

Thus, the therapeutic efficiency in the present animal model of neuroinflammation is making it obvious for other applications in MSRV-associated diseases or syndromes, as defined in the text of the present invention.

Moreover the unexpected "Ligand effect" of a minimum composition or construction comprising the 6 CDRs defined in example 1, makes it possible to use the Ligand totally independently from antibody functions, but also to vary and choose the added values and relative interests of different vectors (not exclusively relating to IgG isotypes) for each possible therapeutic application.

Example 10

MSRV-ENV Protein is Detected with Great Intensity in Certain Cells from Biopsies in Patients with Solid Tumour or from Biopsies in Patients with Lymphoproliferative Disorders or Lymphoid Cancers Materials and Methods:
Test Antibody
GNb AC1, 1.0 ml, concentration: 5.918 mg/ml
Negative Control Antibody
Mouse Myeloma Protein IgG1 kappa (MOPC-21, Sigma), 1.0 ml, concentration: 1.0 mg/ml
This antibody was used concurrently with the test antibody.
Inhibition Protein
ENV-T (MSRV ENV, GeNeuro SA), 10 ml (10×1 ml vials), Concentration: 0.05 mg/ml
This anti-ligand was used concurrently with the test antibody.
Human Tissue Samples
Ethically collected human tissues with full patient consent were obtained from an external source.
All tissues were subjected to antigenicity testing. An IHC stained section of a commonly expressed protein; S100, CD45, desmin, cytokeratin or vimentin associated with each tissue was assessed before deeming the tissues acceptable for use on this study.

Assay Validation
The parameters investigated included:
1. Comparison of staining in the positive control tissue using neutral buffered formalin, paraformaldehyde and acetone fixation.
2. The use of an appropriate immunostaining detection method.
3. Optimum titre determination of the test antibody, from 0 to 5.0 µg/ml was investigated (the isotype control antibody was run at the same concentrations).
4. The specificity of the staining was validated by omission of the test antibody being substituted with buffer. In addition the antigenic binding sites of MSRV were blocked using ENV-T protein prior to tissue incubation.
5. Any necessary blocking of endogenous materials that could interfere with target antigen signal was employed.
Immunohistochemical (IHC) Staining Method
As a result of the findings of the validation phase each of the tissue samples were screened concurrently in the following manner:
GNbAC1 omitted from the staining procedure
MOPC-21 antibody at 1.0 µg/ml
GNbAC1 at 0.25, 1.0 and 3.0 µg/ml
Each tissue sample was evaluated using a light microscope. The scoring system identified tissue and cell type and reflected subjectively the intensity of that staining.

All staining in tissues treated with either the negative control antibody or with no antibody, and which did not specifically delineate individual cells, were assumed to be non-specific. No specific staining was recorded for tissues treated with the test antibody when the immunohistochemical staining in these tissues was similar in intensity and distribution to tissues which were not treated with the test antibody and where individual cells were not specifically delineated.

Positive staining was recorded by naming the tissue structure or types of cells and then indicating the intensity as follows:

| | |
|---|---|
| 0 | Negative |
| + | Mild |
| ++ | Moderate |
| +++ | Marked |

The frequency of staining identified in each cell type was indicated as follows:

| | |
|---|---|
| <10% | Few |
| 11-40% | Several |
| 41-75% | Many |
| >76% | Most |

If a section was not considered suitable for evaluation no data was included for it in the table of results until, where possible, the staining was repeated.

There was less membrane staining at 0.25 µg/ml compared to the other dilutions tested.

Liver tissue was included as a comparison between a known positive control and a tissue that was not initially identified as being positive.

No significant staining was identified in the negative buffer control or isotype. Positive staining compared to the positively stained tissues was virtually eliminated when ENV-T was reacted with anti-MSRV/ENV GNbAC1 antibody.

For future screening work the test Mab, GNb AC1, was used at 1.00 µg·ml$^{-1}$ as the optimum concentration, with 3.00 µg·ml$^{-1}$ as being one step above that and 0.25 µg·ml$^{-1}$ as being the low concentration.

As a result of the findings from the validation, the following IHC staining procedure was adopted for the screening of the frozen normal human tissue.

| Procedure | Time |
| --- | --- |
| Air dry tissue sections | N/A |
| Fix in acetone and air dry | 10 minutes approx. |
| Wash in running tap water | N/A |
| 0.3% hydrogen peroxide in methanol | Approx. 10 mins. |
| Wash in tap water | Approx. 5 mins. |
| Wash in PBS | Approx .5 mins |
| Incubate with GNb AC1 monoclonal antibody at 0.25, 1.0 and 3.0 µg/ml and with the isotype control at 1.0 µg/ml. Also omit primary from staining | Overnight at 2-8° C. |

-continued

| Procedure | Time |
| --- | --- |
| procedure and inhibit with ENV-T at 10 µg/ml with GNb AC1 at 1.0 µg/ml | |
| Wash in PBS | Approx. 5 mins. |
| Incubate with EnVision/HRP | Approx. 30 mins. |
| Wash in PBS X2 | Approx. 5 mins. each |
| Treat with DAB enzyme substrate | Approx. 5 mins. |
| Wash in running tap water | Approx. 5 mins. |
| Counterstain in Mayers Haematoxylin | Approx. 15 secs. |
| Wash in running tap water | As required |
| Dehydrate, clear and mount | As required |

Results:

Breast Cancer.

TABLE 15

Results obtained with breast carcinoma tissues from different individuals.

| | Microscopical Findings | ENV-T 10.00 | Isotype 1.00 | | GNb AC1 Antibody concentration ug/ml | |
| --- | --- | --- | --- | --- | --- | --- |
| | | | | 0.00 | 0.25 | 1.00 | 3.00 |
| Breast (mammary) | Ductal/glandular epithelia. Cytoplasmic/Membrane | 0 | 0 | 0 | Few + | Several ++ | Few + |
| | Luminal Contents. | 0 | 0 | 0 | 0 | Several + | Few + |
| (carcinoma in situ) | Luminal Surface. | 0 | 0 | 0 | 0 | Several ++ | Many ++ |
| | Vessels-Endothelia Cytoplasmic/Membrane | 0 | 0 | 0 | 0 | Many ++ | Few + |
| | Ductal/glandular epithelia. Cytoplasmic/Membrane | 0 | 0 | 0 | 0 | Few + | Many +++ |
| | Luminal Contents. | 0 | Several + | Several + | Several + | Several ++ | Several +++ |
| (adeno- carcinoma breast) | Luminal Surface. | 0 | 0 | 0 | 0 | Few + | Many +++ |
| | Vessels-Endothelia Cytoplasmic/Membrane | 0 | 0 | 0 | 0 | Several ++ | Many ++ |
| | Ductal/glandular epithelia. Cytoplasmic/Membrane | 0 | 0 | 0 | 0 | Few + | Several ++ |
| | Luminal Contents. | 0 | 0 | 0 | 0 | 0 | 0 |
| (adeno- carcinoma breast) | Luminal Surface. | 0 | 0 | 0 | 0 | Several + | Most ++ |
| | Vessels-Endothelia Cytoplasmic/Membrane | 0 | 0 | 0 | 0 | Several + | Several ++ |

INTENSITY Negative 0 Mild + Moderate ++ Marked +++
FREQUENCY Few Several Many Most It can thus be evidenced that MSRV ENV is highly expressed in ductal/glandular epithelial cells and in endothelial cells of surrounding blood vessels in 3/3 breast mammary tumours tested with specific GnbAC1.

Thus, according to the notion of "MSRV associated diseases", it is now evidenced that breast cancer carcinoma is one of these human diseases.

Lymphoid Cancer and Lymphoproliperhative Disorders:

TABLE 16

Results obtained with hyperplasic lymphoid tissues from different individuals.

| | Microscopical Findings | ENV-T 10.00 | Isotype 1.00 | Antibody concentration ug/ml GNb AC1 | | |
| --- | --- | --- | --- | --- | --- | --- |
| | | | | 0.00 | 0.25 | 1.00 | 3.00 |
| Tonsil | Lymphoid cytoplasm membrane | 0 | 0 | 0 | Several +++ | Many +++ | Several +++ |
| | Vessels endothelial cytoplasm membrane | 0 | 0 | 0 | Few ++ | Many ++ | Many +++ |

TABLE 16-continued

Results obtained with hyperplasic lymphoid tissues from different individuals.

| | Microscopical | Antibody concentration ug/ml | | | | | |
|---|---|---|---|---|---|---|---|
| | | ENV-T | Isotype | | GNb AC1 | | |
| | Findings | 10.00 | 1.00 | 0.00 | 0.25 | 1.00 | 3.00 |
| (follicular hyperplasia) | Lymhoid cytoplasm membrane | | | | Many +++ | Most +++ | Most +++ |
| | Vessels endothelial cytoplasm membrane | 0 | 0 | 0 | Few ++ | Many ++ | Many +++ |
| (follicular hyperplasia) | White cells in vessel Cytoplasm membrane | Many ++ | 0 | 0 | NI | NI | NI |

INTENSITY Negative 0 Mild + Moderate ++ Marked +++;
FREQUENCY Few Several Many Most;
NP: Not Practicable It can thus be evidenced that MSRV ENV is highly expressed in lymphoid cells and in endothelial cells of surrounding blood vessels in 2/2 tonsil biopsies with marked hyperplasia from patients with lymphoproliferative disorder, when tested with GNbAC1.

Thus, according to the notion of "MSRV associated diseases", it is now evidenced that lymphoproliferative disorders, including lymphoid cell cancers, are amongst these human diseases.

Renal Cancer

Thus, according to the notion of "MSRV associated diseases", it is now evidenced that renal cancers, are one of these human diseases.

Corresponding photographs from light microscopy visualization of tissue sections stained with either specific anti-ENV antibody (GNb AC1) or irrelevant control antibody (MOPC-21) have confirmed the findings presented in Tables 15-17, for Kidney cancers for Lymphoid cancers or lymphoproliferative disorders and for Breast Cancer

TABLE 17

Results obtained with renal carcinoma tissues from different individuals.

| | Microscopical | Antibody concentration microg/ml | | | | | |
|---|---|---|---|---|---|---|---|
| | | ENV-T | Isotype | | GNb AC1 | | |
| | Findings | 10.00 | 1.00 | 0.00 | 0.25 | 1.00 | 3.00 |
| (cancer Kidney) | Tubule lumen surface Cytoplasmic/Membrane | 0 | 0 | 0 | Few + | Few + | Many +++ |
| | Glomerular mesangial Membrane/Cytoplasm | 0 | 0 | 0 | 0 | 0 | 0 |
| | Glomerular vessel loops Endothelium/Cytoplasm | 0 | 0 | 0 | Few +++ | Few +++ | NI NI |
| | Tubule Casts | | | | 0 | Many +++ | Most + |
| (renal cell carcinoma) | Tubule lumen surface Cytoplasmic/Membrane | | | | Few + | Several ++ | Several ++ |
| | Glomerular mesangial Membrane/Cytoplasm | | | | Few +++ | Few +++ | Few +++ |
| | Bowmen's Capsule | | | | 0 | Several +++ | Several +++ |
| | Glomerular vessel loops Endothelium/Cytoplasm | | | | 0 | Many +++ | Most +++ |
| | Tubule Casts | | | Few + | Few + | Few + | |

INTENSITY Negative 0 Mild + Moderate ++ Marked +++;
FREQUENCY Few Several Many Most;
NP: Not Practicable Despite light background staining in one cell type (different in each case), analysis was practicable and it can thus be evidenced that MSRV ENV is highly expressed in renal cells and in endothelial cells of surrounding blood vessels in 2/2 renal biopsies from patients with renal carcinoma, when tested with specific anti-MSRV ENV antibody (GNbAC1).

Example 11

A. MSRV ENV and GAG Proteins are Detected with Significant and Concordant Levels in the Serum of Certain Acute Cases Developing Diabetes Sera from patients with acute insulino-dependent diabetes were anonymously collected from remaining volumes after routine testing for diagnostic and follow-up purposes. Sera from healthy blood donors were obtained from habilitated blood bank organisation.

The sera were tested according to the immunodetection technique using APO-H capture plates and specific ligand detection, as previously described in examples of the present invention.

The table below provides the mean optic density on triplicate tests, measured from sera of patients with acute diabetes (Diab.) and from representative blood donors (BD). anti-MSRV murine monoclonal antibody ligands were used:
One anti-Envelope (ENV) GNbAC1 (Geneuro, Switzerland).
One anti-Matrix and Capsid ployprotein (GAG): 2G5E12 (bioMérieux France).

The specific binding of these antibodies was revealed by a secondary anti-mouse antibody (Jackson, USA, ref. 115-035-146). The dilutions or concentrations used are indicated in the table below.

The results are significant when the ratio (P/N) of the mean optic density divided by the cut-off value (determined from healthy controls mean value plus two standard deviations—SD—of the corresponding series) are greater than one.

Such values are in bold and larger characters in the P/N 2 rows.

It can thus be evidenced that ten out of eighteen patients have significant antigenemia for at least ENV protein, detected by the Ligand murine monoclonal antibody. All "MSRV-positive" patients are detected by the two antibodies and have significant results for both GAG and ENV proteins.

Such results with coinciding detection of two different monoclonal antibodies targeting two different epitopes representing two different MSRV proteins (ENV and GAG), are obviously significant and meaningful in terms of association with MSRV as described elsewhere in the present invention, for the determination of MSRV-associated diseases.

Therefore, Type I or other inflammation-associated diabetes comprises a sub-group of patients whose disease pathogenesis can be caused by the pro-inflammatory and immunopathogenic effects of MSRV ENV protein.

TABLE 18

APOH-ELISA antigenamia results in patients with diabetes (Diab.) compared to healthy donors (BD). Cf. detailed comments in the text of the example.

| | | GNb AC1 1 ug/ml + Jackson 115-035-146 1/1000 | 2G5E12 080604CP01 1 ug/ml + Jackson 115-035-146 1/1000 |
|---|---|---|---|
| DIAB. | MORF | 0.061 | 0.066 |
| | GIRD | 0.014 | 0.020 |
| | THEP | 0.085 | 0.140 |
| | LOND | 0.045 | 0.096 |
| | LEGM | 0.030 | 0.034 |
| | ELAM | 0.089 | 0.085 |
| | NFDK | 0.118 | 0.122 |
| | GEOV | 0.088 | 0.120 |
| | FIOP | 0.021 | 0.052 |
| | VERV | 0.026 | 0.041 |
| | CHOM | 0.023 | 0.047 |
| | HAMH | 0.220 | 0.464 |
| | DJES | 0.035 | 0.040 |
| | PCTP | 0.047 | 0.066 |
| | MEST | 0.065 | 0.062 |
| | HMAA | 0.092 | 0.120 |
| | GIUM | 0.046 | 0.072 |
| | TRAF | 0.049 | 0.049 |

TABLE 18-continued

APOH-ELISA antigenamia results in patients with diabetes (Diab.) compared to healthy donors (BD). Cf. detailed comments in the text of the example.

| | | GNb AC1 1 ug/ml + Jackson 115-035-146 1/1000 | 2G5E12 080604CP01 1 ug/ml + Jackson 115-035-146 1/1000 |
|---|---|---|---|
| BD | GE3 | 0.025 | 0.049 |
| | GE4 | 0.035 | 0.070 |
| | GE5 | 0.017 | 0.037 |
| | GE6 | 0.027 | 0.058 |
| | GE7 | 0.036 | 0.039 |
| | GE8 | 0.047 | 0.054 |
| P/N 2 | MORF | 1.172 | 0.870 |
| | GIRD | 0.269 | 0.264 |
| | THEP | 1.633 | 1.845 |
| | LOND | 0.865 | 1.265 |
| | LEGM | 0.576 | 0.448 |
| | ELAM | 1.710 | 1.120 |
| | NFDK | 2.267 | 1.608 |
| | GEOV | 1.691 | 1.582 |
| | FIOP | 0.404 | 0.685 |
| | VERV | 0.500 | 0.540 |
| | CHOM | 0.442 | 0.619 |
| | HAMH | 4.227 | 6.116 |
| | DJES | 0.673 | 0.527 |
| | PCTP | 0.903 | 0.870 |
| | MEST | 1.249 | 0.817 |
| | HMAA | 1.768 | 1.582 |
| | GIUM | 0.884 | 0.949 |
| | TRAF | 0.942 | 0.646 |
| | Mean BD | 0.031 | 0.051 |
| | SD BD | 0.010 | 0.012 |
| | Mean MS | 0.064 | 0.094 |
| | SD MS | 0.049 | 0.099 |
| | Cut off 2SD | 0.052 | 0.076 |

P/N 2 = Optic density ratio calculated as the sample result divided by the Cut off value. The latter is determined with healthy donors as the mean of healthy group + twice its standard deviation.

Example 12

Unexpected Discovery of an Appropriate Animal Model for ENV-Induced Diabetes

1. Introduction

The non-obese diabetic SCID (NOD-SCID) spontaneous mutant mouse model has the SCID mutation transferred onto a diabetes-susceptible NOD background. Surprisingly, preliminary experiments conducted by the Applicant revealed that the primary immunisation of humanized NOD-SCID mice with ENV protein (25 μg) and murine MBP (protein and peptide) lead systematically to a rapid death of all animals tested, while all the humanized SCID mice that had received the same immunogens without the ENV protein (Mock-controls) survived. In a first step, we evaluated the deleterious effects of ENV protein in the NOD-SCID mice in a dose-response manner using clinical monitoring combined to a histological approach. In a second step, we assessed the beneficial effects of our chimeric IgG4 ligand in preventing the damage induced by ENV protein.

2. Evaluation of the Deleterious Effects of ENV Protein in NOD-SCID mice
  a. Materials and Methods
   a.1. Animals
  Six pathogen free SCID mice (6 to 8 week-old) were purchased from Charles River, France. Animals were maintained 3 per cage on a standard light-dark cycle with ad libitum access to food and water and were undisturbed for an 8-days period of acclimation. Special care was taken to ensure very clean housing conditions. Particularly, animals were housed in special cages equipped with filter lid.

a.2. Humanisation of NOD-SCID Mice

In order to obtain NOD-SCID mice, devoid of lymphoid immune system, with a grafted human immune system, mice were humanized with human peripheral mononuclear cells thus offering the potential to study the functional role of the human immune system in immunopathogenic animal models. This provides results much closer to the real human situation in terms of immunopathology and response to human pathogenic proteins, such as MSRV-ENV. Humanisation of mice was achieved according to the previously described protocol by Firouzi et al., 2003 except that animals were not gamma-ray irradiated and were not treated with anti-NK ligand because NOD-SCID mice are spontaneously depleted from NK cells. Blood (leuko-platelet layer, 45-50 ml) from 2 healthy controls was obtained from blood transfusion center (EFS) in Lyon. The quality and safety of blood was guaranteed by immunologic and haematological analysis. All the experimental procedures were performed under a laminar air flow and using sterile gloves. Human peripheral blood mononuclear cells (PBMCs) were obtained by a Ficoll gradient density separation method and were administered to NOD-SCID by an i.p. injection ($50 \cdot 10^6$ cells). Because blood of two different donors was used to humanize all animals, the same proportion of mice was humanized with each blood donor. It can here be already confirmed that no difference between animals grafted with either donor was seen in all future experiments, as described below.

3. Evaluation of the Deleterious Effects of ENV Protein in the NOD-SCID Mice

Injections of ENV Protein

On day 0 (P0), mice received a single intra peritoneal (i.p.) injection (0.5 ml) of ENV protein (PX'Therapeutics, France) with the following doses: 0.1, 1, 5, 10, and 20 µg. ENV protein was diluted in sterile Phosphate Buffer Saline (PBS) (Lonza, France). A single mouse received injection with PBS alone.

To avoid any decrease in ENV protein concentration and bioactivity, a second injection of ENV protein emulsified in 0.5 ml of incomplete Freund's adjuvant (Sigma, France) was achieved on P7. Each mouse received a single subcutaneous injection in the neck. The doses of ENV protein used for each mouse were the same as for the first injection on P0.

A third s.c. injection of ENV protein emulsified in mineral oil diluent—"IFA"—(0.5 ml) was performed in the neck on P14. The same day, mice received an i.p. injection of 200 ng (0.5 ml) of pertussis toxin—"PTX"—(Wako, Germany) per animal to transiently open the blood brain barrier for the passage of extra-CNS immune cells.

Clinical Assessment

The general health status (aspect of the coat, gait in the home cage, posture) and the weight of animals were monitored 5 days per week during from P14 to P37.

Histological Examination

Brain and internal organs of all dead animals were removed and conserved in formol (10%) for subsequent histological examination.

b. Results

1. Clinical Monitoring

Figure 13:
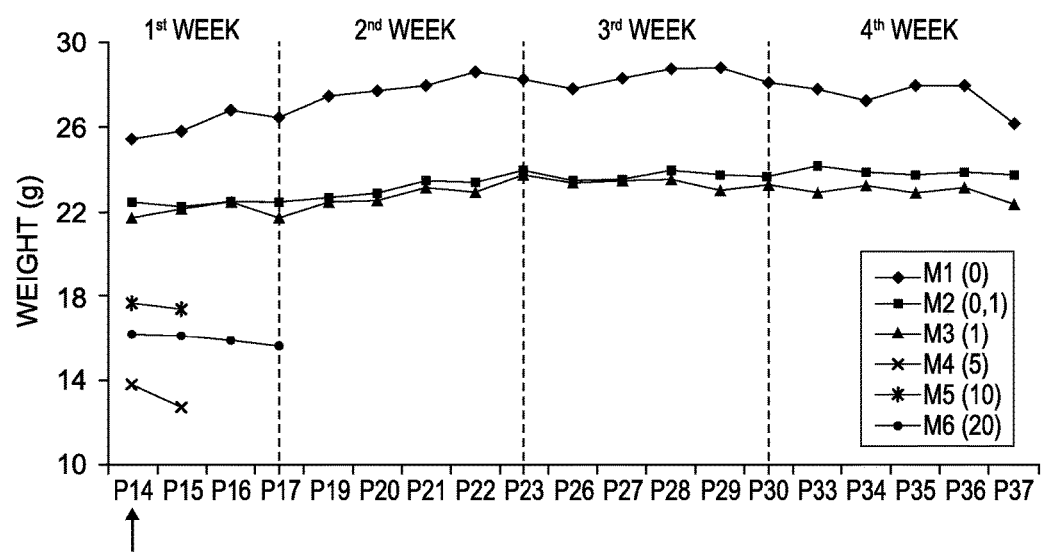

During the first few days following the injection of ENV protein emulsified in IFA and PTX, all mice that had received the highest doses of ENV protein displayed a body weight decrease (see FIG. 13) associated with a strong worsening of their general health status as indicated by a low activity in the home cage and prostration behavior. Finally, all these mice died within the four days following the last injection. Interestingly, mice injected with lower doses of ENV protein showed a slight body weight increase associated with a good general health status despite a gradual emergence of mild bristling coat in the two remaining mice injected with the low doses of ENV protein.

During the week after the last injection, the body weight of surviving mice stabilised or slightly declined (see FIG. 13), but their general health status was unchanged.

During the second week after the last injection, surviving mice continued to gain weight (see FIG. 13) and their general health status stabilized.

2. Histological Examination

Study Aims

Histopathological study of pancreas from NOD mice M4, M5 and M6

Materials and Methods

Samples of pancreatic tissue, fixed in formalin, have been received. Tissue samples have been embedded in paraffin, cut in 5 µm-thick sections. Tissue sections have been stained with hematoxylin-eosin-saffron and examined with a light microscope. Representative numerized pictures have been taken Results M4 Pancreas:

the overall architecture of the pancreas is preserved.

Focal inflammatory lesions are present: they form small infiltrates, of polymorphic composition, with a predominantly perivascular and periductular distribution. There is no significant alteration of the exocrine pancreas. Lesions of the endocrine islets are observed: inflammatory cells are present along their periphery and apoptotic endocrine cells are visible.

M5 Pancreas:

Pancreatitis is present. Large inflammatory infiltrates are present within the exocrine pancreas and are associated with focal acinar cell necrosis. Fibrinoid necrosis is sometimes present.

M6 Pancreas:

Severe lesions are present. Large, confluent areas of necrosis are present in the pancreas and result in the complete necrosis of a large number of acinar cells. In addition, the inflammatory lesions also involve the peripancreatic adipose tissue, with foci of cytosteatonecrosis. The histological aspect is typical of acute, necrotizing pancreatitis.

In summary:

Focal and mild inflammatory lesions in pancreas from M4.

Acute pancreatitis of moderate intensity in pancreas from M5.

Severe acute necrotizing pancreatitis in pancreas from M6.^ c. Discussion

Overall, our results suggest that ENV protein injection is lethal in NOD-SCID mice only for doses higher than 5 µg. Since the animals injected with high doses of ENV protein displayed a deterioration of their general health status before the injection of PTX, it is unlikely that major CNS damage could explain the deleterious effects of ENV protein observed in NOD-SCID mice. It is more likely that ENV protein has triggered major dysfunction in one or several other organs leading to the death of animals. Since NOD-SCID mice carry diabetes-susceptible background, the histological status of the pancreas of dead animals as presented above, is highly suggestive of pancreas inflammation induced by ENV. Interestingly, the lowest lethal dose induces lesions in beta-islets and endocrine pancreas only, which clearly corresponds to diabetes lesions and is sufficient to explain mice death at this dose, in the absence of insulin-secreting cells eliminated by ENV-induced inflammation.

With higher doses, it appears that we are probably beyond the relative doses/weight that could be encountered in human diabetes and that such high levels of ENV induce much larger inflammation gaining the whole Pancreas, including the exocrine part, in acute necrotizing pancreatitis. Nonetheless, these observations are relevant for Pancreatitis, which is here shown to occur when higher doses of MSRV-ENV proteins are injected.

4: Monitoring of Glycaemia after Repeated Injections of ENV Protein in NOD-SCID Mice A. Introduction In a previous experiment, we have shown that repeated subcutaneous injections of 5 µg of ENV protein in humanized NOD-SCID mice can lead to death of corresponding animal group that could be linked to an acute pancreatic islet 13 cells destruction. To prevent ambiguous interpretation of glycaemia kinetics evolution in conditions causing sudden death of animals, in the present study we have used repeated injections of sublethal dose of ENV protein for studying the glycaemia of humanized NOD-SCID mice.

B. Materials and Methods

1. Animals see above 2.a.1

2. Humanisation of NOD-SCID Mice see above 2.a.2

3. Injections of ENV Protein

In this study, mice were injected once per week (P0, P9, P16 and P23) for 4 weeks. For each time point, two mice received a subcutaneous neck injection of 2.5 µg of ENV protein (PX'Therapeutics, France) emulsified in 0.5 ml of incomplete Freund's adjuvant (Sigma, France). The two remaining mice (control mice) received a subcutaneous neck injection of 0.5 ml of incomplete Freund's adjuvant.

4. Glycaemia Measurement

At P0 and P30, blood samples were collected from the lateral tail vein in conscious animals. Blood glucose concentrations were assessed using a glycaemia reader (Optium Xceed, Abbott, France).

C. Results

As expected with sub-lethal dose, mice that had received four injections of ENV protein were sill alive after the fourth injection despite the gradual emergence of mild bristling coat as previously described.

Figure 14:
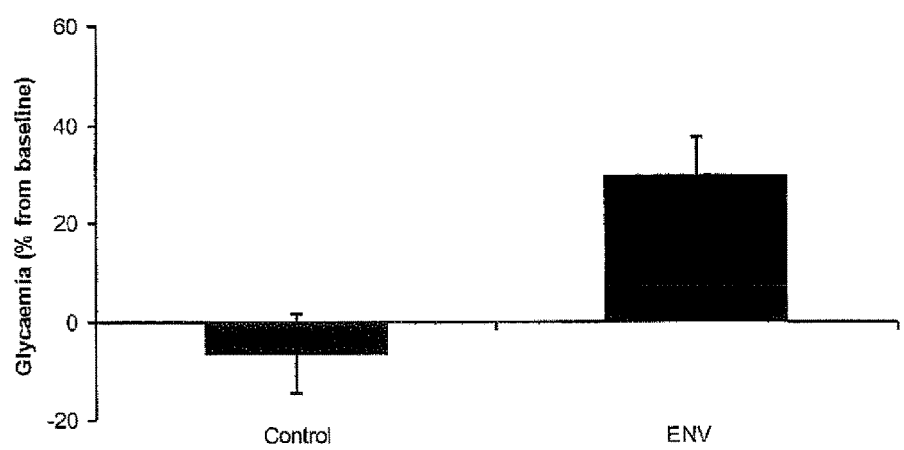

At P0 (Day of the first inject of ENV or of mock-solution in controls), no obvious difference could be detected between control and ENV-injected mice. Interestingly, at P30, the blood glucose concentration (Glycemia) of ENV-injected mice was found to be increased compared to control mice, whereas that of control mice was not different from their previous values at P0 (FIG. 14).

This glycemia variation in ENV-treated animals revealed quite significant of an evolution towards hyperglycemia in ENV-injected animals, which is a hallmark of human diabetes and corroborates previous histopathological findings.

Therefore, these resuts further validate our experimental conditions as a relevant pre-clinical model to study ENV-targeting therapeutic drugs in diabetes.

Example 13

Evidence of a Therapeutic Effect of the GNb AC1 Ligand, Under the Form of a Chimeric IgG4 Ligand, in the Prevention of the Emergence of Diabetes-Related Disease in an Appropriate Animal Model 1. Materials and Methods a.1. Animals This study was conducted on the two surviving mice injected with low doses of ENV protein (0.1 and 1 µg) used in the previous experiment.

2. Experimental Procedures

Because the repeated injection of 5 µg of ENV protein has been shown to lead to a rapid death of the mouse, we used this challenging dose for the assessment of the beneficial effects of our ligand. As described in the previous experiment, mice received three s.c. injection of ENV protein emulsified in IFA (0.5 ml) in the neck at P50, P57 and P64. For each time point, mice received on the same day a single i.p. injection (0.5 ml) of 100 µg of GNb AC1 IgG4 chimeric ligand. The clinical status and the weight of each mouse were monitored 5 days per week from P50 to P81.

3. Results

The observation of the treated animals until 120 days of follow-up clearly indicates that these animals had long-term survival. Thus, the GNbAC1 injection has protected them and made them survive to the deathly dose of MSRV-ENV injected three successive times.

During this follow-up period, their general health status remained good and the continued to gain weight, in the physiological range (no obesity was observed).

It can be concluded, in this animal model corroborating diabetes lesions and furthermore, which can lead to Pancreatitis that the GNb AC1 IgG4 ligand has been efficient against the deathly doses of MSRV ENV and has therapeutic effects of interest in diseases such as diabetes or pancreatitis associated with inflammation and MSRV ENV expression or antigenaemia.

Example 14

Design, Construction and In Vitro Analysis of a GNb AC1 Humanized Antibody with IgG4 Isotype Chains Comprising 6 CDR Amino Acid Sequences from the Ligand, with (i) First-Step Optimizations for the Insertion into the Humanized IgG4 Variable Chains, (ii) the Selection of the Best Combination of CDR Sequences for the Optimal Target (ENV-Protein) Binding Activity in IgG4 Vector, and (iii) Selection of Optimizations for IgG4 Stable Expression in CHO Cells A. Design of Molecular Constructs, Production and Selection of the Constructs, for Obtaining a Humanized and Stabilized IgG4 Antibody Vector with the Ligand 1. Analyses of Fv Regions of GNb AC1 Murine Anti-ENV Antibody To find suitable human frameworks for humanization of GNb AC1 murine antibody, amino acid sequences of GNb AC1 heavy and light chain Fv regions were aligned with human antibody germline gene database from Panorama Research Institute (1230 Bordeaux Drive, Sunnyvale, Calif. 94089, USA). Top hits of the human germline V genes were identified as human V gene candidates.

From the database search, human VH1-46 and VH1-69 genes were identified to have the closest sequences to the murine GNb AC1 heavy chain. We therefore selected VH1-69 as human frameworks for humanization. Using the same database, we identified human JH4 sequence to be used for framework 4 in the humanized heavy chain.

For the antibody light chain, VK1-5, VK3-11, VK1-33, VK1-39 showed high homology to the murine antibody light chain. We therefore choosed VK1-39 for the humanization of the light chain. Using the same method, we identified JK4 for construction of framework 4 of the human antibody light chain.

To define CDR regions suitable for grafting into the human VH chain of the humanized antibody, we re-evaluated an adapted and optimized delineation of these CDR regions within the original murine antibody variable heavy chain. We thus used a combination of Kabat Definition and Chothia Definition (Johnson G, Wu T T. Kabat Database and its applications: future directions. Nucleic Acids Res 2001; 29: 205-6. and Chothia C, Gelfand I, Kister A. Structural determinants in the sequences of immunoglobulin variable domain. J Mol Biol 1998; 278: 457-79), as our Preferred Definition. In summary, Chothia definition privileges conformational variability whereas Kabat definition privileges sequence variability. The CDR regions of the GNb AC1 murine antibody heavy chain are shown in FIG. 15 (SEQ ID No. 33, 34 and 35), with selection of the preferred regions for functional insertion into the human IgG4 Variable Heavy chain (VH) according to the previously described preferred definition.

To define CDR regions suitable for grafting into the human VL chain of the humanized antibody, we also re-evaluated an adapted and optimized delineation of these CDR regions within the original murine antibody variable light chain. We thus used a combination of Kabat Definition (Johnson G, Wu T T. Kabat Database and its applications: future directions. Nucleic Acids Res 2001; 29: 205-6) and Contact Definition (Panorama Research Institute, CA, USA). After evaluation for the murine antibody light chain, we used Kabat definitions as our Preferred Definition to define CDR regions. The selected CDR regions for the antibody light chain are shown in FIG. 16 (SEQ ID 36, and SEQ ID 38).

2. Humanized Heavy Chain Variable Region

Based on murine antibody CDRs and human germline VH1-69 gene, seven VH sequences were designed for humanization of the GNb AC1 heavy chain. They were designated as H1, H2, H3, H4, H4A, H4B, and H4C. The DNA fragments of these V regions were synthesized and fused to the 5' of a human IgG4 constant region cDNA to create 7 full-length IgG4 heavy chains. The full-length IgG4 heavy chains were inserted into a pCMV plasmid backbone downstream of a CMV promoter (Cf. example 4). The clones that contained correct heavy chain inserts were identified by restriction enzyme digestion and their DNA sequences were consequently confirmed by sequencing analyses and correspond respectively to SEQ ID No. 39 to SEQ ID No. 45.

3. Humanized Light Chain Variable Regions

Based on the murine antibody light chain CDRs and human germline VK1-39 gene, three humanized VL sequences were designed and synthesized. These sequences were designated as VK1, VK2, and VK3. The three VK DNA fragments were fused to the kappa constant region in a pTT5 plasmid backbone containing human kappa chain sequence. Each light chain open reading frame is driven by a CMV promoter. In order to increase gene expression, the kappa light chain sequence also includes an intron in the junction of VL and light chain constant regions. Plasmid clones with correct inserts were identified by restriction enzyme digestions and their sequences were confirmed by DNA sequencing analyses correspond respectively to SEQ ID No. 46 to SEQ ID No. 48.

4. Expression of Humanized Antibodies Variants.

To express antibodies, the plasmids of seven heavy chains and three light chains were purified using the plasmid DNA purification Maxi kit (Qiagen). In addition, the plasmids for chimeric GNb AC1 IgG4 heavy chain and chimeric GNb AC1 kappa light chain (Provided by GeNeuro) were purified using the same kit. Chinese hamster ovary (CHO) cells were cultured in serum free medium (Invitrogen) in 6-well plates and co-transfected with various combinations of heavy and light chain plasmids at 1:1 DNA ratio. Transfections were carried out using the Invitrogen freestyle Max transfection reagent. A total of 32 transfections were performed, which included the combinations of 8 heavy chains (7 humanized heavy chains plus one chimeric heavy chain) and four lights chains (3 humanized light chains plus one chimeric light chain). On day 3 post-transfection, cell culture supernatants were harvested. Antibody concentrations in the supernatants were determined by a human IgG4 ELISA assay in which the purified chimeric GNb AC1 IgG4 antibody (supplied by GeNeuro) was used to generate a standard curve.

5. Preliminary Screen of Humanized Antibody Variants

To evaluate humanized antibody variants, we used the chimeric antibody generated from co-transfection of chimeric heavy and chimeric light chains in CHO cells as a benchmark/positive control for binding activity to ENV protein. Since the chimeric GNb AC1 antibody and all humanized antibody variants are in IgG4 format, an ELISA-based binding assay with immobilized MSRV ENV protein can been conveniently used to evaluate relative antibody binding activities. In this binding assay, ELISA plates were coated with purified recombinant ENV protein (provided by GeNeuro) at 1 μg/ml. The plates were blocked with 1% BSA and anti-ENV antibodies with various dilutions were applied to the wells. Bound antibodies were detected by a secondary anti-human IgG Fc antibody conjugated with HRP, followed by development of color with HRP subtract (KPL). Using this assay, we showed that the chimeric anti-ENV IgG4 antibody has very good binding activity to immobilized ENV (FIG. 17).

Using the same binding assay, we evaluated supernatants harvested from CHO culture that were transfected with various combinations of humanized heavy and light sequences. Two criteria were set to determine the best antibody:

humanized antibody should have binding activities close to the chimeric GNb AC1 antibody;

humanized antibody should have a reasonable expression level, i.e. >100 ng/ml, in the supernatants after co-transfection of heavy and light chain plasmids.

Based on these selection criteria, H2/VK3 was selected as the best antibody for its good binding activity (FIG. 18) and expression (>1 ug/ml in 6-well plate). H4/VK3 was the second best antibody, since its binding activity to ENV protein is lower than H2/VK3 (FIG. 19). The third antibody, H1/VK3 has good binding activity, but is poor in antibody expression (<10 ng/ml in 6-well plate) (data not shown). Based on this preliminary screen, we decided to focus on H2/VK3 in further evaluation.

6. Further Evaluation of H2/VK3

After the preliminary screen, we further compared H2/VK3 with chimeric anti-ENV IgG4 antibody in the binding assay using normalized antibody concentrations. The concentration of antibody H2/VK3 in supernatant was carefully measured with our IgG4 ELISA using the purified chimeric GNb AC1 antibody as a standard. H2/VK3 antibody in supernatants and purified chimeric GNb AC1 IgG4 antibody were diluted to the same concentrations and compared in the ENV-binding ELISA assay. The assay showed that the humanized H2/VK3 antibody has almost identical ENV-binding activity as chimeric IgG4 anti-ENV protein (FIG. 20).

Next, we scaled up expression of H2/VK3 so that a sufficient amount of H2/VK3 antibody could be purified. pCMV H2 and pTT5 VK3 plasmids were prepared using plasmid purification maxi kit (Qiagen). CHO cells were cultured in serum-free CHO medium and transfected with two plamsids using Invitrogen Freestyle Max transfection reagent. Five days post-transduction, cell culture supernatants were harvested and centrifuged at 3400 rpm for 15 minutes. The supernatants were then passed through a protein A column (GE), washed with PBS and eluted with pH 3.5 elution buffer. Protein-containing fractions were pooled and concentrated to a proper volume by Amicon spin columns with a molecular weight cut off of 10 kD. Antibody concentrations were determined by human IgG4 ELISA and verified by Bradford protein assay (Bio-Rad). The purified H2/VK3 antibody was checked in non-reducing SDS-PAGE gel and a single band at molecular weight about 150 kD was observed (FIG. 21).

Finally, the purified H2/VK3 was compared to the purified chimeric GNb AC1 antibody in the ENV-binding assay. Results showed that purified H2/VK3 has a binding activity almost identical to the purified chimeric antibody (FIG. 22). Based on these data, we concluded that H2/VK3 met our criteria and was selected as humanized GNb AC1 antibody. Given previous binding activity data (FIGS. 3-6 and 8) the 6 CDR sequences necessary to maintain the Ligand activity within the humanized antibody are inserted in the amino acid sequences of the H2 and VK3 chains of the selected humanized IgG4 antibody vector (FIG. 22) and are set forth in SEQ ID No. 49 to SEQ ID No. 54.

They have been optimized by selection and mutation from the CDR sequences analyzed in the murine VH and VL chains, which were first chosen for adequate insertion within the primary human VH and human VL constructs (SEQ ID 33-38). Amino acid sequences for the selected humanized H2 heavy chain and VK3 light chain (for the selected humanized IgG4 construct) and their remaining murine residues are also shown in FIG. 23.

We produced 1 mg of H2/VK3 complete humanized antibody construct from CHO cells by co-transfection of pCMV H2 and pTT5 VK3 plasmids in serum-free CHO medium and this H2/VK3 antibody was purified by a Protein A column.

7. Generation of Humanized Anti-ENV mAb with S241P Mutation

IgG4 antibodies are sometimes found to be functionally monovalent in vivo. Recent studies have elucidated that this is due to the in vivo exchange of IgG half-molecules (one H-plus one L-chain) among IgG4 molecules. This process results in bispecific antibodies that in most situations will behave as functionally monovalent antibodies (Aalberse and Schuurman 2002, IgG4 breaking the rules, Immunology. 2002, 105:9-19). This is caused largely by instability of the interchain disulphide bridges due to the change of P to S at the residue position 241 (hinge region) and will likely reduce antibody specificity and potency. In order to avoid this problem, we have performed 3D protein evaluation of possible amino acid substitution (using software programs such as those available on the NCBI-ENTREZ website with, e.g. Protein Cn3D viewer, or such as M CLC Main Workbench, CLC Bio company, Aarhus, Denmark, or those developed in Panorama Research Institute, CA, USA). We have thus conceived that an original modification of the primary nucleotide sequence consisting in replacing the existing Serine (S) residue in position 241 by a Proline (P) residue, from optimized nucleotide sequence encoding it within the nucleotide construct, was a solution to an eventual instability of the IgG4 antibody vector with the Ligand. Hence, site-directed mutagenesis was performed and the PCR product was cloned into the pCMV plasmid, designated as H2 S241P. The DNA sequence of the muted H2 heavy chain was confirmed by sequencing analysis. This optimization is now combined with modification of the kappa light chain sequence with the inclusion of an intron in the junction of VL and light chain constant regions, as already mentioned above, to increase gene expression.

This original combination of sequences optimized from previously selected clones by nucleotide mutations or insertions with influence on the primary aminoacid structure or on the production rate of the final product is shown in FIG. 24, in which sequences corresponding to the IgG4 antibody product with the aminoacid composition and its inherent structure provide an optimized, stable and highly expressed vector for the Ligand of the present invention, preserving its functional binding properties for the target ENV protein antigen. It shows the final sequences of the anti-ENV humanized antibody heavy chain H2 S241P, with its encoding nucleotide sequence (SEQ ID 55) and its amino acid sequence (SEQ ID 56). It also shows the final sequences of the anti-ENV humanized antibody light chain VK3 with its encoding nucleotide sequence (SEQ ID 57), in which the intron is underlined: (SEQ ID 58). The spliced nucleotide sequence of the light chain VK3 without intron follows (SEQ ID 59). Last shown is the encoded amino acid sequence corresponding to the finally optimized light chain VK3 (SEQ ID 60).

Finally we produced 2 mg of the final version of the humanized antibody with S241P mutation from CHO cells. pCMV H2 S241P and pTT5 VK3 plasmids were purified by Qiagen plamsid DNA Maxi kit. CHO cells were cultured in serum-free CHO medium and transfected with the pCMV H2 S241P and pTT5 VK3 plasmids using Freestyle transfection Max reagent (Invitrogen). After 5 days, cell culture supernatants were harvested and centrifuged at 3400 rpm for 15 minutes. Antibody protein was purified using protein A column (GE).

B. Amino Acid and Nucleotide Sequence Optimized for CHO Cell Expression of Chimeric and Humanized IgG4 Antibody Vectors with the Ligand B1. Protein and Codon-Optimized (for CHO Cell Expression) Nucleotide Sequences of the Chimeric and Humanized Version of Antibody mAb GNb AC1

B1.1 Chimeric GNb AC1

The sequence corresponding to chGNb AC1 IgG4 mature protein is set forth in SEQID 61.

The sequence corresponding to chGNb AC1 LC mature protein is set forth in SEQ ID 62.

B1.2 Humanized GNb AC1

The corresponding sequence of huGNb AC1 IgG4 mature protein is set forth in SEQ ID 63.

The corresponding sequence of huGNb AC1 LC mature protein is set forth in SEQ ID 64.

B2. Nucleotide Sequences of the Humanized Light and Heavy Chain of GNb AC1 Including Plasmid Sequences The nucleotide sequences of huGNb AC1 LC is set forth in SEQ ID 65

The nucleotide sequences of huGNb AC1 IgG4HC is set forth in SEQ ID 67.

C. In Vitro Complementary Analyses of the Binding Activity of the Selected Humanized IgG4 Ligand (Stabilized and Codon-Optimized Humanized IgG4 Antibody Vector).

C1. Biochemical Antibody Binding Analyses.

Protocol: Incubation 2 h at 37° C. ENV in bicarbonate 50 mM pH9.6 buffer—Detection with antibodies diluted in PBS BSA 1% for 1 h at room temperature—Detection with secondary anti mouse and anti human antibody labelled with peroxydase respectively (ref 115-035-146 and ref 109-035-088, Jackson, USA) diluted 1/1000 in PBS BSA 1% and incubated for 1 h at room temperature. Revelation is made by adding OPD substrate and reading optic density with a spectrophotometer after 30 min (Washing steps with PBS are performed between every step).

TABLE 19

Dose-response binding kinetics of GNb AC1 Humanized antibody with a target protein, MSRV-ENV.

ENV-T 7A 1 ug/ml
anti human 109-035-088 Jackson 1/1000 or anti mouse 115-035-146 Jackson 1/1000

|  |  | HuMAb GNbAC1 Exp # 1 | HuMAb GNbAC1 Exp # 2 | GNbAC1 murine SQ08AK111 | GNbAC1 IgG1 chimeric Polymun batch 3 | GNbAC1 IgG4 chimeric Polymun batch 3 | 2G5E12 murine 080604CP01 |
|---|---|---|---|---|---|---|---|
| MAbs concentration [ug/ml] |  | 2.583 | 2.454 | 2.001 | 2.539 | 2.375 | 0.114 |
|  | 0.5 | 2.458 | 2.694 | 1.854 | 2.54 | 2.493 | 0.041 |
|  | 0.25 | 2.141 | 2.248 | 1.211 | 2.638 | 2.166 | 0.04 |
|  | 0.125 | 1.848 | 1.897 | 0.945 | 2.442 | 1.806 | 0.043 |
|  | 0.0625 | 1.316 | 1.578 | 0.585 | 2.508 | 1.66 | 0.041 |
|  | 0.03125 | 0.729 | 0.894 | 0.406 | 1.979 | 1.259 | 0.073 |
|  | 0.0156 | 0.501 | 0.52 | 0.166 | 1.274 | 0.777 | 0.042 |
|  | 0.0078 | 0.286 | 0.324 | 0.13 | 0.85 | 0.474 | 0.043 |

MAbs 1 ug/ml
anti human 109-035-088 Jackson 1/1000 or anti mouse 115-035-146 Jackson 1/1000

|  |  | HuMAb GNbAC1 Exp # 1 | HuMAb GNbAC1 Exp # 2 | GNbAC1 murine SQ08AK111 | GNbAC1 IgG1 chimeric Polymun batch 3 | GNbAC1 IgG4 chimeric Polymun batch 3 | 2G5E12 murine 080604CP01 |
|---|---|---|---|---|---|---|---|
| ENV concentration [ug/ml] | 1 | 2.576 | 2.602 | 2.221 | 2.519 | 2.67 | 0.053 |
|  | 0.5 | 2.501 | 2.346 | 1.867 | 2.533 | 2.26 | 0.084 |
|  | 0.25 | 2.183 | 1.719 | 1.418 | 2.273 | 2.296 | 0.087 |
|  | 0.125 | 1.728 | 1.48 | 0.975 | 1.822 | 1.558 | 0.093 |
|  | 0.0625 | 1.27 | 1.4 | 0.837 | 1.855 | 1.548 | 0.081 |
|  | 0.03125 | 0.907 | 0.703 | 0.367 | 1.6 | 1.095 | 0.091 |
|  | 0.0156 | 0.547 | 0.403 | 0.186 | 0.888 | 0.71 | 0.09 |
|  | 0.0078 | 0.36 | 0.211 | 0.111 | 0.642 | 0.313 | 0.082 |

These results clearly show that the humanized IgG4 antibody, in two experiments, has reproducible dose-response kinetics with either fixed ENV-protein target and antibody serial dilutions (upper part of the table) or fixed antibody concentration and target protein dilutions (Lower part of the Table). They are equivalent to that of the same chimeric antibody isotype, but much better than the original GNb AC1 antibody, whereas no significant binding kinetics is seen for the irrelevant control antibody (2G5E12).

C2. PBMC Reactivity Test
Materials and Methods: See example 6.

TABLE 20

Inhibition of Il-6 and IFN-γ pro-inflammatory cytokines in PBMC cultures with MSRV ENV protein, by GNb AC1 Ligand inserted in both Humanized and Chimeric IgG4 antibody vectors.

| Proteins | MAbs (ratio 10/1) | IL-6 24 h | IFN-g 72 h |
|---|---|---|---|
| ENV (EN-T 10A 0.1 ug/ml) | No Antibody | 4363 | — |
|  | Hu-GNb AC1 # 1 | 2910 | — |
|  | GNb AC1 chim IgG4 batch 3 | 2274 | — |
| ENV (ENV-SU 4A 0.5 ug/ml) | No Antibody | — | 336 |
| No ENV | Hu-GNb AC1 # 1 | — | 46 |
|  | GNb AC1 chim IgG4 batch 3 | — | 384 |
|  | — | 695 | 13 |
| LPS | — | 26039 | 212 |

NB. Background signal without ENV is shown below (No ENV) and control positive induction by bacterial LPS is shown at the bottom These results evidence a significant inhibition of:

(i) Interleukine 6 (IL-6) induction by MSRV ENV protein peaking at 24 h in Peripheral blood mononuclear cell cultures (with complete ENV protein, ENV-T, used at 0.1 microg/lm) is significantly inhibited in the presence of both Humanized and Chimeric antibodies.

(ii) Interferon gamma (IFN-γ) induction by MSRV ENV protein peaking at 72 h in Peripheral blood mononuclear cell cultures (with surface fragment of ENV protein, ENV-SU, used at 0.5 microg/lm) is strongly inhibited in the presence of the Humanized antibody, but not in presence of the Chimeric antibody. It thus evidences the improved effect of humanized antibody on T-cell activation, compared to the chimerized antibody. In the latter chimeric vector, remaining murine VH and VL chains might elicit adverse immune activation through human T-cell recognition of xenoantigens (murine protein chains grafted in the framework). This does not occur with the selected Humanized IgG4 vector of the Ligand binding to ENV proteins. This difference is not seen with IL-6 at 24 h, as this does not imply specific antigen recognition (acquired immunity with T-lymphocytes) but only innate immunity activation, blocked by the Ligand when bound to the target immunopathogenic ENV proteins.

Example 15

The HERV-W Envelope Proteins from Chromosome 7q (Syncytin) and MSRV Particles Both Induce Pro-Inflammatory Responses on Immune and Astrocytes Cells that are Inhibited by Anti-MSRV-ENV Antibody GNb AC1 and its Chimeric IgG4 Construct with the Ligand A relationship between immunopathogenic features in humans and the biological effect of these ENV proteins has been raised. Because the sequences of MSRV-ENV and Syncytin share more than 81% sequence identity (Mallet, Bouton et al. 2004; Mameli, Astone et al. 2007), we investigated whether these two sister proteins could display similar pro-inflammatory effects. Since previous studies on peripheral blood mononuclear cells (PBMCs) and brain astrocytes had shown reactivity to either MSRV-ENV or Syncytin respectively, we have here performed parallel analysis on both cell types.

Methods

Proteins Preparation and Isolation

See Example 2

Cell Isolation and Preparation

Human PBMCs were isolated from healthy donor buffy coats (Transfusion Center—HUG—Geneva) by density gradient centrifugation over Ficoll-Paque.

Human astrocytes were ordered from InVivogen.

Cell Stimulation

PBMCs were plated in 24 or 48-well plates at a concentration of $1 \times 10^6$/well in 1 ml of medium consisting of RPMI Glutamax 1640 (Invitrogen) supplemented with 1% non essential amino acids, 1% penicillin/streptomycin, 1% sodium-pyruvate and 10% heat-inactivated FCS (BioWest). The cells were incubated at 37° C. in 5% CO2 in humidified atmosphere for 24, 48 or 72 h.

For cell-culture experiments, Syncytin, MSRV-ENV and LPS were preincubated in 100 µl of medium with the antibodies directed against ENV (GNb AC1 monoclonal mouse IgG, GeNeuro) for 1 h at 4° before to be added to the cells.

Cytokine Production Assays

Culture supernatants were harvested at 24, 48 or 72 h and stored at −20° C. before evaluation of cytokine production by ELISA. OptEIA ELISA kit from BD Bioscience for detection of human cytokines was carried out, according to the manufacturer's instructions.

Results

MSRV-ENV and Syncytin are Two HERV-W Related Proteins

In order to compare biological properties associated with HERV-W Syncytin envelope protein (Accession number NCBI AF072056.2) to that of MSRV-ENV (Accession number NCBI AF331500.1), we have expressed and produced the two proteins under similar conditions for the present study (Conditions described in Example 2).

To address and compare the biological effects of the two HERV-W related proteins, we have studied their effect in the induction of pro-Inflammatory cytokines. We found that stimulation with HERV-W ENV related proteins strongly upregulated pro-inflammatory Interleukin 6 (IL-6) astrocyte responses. Most importantly, this stimulation was not affected by an irrelevant antibody (not binding to either ENV), but was strongly inhibited by GNb AC1 murine antibody and by GNb AC1 Human Chimeric IgG4, which clearly demonstrates that our Ligand in either forms of antibody vector is inhibiting the pro-inflammatory effects of HERV-W ENV related variants, and not of MSRV-ENV only.

In FIG. 24, an example of this analogous biological effect is revealed by the dosage of IL-6 release in the culture supernatant in presence of each HERV-W ENV related protein. This is a specific effect, since also inhibited by GNb AC1 Ligand, in the form of murine or IgG4 chimeric antibodies. Thereby, a similar inhibiting efficiency of the Ligand on different HERV-W ENV related proteins is also evidenced.

In addition to astrocyte cells, which are involved in the local brain lesions and inflammation, we have shown the systemic immune effects of both MSRV-ENV and Syncytin, which stimulate the production of proinflammatory cytokines in human peripheral blood mononuclear cells (PBMC, i.e. Lymphocytes and monocytes) cultures.

Figure 25:
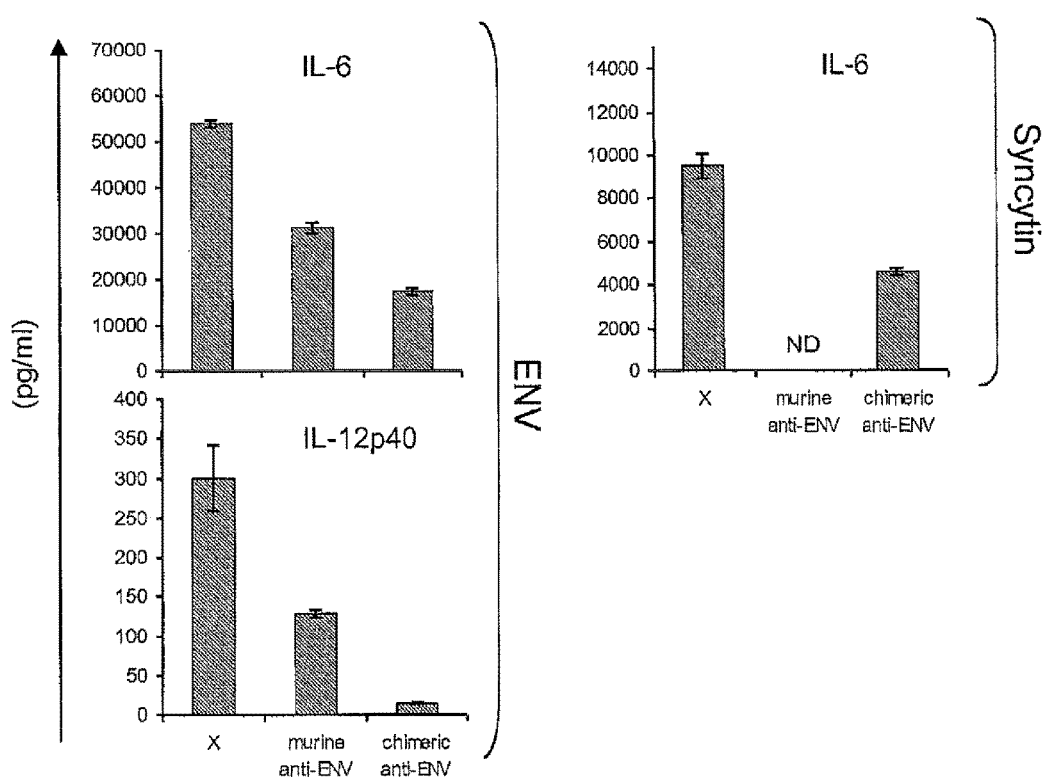

In FIG. 25, an example of this analogous biological effect on PBMC is validated by the detection of IL12 P40 (characteristic of innate immune response) and confirmed by the same dosage of IL-6 release in the culture supernatant for both HERV-W ENV related proteins. Moreover, as for the experiment with Astrocytes, this IL-6 release is also specifically inhibited by GNb AC1 Ligand, in the form of murine or IgG4 chimeric antibodies.

Example 16

The GNb AC1 Ligand and the Recombinant Human-Chimeric IgG4 GNb AC1 Antibody and the Humanized IgG4 Antibody Comprising the Ligand Bind to Both MSRV-ENV and HERV-W ENV 7q/Syncytin Proteins with Human Cell Glycosylations 1. Materials and Methods:

a. ENV bacterial recombinant protein was obtained as described in example 2.

b. Human Glycosylated MSRV ENV protein was produced for Geneuro, by P'X therapeutics, Grenoble, France, according to the following procedure: HERV-W-ENV analogous protein, named Syncytin, was produced with the same protocol.

Production Process of ENV Glycosylated Purified Protein from Human Cell Expression.

Transfection:

HEK-Freestyle cells were seeded at $10^6$ cells/mL and transfected with Env-MSRV_pMCMVHE/1 using 293Fectin transfection reagent.

Harvesting and Lysis:

Three days after transfection, cells are harvested and centrifuged. Cell pellet was resuspended in lysis buffer (PBS supplemented with anti-proteases) and cell disruption was performed by sonication.

Solubilization:

After centrifugation, the pellet was resuspended in solubilization buffer (50 mM Tris pH8, 100 mM NaCl, 2M Urea, 2% FOS-Choline10) and solubilized overnight at +4° C. under stirring.

Dilution Before Purification:

Next day, solubilized protein was diluted 4 times in dilution buffer (50 mM Tris pH8, 100 mM NaCl) and homogenize before purification.

Pool 1 EnvMSRV His tag Purification method: Ni sepharose Affinity Chromatography Ni sepharose affinity chromatography (GE Heathcare, 4 ml) is performed to purify His tagged Env-MSRV.

Equilibration buffer: 50 mM Tris pH8, 100 mM NaCl, 0.5% FOS-Choline10, 0.5M Urea.

Elution buffer: 50 mM Tris pH8, 100 mM NaCl, 0.5% FOS-Choline10, 0.5M Urea, 1M Imidazole.

Elution step: gradient on 30CV from 0% to 100% elution buffer.

Pool concentration: 7 fold using Amicon cut off 30 kDa

Pool 2 EnvMSRV His tag Purification method: Ni sepharose Affinity Chromatography This second affinity chromatography was performed using the flow-through of the first one as starting material=Load, diluted to 50 mM Tris pH8, 100 mM NaCl, 0.2% FOS-Choline10, 0.5M Urea Equilibration buffer: 50 mM Tris pH8, 100 mM NaCl, 0.2% FOS-Choline10, 0.5M Urea.

Elution buffer: 50 mM Tris pH8, 100 mM NaCl, 0.2% FOS-Choline10, 0.5M Urea, 1M Imidazole.

Elution step: gradient on 30CV from 0% to 100% elution buffer.

Quality Control:

SDS-PAGE quality control analysis was followed by Coomassie blue staining and Western-Blot analysis using GNb AC1 murine antibody. Nterminal sequencing confirmed the identity of the purified protein.

Batches Dialysis and Freezing

Env-MSRV two batches were dialysed against 50 mM Tris pH8, 100 mM NaCl, 0.5% or 0.2% FOS-Choline10 before addition of 10% of glycerol and freezing in liquid nitrogen.

c. Specific Binding Detection with ELISA Test

All ENV preparations were diluted in $CaCO_2$ buffer 50 mM pH9.6; they were incubated in Elisa Microplates wells for 2 h 37° C., for coating of the protein in the ELSA microplates. Nonetheless, due to lower production ratio, the concentration of coated Syncytin was inferior to that of MSRV-ENV.

Detection antibodies were diluted in PBS BSA 1% and incubated 1 h at room temperature in triplicate microplate wells. Peroxydase-labeled anti-mouse secondary antibody for murine monoclonal (ref 115-035-14 and anti-human secondary antibody for humanized and human-chimeric recombinants (ref 115-035-088) were diluted 1/1000 in PBS BSA 1% buffer and incubated 1 h at room temperature. OPD revelation for peroxydase was performed for 30 min followed by optical density reading at 490 nm. Washings between each incubation step were performed with 4, 4 and 6 washing cycles, respectively.

Figure 26:
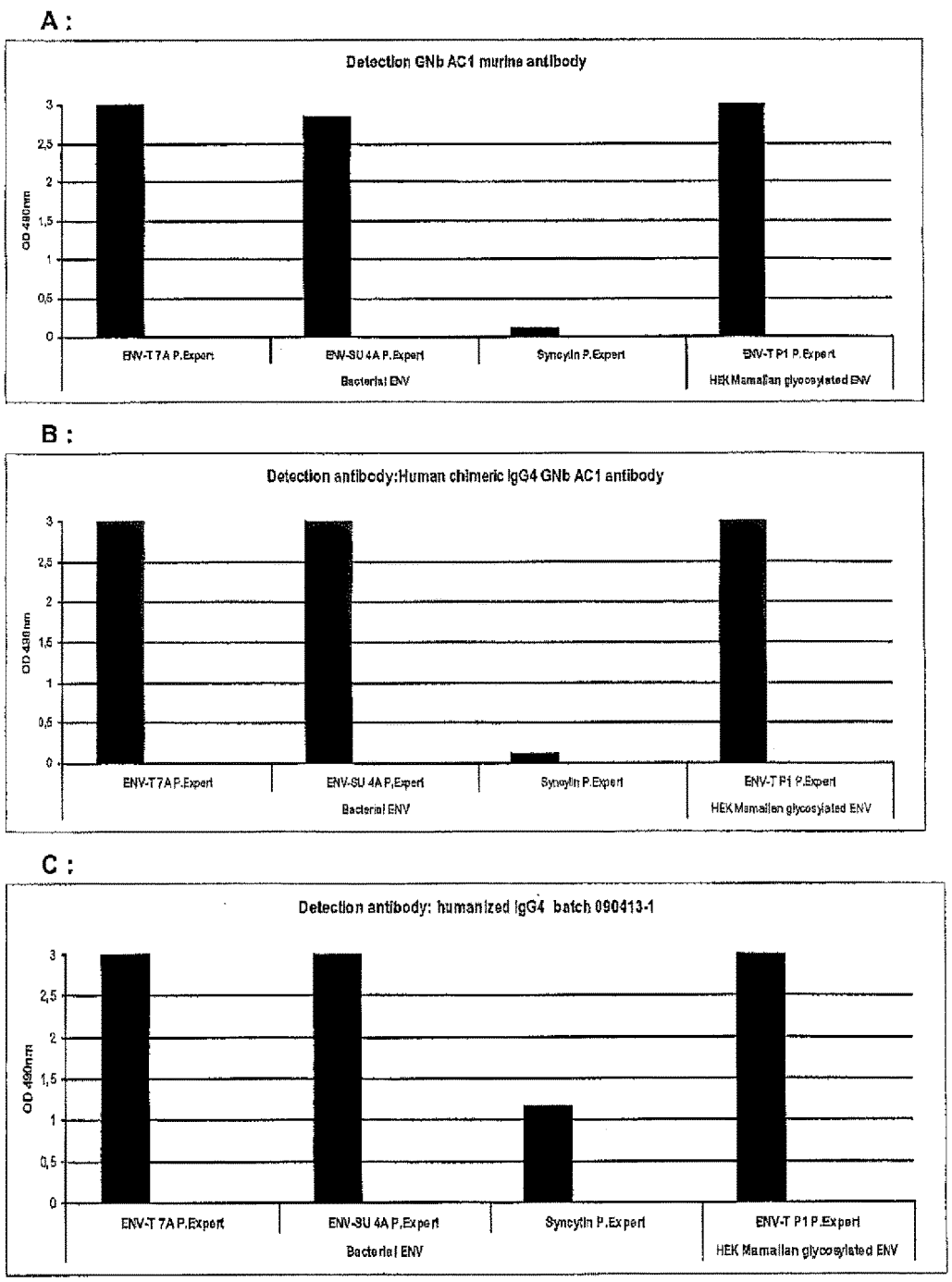

2. Results:

As can be seen from FIG. 26 below, both bacterial and Human-Glycosylated purified protein preparations of MSRV-ENV were readily detected by all antibody types with the Ligand (murine, Chimeric and humanized), yielding a good signal in luminometry optic-density measures. Interestingly, in the present ELISA conditions, only the Humanized antibody GNb AC1 Ligand yielded a good recognition of human glycosylated Syncytin, whereas, at this coating concentration, the murine and chimeric antibodies yielded low signals with Syncytin.

These results clearly show that the Ligand of the present invention, whatever its molecular vector used for binding to the target Epitope (murine, chimeric IgG4 or humanized IgG4 antibody), is found to efficiently bind to all forms of the target proteins comprising the Epitope, i.e. both bacterial and Human glycosylated ENV proteins and, particularly with the humanized antibody, both HERV-W related proteins, MSRV-ENV and HERV-W 7q ENV protein, also named Syncytine.

Thus, the therapeutic Ligand does bind to the human glycosylated forms of the target ENV protein.

Example 17

In Vivo Analysis of GNb AC1 Chimeric Antibody with IgG4 Isotype with Therapeutic Effect in an Animal Model of Schizophrenic Behavioral Abnormalities Induced by MSRV ENV I. Introduction In Example 8, we have demonstrated the presence of MSRV-ENV protein in the serum of patients with schizophrenia. This result underlines the necessity to explore the relationship between the presence of ENV protein and the emergence of brain alterations and behavioral deficits in adequate animal models. Neurodevelopmental theories of schizophrenia postulate that the disease is the behavioral outcome of a primary insult long before the illness is clinically manifested (Weinberger and Lipska, 1995; Lewis and Levitt, 2002). Thus, this physiopathological feature has to be taken into account in the design of appropriate animal models mimicking schizophrenia-related disorders.

II. Experiment 1: Effect of IgG4 Chimeric Antibody on the Behavioral and Anatomic Alterations Following Repeated Unilateral Intracerebroventricular Injection of ENV Protein in Rats that Had Received a ENV-Induced Immune Priming in the Early Adulthood A. Materials and Methods 1. Animals Male Sprague-Dawley rats (6 to 8 week-old) (n=8) were purchased from Charles River, France. Animals were maintained 3 per cage on a standard light-dark cycle with ad libitum access to food and water and were undisturbed for an 8-days period of acclimation. All procedures comply with the European Communities Council Directive of Nov. 24, 1986 (86/609/EEC) and the National Council Directive of Oct. 19, 1987 (87848, "Ministère de l'Agriculture et de la Forêt", France). All efforts were made to minimize the number of animals used and their suffering.

2. ENV-Induced Immune Priming

The first day, named "point 0" (P0), Rats were randomly assigned to a sham-injected group (n=2) with injection of Phosphate Buffer Saline (PBS) (Lonza, France) and ENV-injected group (n=6) with injection of 250 ng of recombinant ENV protein (His-ENVT-081206-1, PX'Therapeutics, France) dissolved in PBS.

Each rat was anesthetized by i.p. administration of a mixed solution of xylazine 10 mg/kg (Rompun®, Alcyon, France) and ketamine 80 mg/kg (Imalgène®, Alcyon, France). The hair was clipped from an area extending from between the ears to just anterior to the eyes. Ear plugs were inserted and the animal fixed in a stereotaxic instrument with the upper incisor bar 5 mm above the intra-aural line. The clipped scalp area was wiped with a chlorhexidine-based antiseptic solution (Alcyon, France) and an incision was made from between the ears to a point between the eyes. The skin was retracted with forceps and the underlying tissue, including the periosteum, was removed to expose an area of clear, dry skull (approximately 15×18 mm).

The plastic cannula (o.d.=0.457 mm and i.d.=0.267 mm) (Plastic One, USA) was aimed to be implanted in the right lateral ventricle. The cannula was mounted in the stereotaxic apparatus, the tip "zeroed" on the bregma. Hole was drilled through the skull over the lateral ventricle (antero-posterior, 0.92 mm; medio-lateral, +1.7 mm relative to bregma). The point of the cannula was positioned over the center hole so that the tip was even with the surface of the skull. The cannula was lowered 3.5 mm through the cerebral cortex into the lateral ventricle.

For each rat, the injection of PBS alone or with ENV protein was achieved via a stainless steel injector, placed in and projecting 0.5 mm below the tip of the cannula. The injector was connected by polythene tubing to a Hamilton syringe (VWR, France) to manually dispense solutions over a 3-min period. The injector was withdrawn 3 min after the completion of ejection to prevent the flow of PBS or ENV protein along the injector track.

The wound was closed using surgical suture on a needle holder. Animals were allowed to recover in an individual cage for a 2 days-period. Then, the animals were randomly housed three per cage and were maintained undisturbed until further experiments.

3. Repeated Unilateral Intracerebroventricular Injection of ENV Protein after a Latency Period Eight months later, cranial cannulae allowing repeated intracerebroventricular (icv) injections were implanted in all rats.

The day of surgery (P0), each rat was anesthetized by i.p. administration of a mixed solution of xylazine 10 mg/kg (Rompun®, Alcyon, France) and ketamine 80 mg/kg (Imalgène®, Alcyon, France). The hair was clipped from an area extending from between the ears to just anterior to the eyes. Ear plugs were inserted and the animal fixed in a stereotaxic instrument with the upper incisor bar 5 mm above the intra-aural line. The clipped scalp area was wiped with a chlorhexidine-based antiseptic solution (Alcyon, France) and an incision was made from between the ears to a point between the eyes. The skin was retracted with forceps and the underlying tissue, including the periosteum, was removed to expose an area of clear, dry skull (approximately 15×18 mm.). Three holes were drilled, two approximately 7 mm anterior to the bregma on both right and left sides of the skull and the third 7 mm posterior to the bregma. Nylon screws (diameter=0.50 mm) (Plastic One, USA) were threaded to fit firmly into the holes to serve as anchors for the dental cement. Care was taken to preserve the dura in these procedures. The plastic cannula (o.d.=0.457 mm and i.d.=0.267 mm) (Plastic One, USA) was aimed to be implanted in the right lateral ventricle. The cannula was mounted in the stereotaxic apparatus, the tip "zeroed" on the bregma and a point marked 0.92 mm posterior and 1.7 mm lateral to the zero mark. A hole was made with a drill at this marked site. The point of the cannula was positioned over the center hole so that the tip was even with the surface of the skull. The cannula was lowered 3.5 mm through the cerebral cortex into the right lateral ventricle. With the cannula held in the chuck of the stereotaxic instrument, a small amount of dental caulk (Paladur®, Heraeus Kulzer, France) was built around the cannula and the anchoring screws. The wound was closed using surgical suture on a needle holder. The mounting needle was withdrawn when the dental material was set and the animal was allowed to remove from the stereotaxic apparatus.

The injections of PBS or ENV protein were achieved on the same day (P0) and 25 days (P25) after the implantation of cranial cannulae.

For each time point, PBS alone or 250 ng of recombinant ENV protein (His-ENVT-081206-1, PX'Therapeutics, France) was administered via a stainless steel injector, placed in and projecting 0.5 mm below the tip of the cannula. The injector was connected by polythene tubing to a Hamilton syringe (VWR, France) to manually dispense solutions (3 µl) over a 3-min period. The injector was withdrawn 3 min after the completion of ejection to prevent the flow of PBS or ENV protein along the injector track.

4. Systemic Administration of the IgG4 Chimeric Antibody

The day after the second recall of ENV protein (P26), ENV-injected rats were randomly selected to receive a single intraperitoneal (i.p.) injection of PBS (n=3) or 100 µg of the IgG4 chimeric antibody diluted in PBS (n=3).

5. In Vivo Magnetic Resonance Imaging (MRI)

The brain morphology of rats was examined at P12 and P37 by in vivo MRI. Rats were firstly anaesthetized with an approved system (TEM Sega, France) using isoflurane 3% inhalation with a flow of 0.6 l/min air with 30% oxygen. After induction, anesthesia was maintained with isoflurane gas at 1.5 to 2% and 0.6 l/min flow. Body temperature was controlled and maintained at 37±1° C. by using a circulating water heating pad. Breathing rate was monitored throughout the experiment. Rats were positioned in a prone position on a plastic bed (Bruker Biospec Animal Handling Systems, Germany) equipped with stereotaxic fixation (tooth bar and ear pins). A 22-gauge intravenous catheter was then placed in the tail vein of rats for subsequent injections.

Scanning was performed on a Bruker 7T Biospec system (Bruker, Germany) equipped with 400 mT/m gradient set, using a transmitting body coil (o.d.=112 mm and i.d.=72 mm) and a 25 mm diameter surface coil is used for signal reception. A quick gradient echo localiser with three orthogonal orientations and a 5 cm field of view is first used to identify brain regions and allows calculation of fixed spatial coordinates for following scans. Two rapid acquisitions with relaxation enhancement (RARE) sequences in the axial plane are performed. First T2-weighted images are acquired with spin-echo pulse sequencing using a repetition time (TR) of 4200 ms, a single echo with echo time (TE) of 36 ms, a 35714 Hz receiver bandwidth and 4 min scan time. Second T2-weighted images is acquired with spin-echo pulse sequencing using a TR of 3000 ms, two echoes with a TE of 17 ms and 51 ms, a 55555 Hz receiver bandwidth and 5 min scan time. For both sequences, a total of 30 slices (800 µm thick) was acquired with a field of view of 2.56 cm and an acquisition matrix size of 256×256 resulting in an in-plane resolution 100×100 µm.

To assess the dynamics of the cerebromeningeal and cerebroventricular barriers in rats injected with ENV protein, gadolinium-enhanced MRI method was used. Coronal precontrast T1-weighted images were acquired with fast low angle shot (FLASH) sequences and repetition time/echo time=2.2/1.4 ms. A total of 30 slices (800 µm thick) was acquired with a field of view of 2.56 cm and an acquisition matrix size of 256×192 resulting in an in-plane resolution 100×133 µm. Afterward, the animals received a bolus injection of gadolinium 0.5 M (Dotarem®, Guerbet, France) (1 mL/kg body weight). Postcontrast T1 scanning was performed 10 min after gadolinium administration in the same conditions as described above.

6. Behavioral Analysis

At P15 and P40, rats were tested for locomotor activity using an automated digiscan apparatus linked to a PC computer (Imetronic, Pessac, France). Locomotor activity was monitored in a photocell testing cage equipped with an array of four parallel horizontal infrared beams (two at the front and two at the back) positioned 0.7 cm above the floor to measure horizontal activity. The number of beam breaks was recorded automatically. Horizontal activity was expressed in term of cage crossovers (i.e. consecutive breaks on either side of the cage). The number of cage crossovers was continuously recorded and cumulated over 10-min intervals.

For all rats, locomotor activity was assessed in mild stress conditions (i.e. after exposure to a novel environment or after i.p. saline injection) and in an amphetamine challenge. All these tests were performed during inactive phase (light period). For the novelty test, rats were removed from their home cage and placed into an individual photocell cage and the locomotor activity was measured for 1 h. Then, rats received a saline injection (1 mL/kg, i.p.) and their locomotor activity was monitored for one additional hour. Finally, animals were injected with D-amphetamine (sulphate 1.5 mg/kg, i.p., Sigma Aldrich, A-5880, batch 90K3354) and their activity was recorded for two additional hours.

B. Results

1. In Vivo Magnetic Resonance Imaging a) After the First Recall Injection of ENV Protein At P12, qualitative analysis of T2-weighted images of most animals revealed large hypersignals corresponding to the lateral ventricles. Compared to classical MRI images of naïve rat brains, the enlargement of these hypersignals seen in the present study suggests a swelling of the lateral ventricles in the corresponding animals. Moreover, a stronger expansion of the right lateral ventricle (i.e. the injected one) observed in both sham and ENV-injected animals. The extent of hypersignals corresponding to the lateral ventricles observed in animals injected with ENV protein were different to those of animals injected with PBS suggesting that ENV protein triggered neuroinflammatory processes.

Comparisons of T1-weighted images acquired before and after gadolinium injection revealed differences in animals injected either with PBS or ENV protein. These results suggest that the cerebromenigeal and cerebreoventricular barriers can be altered 12 days after the intracerebroventicular (icv) injection of ENV protein.

b) After the Second Recall Injection of ENV Protein

As described after the recall injection of ENV protein, qualitative analysis of T2-weighted images obtained after the second recall injection (P37) revealed large hypersignals corresponding to the lateral ventricles in most animals. In sham rats, we did not detect any significant hypersignal (taking into account the increase of signal beyond the normal background signal of cerebrospinal fluid that is normally visualized by MRI inside brain ventricles), which corresponded to the lateral ventricles between the two time points. Strikingly, ENV-injected rats displayed a strong enlargement of these hypersignals after the second injection. Even more significantly, the hypersignals could extend to surrounding structures, particularly the hippocampus. The MR images obtained in ENV-injected rats treated with the IgG4 chimeric antibody revealed strong enlargement of the hypersignals corresponding to the lateral ventricles.

Interestingly, the extension of theses T2-weighted hypersignals in surrounding structures as the hippocampus was limited in ENV-injected rats treated with the IgG4 chimeric antibody. As the antibody was injected in the periphery of the central nervous system—CNS—(intraperitoneally) this latter point is highlighting the facts that:

1—immediate pro-inflammatory effects in cerebral ventricles relating exclusively to the particular protocol used for the present animal model, which implies a direct icv injection of the MSRV ENV protein, are not immediately inhibited by the IgG4 chimeric antibody Ligand injected more than 24 h after ENV icv injection and, thus, after initiation of local ventricle inflammation. It must be precised that local ventricle inflammation is not a major feature of pathogenesis in Psychosis and is most probably not involving neurobehavioral troubles in the present model. This immediate post-icv local inflammation, can thus be considered as a side-effect of the present model.

2—the relevant features known to be associated with Psychosis expression, such as pathogenic involvement of the hippocampus, are here inhibited in rats injected with the therapeutic Ligand of the present invention, under the form of a the human-chimeric IgG4 antibody injected after ENV icy injection, at distance of the CNS and in the periphery of the CNS. This is here evidenced by the inhibition of the extension of hypersignals, observed by MRI, from ventricles to the critical brain region of the hippocampus.

Comparisons of T1-weighted images acquired before and after gadolinium injection did not reveal any apparent differences in all groups. These results suggest that the cerebromenigeal and cerebreoventricular barriers do not seem to be further altered after the second recall injection of ENV protein.

In this first set of experiment, we showed for the first time that two icy recall injections of ENV protein can lead to neuroinflammatory processes in ventricular and hippocampal areas in rats that had received a ENV-induced immune priming in early adulthood. Strikingly, anatomic and functional impairments of the hippocampus are consistent with MRI studies reported in schizophrenic patients with long-term cognitive decline associated with neuronal loss and ventricular enlargement (Bornstein et al., 1992). Interestingly, hippocampal damage induced by repeated recall injections of ENV protein was inhibited by the administration of the human chimeric IgG4 antibody, after the induction of ENV-induced pathogenesis, which is consistent with a therapeutic effect of the Ligand when administered under the formulation of this chimeric antibody in a pre-clinical model of Schizophrenia.

III. Experiment 2: Assessment of Neurobehavioral Impairments Following Single Bilateral Injection of ENV Protein in the Hippocampus or the Lateral Ventricles of Rat A. Materials and Methods 1. Animals Male Sprague-Dawley rats (6 to 8 week-old) (n=6) were purchased from Charles River, France. Animals were maintained 3 per cage on a standard light-dark cycle with ad libitum access to food and water and were undisturbed for an 8-days period of acclimation. All procedures comply with the European Communities Council Directive of Nov. 24, 1986 (86/609/EEC) and the National Council Directive of Oct. 19, 1987 (87848, "Ministère de l'Agriculture et de la Forêt", France). All efforts were made to minimize the number of animals used and their suffering.

2. Bilateral Injection of ENV Protein in the Hippocampus or in the Lateral Ventricles The day of surgery (P0), rats were randomly assigned to a sham group (n=2) with injection of PBS (Lonza, France) and two test groups with icy (ENV-icv rats, n=2) or intra-hippocampal (ENV-hipp rats, n=2) injection of 250 ng of recombinant ENV protein (ENVT, batch 081206-1, PX'Therapeutics, Grenoble, France) dissolved in PBS.

Each rat was anesthetized by i.p. administration of a mixed solution of xylazine 10 mg/kg (Rompun®, Alcyon, France) and ketamine 80 mg/kg (Imalgène®, Alcyon, France).

The hair was clipped from an area extending from between the ears to just anterior to the eyes. Ear plugs were inserted and the animal fixed in a stereotaxic instrument with the upper incisor bar 5 mm above the intra-aural line. The clipped scalp area was wiped with a chlorhexidine-based antiseptic solution (Alcyon, France) and an incision was made from between the ears to a point between the eyes. The skin was retracted with forceps and the underlying tissue, including the periosteum, was removed to expose an area of clear, dry skull (approximately 15×18 mm).

The plastic cannula (o.d.=0.457 mm and i.d.=0.267 mm) (Plastic One, USA) was aimed to be bilaterally implanted in the lateral ventricle or in the hippocampus. The cannula was mounted in the stereotaxic apparatus, the tip "zeroed" on the bregma. Holes were drilled bilaterally through the skull over the lateral ventricle (antero-posterior, 0.92 mm; medio-lateral, ±1.7 mm relative to bregma) or the hippocampus (antero-posterior, 4.8 mm; medio-lateral, +5.0 mm relative to bregma). The point of the cannula was positioned over the center holes so that the tip was even with the surface of the skull. The cannula was lowered 3.5 mm through the cerebral cortex into lateral ventricle or 7.5 mm into the hippocampus.

For each rat, the injection of PBS alone or with ENV protein was achieved via a stainless steel injector, placed in and projecting 0.5 mm below the tip of the cannula. The injector was connected by polythene tubing to a Hamilton syringe (VWR, France) to manually dispense solutions over a 3-min period. The injector was withdrawn 3 min after the completion of ejection to prevent the flow of PBS or ENV protein along the injector track.

The wound was closed using surgical suture on a needle holder. Animals were allowed to recover in an individual cage for a 2 days-period. Then, the animals were randomly housed three per cage and were maintained undisturbed until further experiments.

3. Behavioral Analysis

The locomotor response of rats was tested in mild stress conditions in an open-field using three paradigms: novelty, saline injection and restraint stress. Locomotor response to novelty was tested at P5, P6, P7, P11 and P12, while the locomotor activity after saline injection and restraint stress was tested once at P11 and P13, respectively.

The open field apparatus consisted of a quadratic box (80×75 cm×40 cm) made of wood, which was dimly illuminated. The floor of the open-field was divided in nine square zones of identical size. For novelty test, rats were individually placed into the center of the open-field, and allowed to explore the field for 5 min. Rats were then allowed to return to their home cage. The arena was cleaned with a saline solution between animals. For the saline injection test at P11, rats received a saline injection (1 mL/kg, i.p.) and were immediately placed into the center of the open-field and allowed to explore the field for 5 min. For restraint stress test, animals were restrained through immobilization for 15 min in a Plexiglas tube (5.5 cm×21 cm) and were immediately placed into the center of the open-field and allowed to explore the field for 5 min.

For all test, the behavior of each animal was observed by the experimenter. Overall horizontal motor activity was quantified as the number of lines crossed over the 5 min-period. Furthermore, the number of rearings (rising up on hind legs with the forelegs in the air or against the wall) was scored as follows: 0=absent, 1=few, 2=moderate, 3=high, 4=very high.

B. Results

1. Locomotor Response to Novelty

For all time points, after exposure to novelty, all rats displayed a high degree of horizontal and vertical locomotor activity in the open-field during the 5-min period.

The overall results of the novelty test over the different experimental time points are presented in FIG. 27. In all ENV-injected animals, the increase in the horizontal locomotor activity was not present early after injection (P5) but gradually emerged over time, particularly in rats injected into the hippocampus (ENV-hipp rats) (FIG. 27A). Interestingly, only ENV-hipp rat displayed persistent exacerbated horizontal activity at P12. Furthermore, increased vertical locomotor activity was detected as soon as P5 and P6 in ENV-hipp rats, while no difference with the sham animal was reported in ENV-icv rats at the same time points.

2. Locomotor Activity after Saline Injection

After exposure to saline injection, all rats displayed a high degree of horizontal and vertical locomotor activity in the open-field during the 5-min period.

Only ENV-hipp rats displayed a clear increase in horizontal locomotor activity compared to the sham animal (FIG. 28A), while the vertical locomotor activity of all groups was similar (FIG. 28B).

3. Locomotor Activity after Restraint Stress

After exposure to restraint stress, all rats displayed a high degree of horizontal and vertical locomotor activity in the open-field during the 5-min period. For both horizontal and vertical activity, ENV-hipp rats displayed higher locomotor activity compared to sham animals, while no clear difference could be detected between sham and ENV-icv rats (FIG. 29).

In this second series of experiment, we showed that a single bilateral injection of ENV protein in lateral ventricles or in hippocampus could lead to an exacerbation of the sensibility to mild stress conditions. Moreover, the behavioral alterations were shown to be significantly more severe and persistent in ENV-Hipp rats. In addition, an aberrant locomotor response to the restraint stress challenge was only observed in ENV-Hipp rats. Rats with bilateral hippocampal injection of ENV protein provide a relevant model, more than icy-injected model, in order to study treatments for schizophrenia in a pre-clinical model.

We therefore further evaluated the therapeutic effect of human-chimeric IgG4 Ligand in this optimized model.

IV. Evaluation of Chimeric IgG4 Ligand Therapeutic Effect on Neurobehavioral Psychotic Symptoms Following Single Bilateral Injection of ENV Protein in the Hippocampus of Rats.

A. Materials and Methods

1. Animals

Same as in part III of the present example.

2. Bilateral Injection of ENV Protein in the Hippocampus or in the Lateral Ventricles Same as in part III of the present example, with additional injection of antibody in certain animals as described below.

For each rat, the injection of each solution (PBS, ENV and IgG4) was achieved via a stainless steel injector, placed in and projecting 0.5 mm below the tip of the cannula. The injector was connected by polythene tubing to a Hamilton syringe (VWR, France) to manually dispense solutions over a 3-min period. The injector was withdrawn 3 min after the completion of ejection to prevent the flow of PBS or ENV protein along the injector track. For the IgG4-treated ENV rats, 2 µg of the antibody was infused 10 minutes after the injection of ENV protein in both hemispheres at the same coordinates. The wound was closed using surgical suture on a needle holder. Animals were allowed to recover in an individual cage for a 2 days-period. Then, the animals were randomly housed three per cage and were maintained undisturbed until further experiments.

3. Results

These results first provide a reproduction of the previous experiment with stereotaxic injection in the hippocampus of ENV protein with an exacerbation of the sensibility to mild stress conditions, as in the example illustrated below for P12 in FIG. 31A.

Surprisingly and not seen in the previous experiment that stopped animal follow-up after 12 days (P12), the behavioral alterations of (untreated) ENV+ rats were shown to have a significant evolution from hyper-reactivity to mild stress still observed at P12, to hypo-reactivity (freezing) as observed in this group at P32 (represented by the middle bar in histograms of FIG. 30A). Apart from further results on the therapeutic effect of the IgG4 Ligand at day 32, this observation is quite interesting as it reproduces key features of the natural clinical evolution of the human schizophrenia subtype identified to correlate with the presence of elevated ENV antigenaemia and CRP in blood (as evidenced in example 8): the appearance of a "negative symptomatic phase" (hypo-reactivity to stress for the present animal model) associated with cognitive decline and neuronal loss, after the earlier phase characterized by positive symptoms (hyper reactivity to stress for the present animal model).

Indeed, this is typically a later effect associated with neuronal loss as can be also evidenced by cerebral ventricular enlargement, as in MRI observations performed during the present study of rat brains taken 9 months after primary ENV icy injection. Interestingly again and though this had not been objectively quantified by appropriate behavioral tests as in the present experiment, these rats had progressively evolved towards marked hypo-responsiveness during this long delay; this could then be subjectively but constantly observed.

Here, with quantitative and appropriate tests, this shift from "positive symptoms" to "negative symptoms" is confirmed by the second test with restraint stress at P32 (FIG. 30B) of animals injected with ENV protein in the hippocampus, versus SHAM controls. It thus emphasizes the significance and importance of the therapeutic effect now reported in similar animals treated in with IgG4 Ligand, after parallel MSRV ENV protein injection.

As can be seen in FIG. 31A, "ENV+" animals treated with IgG4 did not develop this cognitive decline with apparition of this behavioral hypo-reactivity ("freezing") at P32, and could not be differentiated from SHAM control at this time-point (as illustrated by overlapping error bars on histograms), whereas this difference was significant with untreatated animals (no overlap of error bars on the histograms). Again, a second behavioral test after restraint stress, has reproduced this difference between "ENV+" rats treated with IgG4 Ligand and the non-treated animals with an even greater difference in the results between the two groups: while the untreated "ENV+" animals had an activity significantly reduced by nearly one-half compared to treated animals, the latter had results undistinguishable from the SHAM controls (FIG. 31B).

Thus, as the sub-type of Schizophrenia with elevated CRP serum levels is identified to be associated with MSRV in example 8 and is characterized by this later phase of "negative symptomatology" associated with cognitive decline and neuronal loss, the evidence of a beneficial therapeutic effect in a pre-clinical model of the treatment with the IgG4 Ligand is unexpectedly evidenced on such dramatic symptomatology; This, after MSRV ENV injection has been initiating a relevant pathogenic process in this model, which is confirming a mere therapeutic effect of the Ligand of the present invention in such forms of Schizophrenia (Dickerson, F., C. Stallings, et al. 2007).

Example 18

In Vivo Analysis of GNb AC1 Chimeric Antibody with IgG1 Isotype with Therapeutic Effect in an Animal Model of Cancer, Grafted with Human Lymphoma Cells I. Experiment 1: Effect of IgG1 Chimeric GNb AC1 Antibody on the Migration of Human B-Lymphoma Cells Injected Subcutaneously in Nude Mice A. Materials and Methods 1. Animals Pathogen free female Nude mice (6 to 8 week-old) (n=4) were purchased from Charles River, France. Animals were maintained on the same cage on a standard light-dark cycle with ad libitum access to food and water and were undisturbed for an 8-days period of acclimation. All procedures comply with the European Communities Council Directive of Nov. 24, 1986 (86/609/EEC) and the National Council Directive of Oct. 19, 1987 (87848, "Ministère de l'Agriculture et de la Forêt", Farnce). All efforts were made to minimize the number of animals used and their suffering.

2. Cell Culture

The Akata cell line is an Epstein-Barr Virus-positive cell line derived from a patient who suffered from a Burkitt's lymphoma. The cell line was maintained in RPMI 1640 medium (Sigma, France) supplemented with 10% fetal bovine serum (Gibco®, Invitrogen, France), 40 U of penicillin per ml and 50 μg of streptomycin per ml at 37° C. in a 5% $CO_2$ humidified atmosphere.

3. Cell Injection and Antibody Administration

At P0 (first day), $15 \times 10^7$ lymphoma cells were subcutaneously injected in Nude mice. After a 6 h-delay, two control mice received an i.p. injection of Phosphate Buffer Saline (PBS) (Lonza, France) and one mouse received an ip. injection of the IgG1 chimeric antibody (100 μg/animal). The last mouse was similarly treated with the same antibody 72 h after the injection of lymphoma cells.

4. Histological Examination

At P19, all mice were sacrificed by pentobarbital overdose and were autopsied to assess the presence of anatomopathological abnormalities. Photographs were captured with a digital camera [model Coolpix S500 (i.e., 7 million pixels), Nikon, France] and transferred from the camera to a PC computer.

B. Results

Unexpectedly, no visible subcutaneous tissue mass (tumor) could be detected in non-treated mice, while both IgG1-treated mice showed a locally delineated mass at the site of injection.

At autopsy, we observed a strong splenomegaly in both control mice, while both IgG1-treated mice did not show macroscopic alteration of the spleen. To better estimate the spleen enlargement, a splenic index was calculated as follows: [(spleen weight/body weight)×100]. Interestingly, non-treated Nude mice displayed a 2-fold increase of the spleen/body weight ratio compared to that of IgG1-treated Nude mice, as shown in FIG. 32. Moreover, a slight hepatic enlargement could be also visible in control mice compared to the IgG1-treated mice. Macroscopic examination of other organs (heart, lungs, kidneys, brain, bowel and stomach) did not reveal any major abnormalities.

C. Discussion

In this first experiment, we showed that subcutaneous injection of lymphoblastoid cells in Nude mice can lead to dissemination of lymphoma cells in lymphoid organs, as evidence by a strong splenomegaly, whereas in-situ injected cells appear to have nearly all migrated. In chimeric IgG1-treated mice, we reported an absence of spleen enlargement associated with the persistence of the locally injected lymphoma cell mass confined in situ.

According to the present data the IgG1 chimeric GNb AC1 antibody must have prevented the migration of lymphoma cells through its Ligand effect. These results are thus a convincing argument that IgG1 chimeric antibody comprising the Ligand of the present invention, can be a useful therapeutic tool in the treatment of ENV-positive human tumors.

II. Experiment 2: In Vivo Evidence of Cell Cytotoxicity Against a Human B-Cell Lymphoma after Injection of the MSRV-ENV Binding Ligand in the Form of IgG1 Chimaeric Antibody in a SCID Mouse Model A. Materials and Methods 1. Animals Pathogen free female SCID (severe combined immunodeficiency; devoid of functional T and B lymphocytes, with reduced NK population) mice (6 to 8 week-old; n=5) were purchased from Charles River, France. Animals were maintained on the same cage on a standard light-dark cycle with ad libitum access to food and water and were undisturbed for an 8-days period of acclimation. All procedures comply with the European Communities Council Directive of Nov. 24, 1986 (86/609/EEC) and the National Council Directive of Oct. 19, 1987 (87848, "Ministère de l'Agriculture et de la Forêt, France"). All efforts were made to minimize the number of animals used and their suffering.

2. Cell Culture

The lymphoma cell line is an Epstein-Barr Virus-positive cell line derived from a patient who suffered from a Burkitt's lymphoma. The Akata cell line was maintained in RPMI 1640 medium (Sigma, France) supplemented with 10% fetal bovine serum (Gibco®, Invitrogen, France), 40 U of penicillin per ml and 50 µg of streptomycin per ml at 37° C. in a 5% CO2 humidified atmosphere.

3. Cell Injection and Antibody Administration

The first day P0, 15×107 Akata lymphoblastoid cells (LC) were intraperitoneally injected in all SCID mice. After a 24 h-delay, three control mice received an i.p. injection of Phosphate Buffer Saline (PBS) (Lonza, France) and two mice received an i.p. injection of 100 µg of the IgG1 chimaeric antibody.

4. Histological Examination and Cell Count

At P7, all mice were sacrificed by pentobarbital overdose. Afterwards, peritoneal wash cells were collected in 5 ml of PBS. Viability determination of LC was based on Trypan blue dye staining of the peritoneal fluid. The LC and other white blood cells were observed and counted with low power microscopy. Human Burkitt's Lymphoma cells could be easily identified by their morphology and confirmation of their specificity was obtained by immunocytochemistry performed with anti-Eptein-Barr Virus monoclonals, specific for expressed proteins of latency, as well as with monoclonals specific for human B-cell markers (not shown).

Mice were also autopsied to assess the presence of anatomopathological abnormalities. Particularly, potential splenic alteration was estimated by the spleen/body weight ratio calculated as follows: [(spleen weight/body weight)× 100].

B. Results

Macroscopic examination of all mice did not reveal the presence of palpable tumor, which was consistent with the very short duration of the study, justified by the necessity to address antibody dependent cytotoxicity in a short delay after lymphoma cells injection and, thereafter, antibody or mock-injection. However, splenomegaly could be easily detected in both control mice, while both IgG1-treated mice did not show macroscopic modification of the spleen. As in the previous experiment with subcutaneous injection of the same cells in Nude mice, non-treated SCID mice displayed a 2-fold increase of the spleen/body weight ratio compared to that of IgG1-treated SCID mice (FIG. 32). Macroscopic examination of other organs (heart, lungs, kidneys, brain, bowel and stomach) did not reveal any major abnormalities.

The analysis of the peritoneal fluid of IgG1-treated mice revealed a decrease in the number of both alive and dead lymphoma cells compared to that of control mice (FIG. 33A). Most interestingly, about 50% of lymphoma cells collected from the peritoneal cavity of Chimeric GNb AC1 IgG1-treated mice were dead cells six days after antibody injection. In parallel, an increase in the number of other mononuclear white blood cells (mainly macrophage cells of monocytic origin and few NK cells, in SCID mice) was observed in IgG1-treated mice compared to control mice (FIG. 33B).

C. Discussion

In this second experiment, we have observed that intraperitoneal injection of Burkitt's lymphoma cells in SCID mice can induce splenomegaly after 7 days, consistently with our previous study in Nude mice showing the same after 19 days. Interestingly, IgG1-treated mice did not show such a spleen enlargement.

Moreover, the conjunction of (i) the decrease in the number of living lymphoma cells collected from the peritoneal cavity, when compared to non-treated animals, of (ii) the important proportion of dead malignant cells, and of (iii) the increase in the number of other mononuclear white blood cells, is highly indicative of antibody-dependent direct and/or cell-mediated cytotoxic effect on tumor cells. This effect is thus reflecting (i) the specificity of the Ligand that is binding to tumor cells expressing the target Epitope in MSRV-ENV proteins exposed on human tumor cells as evidenced in example 8 and (ii) the added IgG1 isotype-mediated humoral immune effects involving tumor cell destruction. The latter effect can be mediated through, e.g., Complement activation by IgG1 active sites and, e.g., macrophage tumoricidal activity induced through FC receptor interaction with GNb AC1 IgG1 bound to tumor MSRV-ENV antigen.

Whatever the mechanisms implicated in the effects of this chimeric IgG1 antibody, our results demonstrate an inhibition of lymphoma cell proliferation in a preclinical animal model with human tumor cells, thus evidencing the therapeutic potential of anti-ENV Ligand antibody in the treatment of such ENV-positive cancers.

REFERENCES

Johnson G, Wu T T. Kabat Database and its applications: future directions. Nucleic Acids Res 2001; 29: 205-6.

Chothia C, Gelfand 1, Kister A. Structural determinants in the sequences of immunoglobulin variable domain. J Mol Biol 1998; 278: 457-79.

Bech P, Rafaelsen O J, Kramp P, Bolwig T G (1978) The mania rating scale: scale construction and inter-observer agreement. Neuropharmacology 17:430-431.

Edgar P P, Schwartz R D (1992) Functionally relevant gamma-aminobutyric acidA receptors: equivalence between receptor affinity (Kd) and potency (EC50)? Mol Pharmacol 41:1124-1129.

Firouzi R, A. R, Michel M, E. J-M, Hauw J J, Malcus-vocanson C, Lazarini F, Gebhurer L, Seigneurin J M, Touraine J, Sanhadji K, Marche P, Perron H (2003) Multiple Sclerosis Associated Retrovirus Particles Cause T-Lymphocyte Dependent Death with Brain Hemorrhage, in Humanized SCID Mice Model. Journal of Neurovirology 9:79-93.

Houenou J, Szoke A, Meary A, Loze J-Y, Mathieu M, Leboyer M, Schurhoff F (2007) Psychometric properties of the French version of the signs and symptoms of psychotic illness (SSPI) scale. Encephale 33:744-750.

Huang W M (1986) The 52-protein subunit of T4 DNA topoisomerase is homologous to the gyrA-protein of gyrase. Nucleic Acids Res 14:7379-7390.

Janke C, Martin D, Giraud-Panis M J, Decoville M, Locker D (2003) *Drosophila* DSP1 and rat HMGB1 have equivalent DNA binding properties and share a similar secondary fold. J Biochem 133:533-539.

Kane J M (1996) Treatment-resistant schizophrenic patients. J Clin Psychiatry 57 Suppl 9:35-40.

Lamande S R, Bateman J F (1993) A type I collagen reporter gene construct for protein engineering studies. Functional equivalence of transfected reporter COL1A1 and endogenous gene products during biosynthesis and in vitro extracellular matrix accumulation. Biochem J 293 (Pt 2):387-394.

McDonald W I, Compston A, Edan G, Goodkin D, Hartung H P, Lublin F D, McFarland H F, Paty D W, Polman C H, Reingold S C, Sandberg-Wollheim M, Sibley W, Thompson A, van den Noort S, Weinshenker B Y, Wolinsky J S (2001) Recommended diagnostic criteria for multiple sclerosis: guidelines from the International Panel on the diagnosis of multiple sclerosis. Ann Neurol 50:121-127.

Minuth T, Kramer B, Lehle K, Jaenicke R, Kohnert U (1998) The spectroscopic analysis, inhibition and binding studies demonstrate the equivalence of Erythrina caffra trypsin inhibitor and the recombinant substitution variant recSerETI. J Biotechnol 62:231-239.

Montgomery S A, Asberg M (1979) A new depression scale designed to be sensitive to change. Br J Psychiatry 134:382-389.

Perron H, Firouzi R, Tuke P, Garson J A, Michel M, Beseme F, Bedin F, Mallet F, Marcel E, Seigneurin J M, Mandrand B (1997a) Cell cultures and associated retroviruses in multiple sclerosis. Collaborative Research Group on MS. Acta Neurol Scand Suppl 169:22-31.

Perron H, Garson J A, Bedin F, Beseme F, Paranhos-Baccala G, Komurian-Pradel F, Mallet F, Tuke P W, Voisset C, Blond J L, Lalande B, Seigneurin J M, Mandrand B (1997b) Molecular identification of a novel retrovirus repeatedly isolated from patients with multiple sclerosis. The Collaborative Research Group on Multiple Sclerosis. Proc Natl Acad Sci USA 94:7583-7588.

Perron H, Jouvin-Marche E, Michel M, Ounanian-Paraz A, Camelo S, Dumon A, Jolivet-Reynaud C, Marcel F, Souillet Y, Borel E, Gebuhrer L, Santoro L, Marcel S, Seigneurin J M, Marche P N, Lafon M (2001) Multiple sclerosis retrovirus particles and recombinant envelope trigger an abnormal immune response in vitro, by inducing polyclonal Vbeta16 T-lymphocyte activation. Virology 287: 321-332.

Rolland A, Jouvin-Marche E, Viret C, Faure M, Perron H, Marche P N (2006) The envelope protein of a human endogenous retrovirus-W family activates innate immunity through CD14/TLR4 and promotes Th1-like responses. J Immunol 176:7636-7644.**

Sardana W, Emini E A, Gotlib L, Graham D J, Lineberger D W, Long W J, Schlabach A J, Wolfgang J A, Condra J H (1992) Functional analysis of HIV-1 reverse transcriptase amino acids involved in resistance to multiple nonnucleoside inhibitors. J Biol Chem 267:17526-17530.

Stefas E, Rucheton M, Graafland H, Moynier M, Sompeyrac C, Bahraoui E M, Veas F (1997) Human plasmatic apolipoprotein H binds human immunodeficiency virus type 1 and type 2 proteins. AIDS Res Hum Retroviruses 13:97-104.

Stefas I, Rucheton M, D'Angeac A D, Morel-Baccard C, Seigneurin J M, Zarski J P, Martin M, Cerutti M, Bossy J P, Misse D, Graafland H, Veas F (2001) Hepatitis B virus Dane particles bind to human plasma apolipoprotein H. Hepatology 33:207-217.

Ullmann G M, Hauswald M, Jensen A, Knapp E W (2000) Structural alignment of ferredoxin and flavodoxin based on electrostatic potentials: implications for their interactions with photosystem I and ferredoxin-NADP reductase. Proteins 38:301-309.

Ullmann G M, Hauswald M, Jensen A, Kostic N M, Knapp E W (1997) Comparison of the physiologically equivalent proteins cytochrome c6 and plastocyanin on the basis of their electrostatic potentials. Tryptophan 63 in cytochrome c6 may be isofunctional with tyrosine 83 in plastocyanin. Biochemistry 36:16187-16196.

Verdoliva A, Ruvo M, Cassani G, Fassina G (1995) Topological mimicry of cross-reacting enantiomeric peptide antigens. J Biol Chem 270:30422-30427.

Wehrmann A, Van Vliet A, Opsomer C, Botterman J, Schulz A (1996) The similarities of bar and pat gene products make them equally applicable for plant engineers. Nat Biotechnol 14:1274-1278.

Xu G L, Kapfer W, Walter J, Trautner T A (1992) BsuBI—an isospecific restriction and modification system of PstI: characterization of the BsuBI genes and enzymes. Nucleic Acids Res 20:6517-6523.

Yu H, Schurr M J, Deretic V (1995) Functional equivalence of Escherichia coli sigma E and Pseudomonas aeruginosa AlgU: E. coli rpoE restores mucoidy and reduces sensitivity to reactive oxygen intermediates in algU mutants of P. aeruginosa. J Bacteriol 177:3259-3268.

Zabin H B, Horvath M P, Terwilliger T C (1991) Approaches to predicting effects of single amino acid substitutions on the function of a protein. Biochemistry 30:6230-6240.

Antony J M, Ellestad K K, Hammond R, Imaizumi K, Mallet F, Warren K G, Power C (2007). The human endogenous retrovirus envelope glycoprotein, syncytin-1, regulates neuroinflammation and its receptor expression in multiple sclerosis: a role for endoplasmic reticulum chaperones in astrocytes. J Immunol 179: 1210-24.

Antony J M, van Marle G, Opii W, Butterfield D A, Mallet F, Yong V W, Wallace J L, Deacon R M, Warren K, Power C (2004). Human endogenous retrovirus glycoprotein-mediated induction of redox reactants causes oligodendrocyte death and demyelination. Nat Neurosci 7: 1088-95.

Blond J L, Beseme F, Duret L, Bouton O, Bedin F, Perron H, Mandrand B, Mallet F (1999). Molecular characterization and placental expression of HERV-W, a new human endogenous retrovirus family. J Virol 73: 1175-85.

Cheynet V, Oriol G, Mallet F (2006). Identification of the hASCT2-binding domain of the Env ERVWE1/syncytin-1 fusogenic glycoprotein. Retrovirology 3: 41.

Christensen T, Dissing Sorensen P, Riemann H, Hansen H J, Moller-Larsen A (1998). Expression of sequence variants of endogenous retrovirus RGH in particle form in multiple sclerosis. Lancet 352: 1033.

Deb-Rinker P, Klempan T A, O'Reilly R L, Torrey E F, Singh S M (1999). Molecular characterization of a MSRV-like sequence identified by RDA from monozygotic twin pairs discordant for schizophrenia. Genomics 61: 133-44.

Dolei A, Serra C, Mameli G, Pugliatti M, Sechi G, Cirotto M C, Rosati G, Sotgiu S (2002). Multiple sclerosis-associated retrovirus (MSRV) in Sardinian MS patients. Neurology 58: 471-3.

Firouzi R, Rolland A, Michel M, Jouvin-Marche E, Hauw J J, Malcus-Vocanson C, Lazarini F, Gebuhrer L, Seigneurin J M, Touraine J L, Sanhadji K, Marche P N, Perron H (2003). Multiple sclerosis-associated retrovirus particles cause T lymphocyte-dependent death with brain hemorrhage in humanized SCID mice model. J Neurovirol 9: 79-93.

Flockerzi A, Ruggieri A, Frank O, Sauter M, Maldener E, Kopper B, Wullich B, Seifarth W, Muller-Lantzsch N, Leib-Mosch C, Meese E, Mayer J (2008). Expression patterns of transcribed human endogenous retrovirus HERV-K (HML-2) loci in human tissues and the need for a HERV Transcriptome Project. BMC Genomics 9: 354.

Garson J A, Tuke P W, Giraud P, Paranhos-Baccala G, Perron H (1998). Detection of virion-associated MSRV-RNA in serum of patients with multiple sclerosis. Lancet 351: 33.

Karlsson H, Bachmann S, Schroder J, McArthur J, Torrey E F, Yolken R H (2001). Retroviral RNA identified in the cerebrospinal fluids and brains of individuals with schizophrenia. Proc Natl Acad Sci USA 98: 4634-9.

Karlsson H, Schroder J, Bachmann S, Bottmer C, Yolken R H (2004). HERV-W-related RNA detected in plasma from individuals with recent-onset schizophrenia or schizoaffective disorder. Mol Psychiatry 9: 12-3.

Kim H S (2001). Sequence and phylogeny of HERV-W pol fragments. AIDS Res Hum Retroviruses 17: 1665-71.

Knerr I, Huppertz B, Weigel C, Dotsch J, Wich C, Schild R L, Beckmann M W, Rascher W (2004). Endogenous retroviral syncytin: compilation of experimental research on syncytin and its possible role in normal and disturbed human placentogenesis. Mol Hum Reprod 10: 581-8.

Komurian-Pradel F, Paranhos-Baccala G, Bedin F, Ounanian-Paraz A, Sodoyer M, Ott C, Rajoharison A, Garcia E, Mallet F, Mandrand B, Perron H (1999). Molecular cloning and characterization of MSRV-related sequences associated with retrovirus-like particles. Virology 260: 1-9.

Langbein M, Strick R, Strissel P L, Vogt N, Parsch H, Beckmann M W, Schild R L (2008). Impaired cytotrophoblast cell-cell fusion is associated with reduced Syncytin and increased apoptosis in patients with placental dysfunction. Mol Reprod Dev 75: 175-83.

Laufer G, Mayer J, Mueller B F, Mueller-Lantzsch N, Ruprecht K (2009). Analysis of transcribed human endogenous retrovirus W env loci clarifies the origin of multiple sclerosis-associated retrovirus env sequences. Retrovirology 6: 37.

Lavillette D, Marin M, Ruggieri A, Mallet F, Cosset F L, Kabat D (2002). The envelope glycoprotein of human endogenous retrovirus type W uses a divergent family of amino acid transporters/cell surface receptors. J Virol 76: 6442-52.

Linial M L, Miller A D (1990). Retroviral RNA packaging: sequence requirements and implications. In: Retroviruses—strategies of replication. Swanstrom R, Vogt P K, (eds). Springer-Verlag: Berlin, pp 125-152.

Malassine A, Handschuh K, Tsatsaris V, Gerbaud P, Cheynet V, Oriol G, Mallet F, Evain-Brion D (2005). Expression of HERV-W Env glycoprotein (syncytin) in the extravillous trophoblast of first trimester human placenta. Placenta 26: 556-62.

Mallet F, Bouton O, Prudhomme S, Cheynet V, Oriol G, Bonnaud B, Lucotte G, Duret L, Mandrand B (2004). The endogenous retroviral locus ERVWE1 is a bona fide gene involved in hominoid placental physiology. Proc Natl Acad Sci USA 101: 1731-6.

Mameli G, Astone V, Arru G, Marconi S, Lovato L, Serra C, Sotgiu S, Bonetti B, Dolei A (2007). Brains and peripheral blood mononuclear cells of multiple sclerosis (MS) patients hyperexpress MS-associated retrovirus/HERV-W endogenous retrovirus, but not Human herpesvirus 6. J Gen Virotl 88: 264-74.

Noorali S, Rotar I C, Lewis C, Pestaner J P, Pace D G, Sison A, Bagasra O (2009). Role of HERV-W Syncytin-1 in Placentation and Maintenance of Human Pregnancy. Appl Immunohistochem Mol Morphol.

Perron H, Bernard C, Bertrand J B, Lang A B, Popa I, Sanhadji K, Portoukalian J (2009). Endogenous retroviral genes, Herpesviruses and gender in Multiple Sclerosis. J Neurol Sci.

Perron H, Firouzi R, Tuke P, Garson J A, Michel M, Beseme F, Bedin F, Mallet F, Marcel E, Seigneurin J M, Mandrand B (1997a). Cell cultures and associated retroviruses in multiple sclerosis. Collaborative Research Group on MS. Acta Neurol Scand Suppl 169: 22-31.

Perron H, Garson J A, Bedin F, Beseme F, Paranhos-Baccala G, Komurian-Pradel F, Mallet F, Tuke P W, Voisset C, Blond J L, Lalande B, Seigneurin J M, Mandrand B (1997b). Molecular identification of a novel retrovirus repeatedly isolated from patients with multiple sclerosis. The Collaborative Research Group on Multiple Sclerosis. Proc Natl Acad Sci USA 94: 7583-8.

Perron H, Jouvin-Marche E, Michel M, Ounanian-Paraz A, Camelo S, Dumon A, Jolivet-Reynaud C, Marcel F, Souillet Y, Borel E, Gebuhrer L, Santoro L, Marcel S, Seigneurin J M, Marche P N, Lafon M (2001). Multiple sclerosis retrovirus particles and recombinant envelope trigger an abnormal immune response in vitro, by inducing polyclonal Vbeta16 T-lymphocyte activation. Virology 287: 321-32.

Perron H, Lalande B, Gratacap B, Laurent A, Genoulaz O, Geny C, Mallaret M, Schuller E, Stoebner P, Seigneurin J M (1991). Isolation of retrovirus from patients with multiple sclerosis. Lancet 337: 862-3.

Perron H, Lazarini F, Ruprecht K, Pechoux-Longin C, Seilhean D, Sazdovitch V, Creange A, Battail-Poirot N, Sibai G, Santoro L, Jolivet M, Darlix J L, Rieckmann P, Arzberger T, Hauw J J, Lassmann H (2005). Human endogenous retrovirus (HERV)-W ENV and GAG proteins: physiological expression in human brain and pathophysiological modulation in multiple sclerosis lesions. J Neurovirol 11: 23-33.

Perron H, Mekaoui L, Bernard C, Veas F, Stefas I, Leboyer M (2008). Endogenous retrovirus type W GAG and envelope protein antigenemia in serum of schizophrenic patients. Biol Psychiatry 64: 1019-23.

Perron H, Perin J P, Rieger F, Alliel P M (2000). Particle-associated retroviral RNA and tandem RGH/HERV-W copies on human chromosome 7q: possible components of a 'chain-reaction' triggered by infectious agents in multiple sclerosis? J Neurovirol 6 Suppl 2: S67-75.

Rasmussen H B, Perron H, Clausen J (1993). Do endogenous retroviruses have etiological implications in inflammatory and degenerative nervous system diseases? Acta Neurol Scand 88: 190-8.

Rolland A, Jouvin-Marche E, Saresella M, Ferrante P, Cavaretta R, Creange A, Marche P, Perron H (2005). Correlation between disease severity and in vitro cytokine production mediated by MSRV (multiple sclerosis associated retroviral element) envelope protein in patients with multiple sclerosis. J Neuroimmunol 160: 195-203.

Rolland A, Jouvin-Marche E, Viret C, Faure M, Perron H, Marche P N (2006). The envelope protein of a human endogenous retrovirus-W family activates innate immunity through CD14/TLR4 and promotes Th1-like responses. J Immunol 176: 7636-44.

Saresella M, Rolland A, Marventano 1, Cavarretta R, Caputo D, Marche P, Perron H, Clerici M (2009). Multiple sclerosis-associated retroviral agent (MSRV)-stimulated cytokine production in patients with relapsing-remitting multiple sclerosis. Mult Scler 15: 443-7.

Serra C, Sotgiu S, Mameli G, Pugliatti M, Rosati G, Dolei A (2001). Multiple sclerosis and multiple sclerosis-associated retrovirus in Sardinia. Neurol Sci 22: 171-3.

Sotgiu S, Arru G, Mameli G, Serra C, Pugliatti M, Rosati G, Dolei A (2006). Multiple sclerosis-associated retrovirus in early multiple sclerosis: a six-year follow-up of a Sardinian cohort. Mult Scler 12: 698-703.

Sotgiu S, Serra C, Mameli G, Pugliatti M, Rosati G, Arru G, Dolei A (2002). Multiple sclerosis-associated retrovirus and MS prognosis: an observational study. Neurology 59: 1071-3.

Voisset C, Blancher A, Perron H, Mandrand B, Mallet F, Paranhos-Baccala G (1999). Phylogeny of a novel family of human endogenous retrovirus sequences, HERV-W, in humans and other primates. AIDS Res Hum Retroviruses 15: 1529-33.

Voisset C, Bouton O, Bedin F, Duret L, Mandrand B, Mallet F, Paranhos-Baccala G (2000). Chromosomal distribution and coding capacity of the human endogenous retrovirus HERV-W family. AIDS Res Hum Retroviruses 16: 731-40.

Weis S, Llenos I C, Dulay J R, Verma N, Sabunciyan S, Yolken R H (2007). Changes in region- and cell type-specific expression patterns of neutral amino acid transporter 1 (ASCT-1) in the anterior cingulate cortex and hippocampus in schizophrenia, bipolar disorder and major depression. J Neural Transm 114: 261-71.

Yolken R H, Karlsson H, Yee F, Johnston-Wilson N L, Torrey E F (2000). Endogenous retroviruses and schizophrenia. Brain Res Brain Res Rev 31: 193-9.

Bornstein, R. A., S. B. Schwarzkopf, et al. (1992). "Third-ventricle enlargement and neuropsychological deficit in schizophrenia." *Biol Psychiatry* 31(9): 954-61.

Dickerson, F., C. Stallings, et al. (2007). "C-reactive protein is associated with the severity of cognitive impairment but not of psychiatric symptoms in individuals with schizophrenia." Schizophr Res 93(1-3): 261-5.

Aalberse and Schuurman 2002, IgG4 breaking the rules, Immunology. 2002, 105:9-19

---

The invention claimed is:

1. A method of prophylactically or therapeutically treating MSRV-associated diabetes, comprising administering an effective amount of a ligand to a patient in need of prophylactic or therapeutic treatment of MSRV-associated diabetes, wherein the ligand comprises each of the complementary-determining regions (CDRs) having the amino acid sequences set forth in SEQ ID No. 1, SEQ ID No. 2, SEQ ID No. 3, SEQ ID No. 4, SEQ ID No. 5 and SEQ ID No. 6.

2. The method of claim 1, wherein the ligand binds to an anti-ligand comprising the amino acid sequence set forth in SEQ ID No. 20 or SEQ ID No. 32.

3. The method of claim 1, wherein the ligand comprises:
a light chain variable region (VL) comprising the amino acid sequences set forth in SEQ ID No. 1, SEQ ID No. 2 and SEQ ID No. 3; and
a heavy chain variable region (VH) comprising the amino acid sequences set forth in SEQ ID No. 4, SEQ ID No. 5 and SEQ ID No. 6.

4. The method of claim 1, wherein an scFv or Fab fragment comprising the ligand is administered.

5. The method of claim 1, wherein an antibody comprising the ligand is administered.

6. The method of claim 5, wherein the antibody is a chimeric, engineered or humanized antibody.

7. The method of claim 5, wherein the antibody is an IgG.

8. The method of claim 7, wherein the antibody is an IgG1 or an IgG4.

9. The method of claim 1, wherein the method comprises administering an IgG4 or IgG1 antibody comprising the ligand to the patient as a chronic treatment with regularly repeated injections to treat MSRV-associated diabetes.

10. The method of claim 1, wherein the ligand comprises:
a light chain variable region (VL) that has the amino acid sequence set forth in SEQ ID No. 7; and
a heavy chain variable region (VH) that has the amino acid sequence set forth in SEQ ID No. 8.

11. The method of claim 1, wherein the method comprises administering an IgG4 antibody comprising the ligand to the patient as a chronic treatment with regularly repeated injections to treat MSRV-associated diabetes.

12. The method of claim 1, wherein an antibody comprising the ligand is administered and the antibody comprises the amino acid sequences of SEQ ID No. 61 and SEQ ID No. 62.

13. The method of claim 1, wherein an antibody comprising the ligand is administered and the antibody comprises the amino acid sequences of SEQ ID No. 63 and SEQ ID No. 64.

14. The method of claim 1, wherein MSRV-associated type 1 diabetes is being treated.

* * * * *

SEQUENCE LISTING

```
<160> NUMBER OF SEQ ID NOS: 66

<210> SEQ ID NO 1
<211> LENGTH: 10
<212> TYPE: PRT
<213> ORGANISM: Mus musculus

<400> SEQUENCE: 1

Ser Ala Ser Ser Val Ser Tyr Met Tyr
1               5                   10

<210> SEQ ID NO 2
<211> LENGTH: 7
<212> TYPE: PRT
<213> ORGANISM: Mus musculus

<400> SEQUENCE: 2

Arg Thr Ser Asn Leu Ala Ser
1               5

<210> SEQ ID NO 3
<211> LENGTH: 9
<212> TYPE: PRT
<213> ORGANISM: Mus musculus

<400> SEQUENCE: 3

Gln Gln Tyr Gln Ser Leu Pro Leu Thr
1               5

<210> SEQ ID NO 4
<211> LENGTH: 5
<212> TYPE: PRT
<213> ORGANISM: Mus musculus

<400> SEQUENCE: 4

Asp Tyr Glu Met His
1               5

<210> SEQ ID NO 5
<211> LENGTH: 17
<212> TYPE: PRT
<213> ORGANISM: Mus musculus

<400> SEQUENCE: 5

Ala Val Ala Pro Glu Thr Gly Gly Thr Ala Tyr Asn Gln Lys Phe Lys
1               5                   10                  15

Gly
```

<210> SEQ ID NO 6
<211> LENGTH: 7
<212> TYPE: PRT
<213> ORGANISM: Mus musculus

<400> SEQUENCE: 6

Thr Val Val Pro Phe Ala Tyr
1               5

<210> SEQ ID NO 7
<211> LENGTH: 106
<212> TYPE: PRT
<213> ORGANISM: Mus musculus

<400> SEQUENCE: 7

Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Val Ser Tyr Met
            20                  25                  30

Tyr Trp Tyr Gln Gln Lys Pro Gly Ser Ser Pro Lys Ala Trp Ile Tyr
        35                  40                  45

Arg Thr Ser Asn Leu Ala Ser Gly Val Pro Gly Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr Gln Ser Leu Pro Leu Thr
                85                  90                  95

Phe Gly Ser Gly Thr Lys Leu Glu Ile Lys
            100                 105

<210> SEQ ID NO 8
<211> LENGTH: 116
<212> TYPE: PRT
<213> ORGANISM: Mus musculus

<400> SEQUENCE: 8

Gln Val Gln Leu Gln Gln Ser Gly Ala Glu Leu Val Arg Pro Gly Ala
1               5                   10                  15

Pro Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Val Ala Pro Glu Thr Gly Gly Thr Ala Tyr Asn Gln Lys Phe
    50                  55                  60

Lys Gly Lys Ala Thr Leu Thr Ala Ala Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Ser Thr Val Val Pro Phe Ala Tyr Trp Gly Gln Gly Thr Leu Val
            100                 105                 110

Thr Val Ser Ala
        115

<210> SEQ ID NO 9
<211> LENGTH: 318
<212> TYPE: DNA
<213> ORGANISM: Mus musculus
<220> FEATURE:

```
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
```

-continued

```
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (189)..(189)
```

```
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (219)..(219)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t
<220> FEATURE:
<221> NAME/KEY: misc_feature
```

<220> FEATURE:
<221> NAME/KEY: misc_feature
<222> LOCATION: (288)..(288)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t

<400> SEQUENCE: 9

```
carathgtny tnacncarws nccngcnath atgwsngcnw snccnggnga raargtnacn      60
athwsntgyw sngcnwsnws nwsngtnwsn tayatgtayt ggtaycarca raarccnggn     120
wsnwsnccna argcntggat htaymgnacn wsnaayytng cnwsnggngt nccnggnmgn     180
ttywsnggnw snggnwsngg nacnwsntay wsnytnacna thwsnwsnat ggargcngar     240
gaygcngcna cntaytaytg ycarcartay carwsnytnc cnytnacntt yggnwsnggn     300
acnaarytng arathaar                                                   318
```

<210> SEQ ID NO 10
<211> LENGTH: 348
<212> TYPE: DNA
<213> ORGANISM: Mus musculus
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:

```
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
```

-continued

```
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (219)..(219)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (237)..(237)
```

-continued

```
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
```

```
<222> LOCATION: (333)..(333)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t

<400> SEQUENCE: 10
cargtncary tncarcarws nggngcngar ytngtnmgnc cnggngcncc ngtnacnytn    60
wsntgyaarg cnwsnggnta yacnttyacn gaytaygara tgcaytgggt naarcaracn   120
ccngtncayg gnytngartg gathggngcn gtngcnccng aracnggngg nacngcntay   180
aaycaraart tyaarggnaa rgcnacnytn acngcgcna arwsnwsnws nacngcntay    240
atggarytnm gnwsnytnac nwsngargay wsngcngtnt aytaytgyac nwsnacngtn   300
gtnccnttyg cntaytgggg ncarggnacn ytngtnacng tnwsngcn               348

<210> SEQ ID NO 11
<211> LENGTH: 318
<212> TYPE: DNA
<213> ORGANISM: Mus musculus

<400> SEQUENCE: 11
caaattgttc tcacccagtc tccagcaatc atgtctgcat ctccagggga gaaggtcacc    60
atatcctgca gtgccagctc aagtgtaagt tacatgtact ggtaccagca gaagccagga   120
tcctccccca agcctggatt tatcgcaca tccaacctgg cttctggagt ccctggtcgc    180
ttcagtggca gtgggtctgg gacctcttat tctctcacaa tcagcagcat ggaggctgaa   240
gatgctgcca cttattactg ccagcagtat caaagtctcc cactcacgtt cggctcgggg   300
acaaagttgg aaataaaa                                                 318

<210> SEQ ID NO 12
<211> LENGTH: 348
<212> TYPE: DNA
<213> ORGANISM: Mus musculus

<400> SEQUENCE: 12
caggttcaac tgcagcagtc tggggctgag ctggtgaggc ctggggcttc agtgacactg    60
tcctgcaagg cttcgggcta cacatttact gactatgaaa tgcactgggt gaagcagaca   120
cctgtgcatg gcctggaatg gattggagct gttgctcctg aaactggtgg tactgcctac   180
aatcagaagt tcaagggcaa ggccacactg actgcagcca atcctccag cacagcctac    240 atggagctcc gcagcctgac atctgaggac tctgccgtct attactgtac ttctacggtg   300
gtcccttttg cttactgggg ccaagggact ctggtcactg tctctgca              348

<210> SEQ ID NO 13
```

```
<211> LENGTH: 30
<212> TYPE: DNA
<213> ORGANISM: Mus musculus
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 13
wsngcnwsnw snwsngtnws ntayatgtay                                30

<210> SEQ ID NO 14
<211> LENGTH: 21
<212> TYPE: DNA
<213> ORGANISM: Mus musculus
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 14
mgnacnwsna ayytngcnws n                                         21

<210> SEQ ID NO 15
<211> LENGTH: 27
<212> TYPE: DNA
<213> ORGANISM: Mus musculus
<220> FEATURE:
<221> NAME/KEY: misc_feature
<222> LOCATION: (15)..(15)
<223> OTHER INFORMATION: n is a, c, g, or t
```

-continued

```
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 15
carcartayc arwsnytncc nytnacn                                27

<210> SEQ ID NO 16
<211> LENGTH: 15
<212> TYPE: DNA
<213> ORGANISM: Mus musculus

<400> SEQUENCE: 16
gaytaygara tgcay                                             15

<210> SEQ ID NO 17
<211> LENGTH: 51
<212> TYPE: DNA
<213> ORGANISM: Mus musculus
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 17
```

```
gcngtngcnc cngaracngg nggnacngcn tayaaycara arttyaargg n        51
```

```
<210> SEQ ID NO 18
<211> LENGTH: 21
<212> TYPE: DNA
<213> ORGANISM: Mus musculus
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 18
acngtngtnc cnttygcnta y                                        21

<210> SEQ ID NO 19
<211> LENGTH: 548
<212> TYPE: PRT
<213> ORGANISM: Homo sapiens

<400> SEQUENCE: 19

Met Ala Leu Pro Tyr His Thr Phe Leu Phe Thr Val Leu Leu Pro Pro
 1               5                  10                  15

Phe Ala Leu Thr Ala Pro Pro Cys Cys Cys Thr Thr Ser Ser Ser
             20                  25                  30

Pro Tyr Gln Glu Phe Leu Trp Arg Thr Arg Leu Pro Gly Asn Ile Asp
         35                  40                  45

Ala Pro Ser Tyr Arg Ser Leu Ser Lys Gly Asn Ser Thr Phe Thr Ala
     50                  55                  60

His Thr His Met Pro Arg Asn Cys Tyr Asn Ser Ala Thr Leu Cys Met
 65                  70                  75                  80

His Ala Asn Thr His Tyr Trp Thr Gly Lys Met Ile Asn Pro Ser Cys
                 85                  90                  95

Pro Gly Gly Leu Gly Ala Thr Val Cys Trp Thr Tyr Phe Thr His Thr
            100                 105                 110

Ser Met Ser Asp Gly Gly Gly Ile Gln Gly Gln Ala Arg Glu Lys Gln
        115                 120                 125

Val Lys Glu Ala Ile Ser Gln Leu Thr Arg Gly His Ser Thr Pro Ser
    130                 135                 140

Pro Tyr Lys Gly Leu Val Leu Ser Lys Leu His Glu Thr Leu Arg Thr
145                 150                 155                 160

His Thr Arg Leu Val Ser Leu Phe Asn Thr Thr Leu Thr Arg Leu His
                165                 170                 175

Glu Val Ser Ala Gln Asn Pro Thr Asn Cys Trp Met Cys Leu Pro Leu
            180                 185                 190

His Phe Arg Pro Tyr Ile Ser Ile Pro Val Pro Glu Gln Trp Asn Asn
        195                 200                 205
```

```
Phe Ser Thr Glu Ile Asn Thr Thr Ser Val Leu Val Gly Pro Leu Val
    210                 215                 220

Ser Asn Leu Glu Ile Thr His Thr Ser Asn Leu Thr Cys Val Lys Phe
225                 230                 235                 240

Ser Asn Thr Ile Asp Thr Thr Ser Ser Gln Cys Ile Arg Trp Val Thr
                245                 250                 255

Pro Pro Thr Arg Ile Val Cys Leu Pro Ser Gly Ile Phe Phe Val Cys
                260                 265                 270

Gly Thr Ser Ala Tyr His Cys Leu Asn Gly Ser Ser Glu Ser Met Cys
                275                 280                 285

Phe Leu Ser Phe Leu Val Pro Pro Met Thr Ile Tyr Thr Glu Gln Asp
    290                 295                 300

Leu Tyr Asn His Val Val Pro Lys Pro His Asn Lys Arg Val Pro Ile
305                 310                 315                 320

Leu Pro Phe Val Ile Arg Ala Gly Val Leu Gly Arg Leu Gly Thr Gly
                325                 330                 335

Ile Gly Ser Ile Thr Thr Ser Thr Gln Phe Tyr Tyr Lys Leu Ser Gln
                340                 345                 350

Glu Ile Asn Gly Asp Met Glu Gln Val Thr Asp Ser Leu Val Thr Leu
            355                 360                 365

Gln Asp Gln Leu Asn Ser Leu Ala Ala Val Val Leu Gln Asn Arg Arg
    370                 375                 380

Ala Leu Asp Leu Leu Thr Ala Lys Arg Gly Gly Thr Cys Leu Phe Leu
385                 390                 395                 400

Gly Glu Glu Arg Cys Tyr Tyr Val Asn Gln Ser Arg Ile Val Thr Glu
                405                 410                 415

Lys Val Lys Glu Ile Arg Asp Arg Ile Gln Cys Arg Ala Glu Glu Leu
                420                 425                 430

Gln Asn Thr Glu Arg Trp Gly Leu Leu Ser Gln Trp Met Pro Trp Thr
    435                 440                 445

Leu Pro Phe Leu Gly Pro Leu Ala Ala Ile Ile Phe Leu Leu Leu Phe
    450                 455                 460

Gly Pro Cys Ile Phe Asn Phe Leu Val Lys Phe Val Ser Ser Arg Ile
465                 470                 475                 480

Glu Ala Val Lys Leu Gln Ile Val Leu Gln Met Glu Pro Gln Met Gln
                485                 490                 495

Ser Met Thr Lys Ile Tyr Arg Gly Pro Leu Asp Arg Pro Ala Arg Leu
                500                 505                 510

Cys Ser Asp Val Asn Asp Ile Glu Val Thr Pro Pro Glu Glu Ile Ser
                515                 520                 525

Thr Ala Gln Pro Leu Leu His Ser Asn Ser Val Gly Ser Ser His His
    530                 535                 540

His His His His
545

<210> SEQ ID NO 20
<211> LENGTH: 25
<212> TYPE: PRT
<213> ORGANISM: Homo sapiens

<400> SEQUENCE: 20

Pro Pro Met Thr Ile Tyr Thr Glu Gln Asp Leu Tyr Asn His Val Val
1               5                   10                  15

Pro Lys Pro His Asn Lys Arg Val Pro
            20                  25
```

<210> SEQ ID NO 21
<211> LENGTH: 33
<212> TYPE: DNA
<213> ORGANISM: Artificial Sequence
<220> FEATURE:
<223> OTHER INFORMATION: Synthetic Construct - Primer for RACE PCR
      amplification

<400> SEQUENCE: 21
cggggcggga gtcgactttt ttttttttttt ttt                                33

<210> SEQ ID NO 22
<211> LENGTH: 21
<212> TYPE: DNA
<213> ORGANISM: Artificial Sequence
<220> FEATURE:
<223> OTHER INFORMATION: Synthetic Construct - Primer for RACE PCR
      amplification

<400> SEQUENCE: 22
gcctcagtcg tgtgcttctt g                                              21

<210> SEQ ID NO 23
<211> LENGTH: 18
<212> TYPE: DNA
<213> ORGANISM: Artificial Sequence
<220> FEATURE:
<223> OTHER INFORMATION: Synthetic Construct - Primer for RACE PCR
      amplification

<400> SEQUENCE: 23
ccatcdgtyt atccmytg                                                  18

<210> SEQ ID NO 24
<211> LENGTH: 29
<212> TYPE: PRT
<213> ORGANISM: Homo sapiens

<400> SEQUENCE: 24

Met Ala Leu Pro Tyr His Thr Phe Leu Phe Thr Val Leu Leu Pro Pro
1               5                   10                  15

Phe Ala Leu Thr Ala Pro Pro Cys Cys Cys Thr Thr
            20                  25

<210> SEQ ID NO 25
<211> LENGTH: 21
<212> TYPE: DNA
<213> ORGANISM: Artificial Sequence
<220> FEATURE:
<223> OTHER INFORMATION: Synthetic Construct - CL_Ala130_retour - Primer
      for amplification

<400> SEQUENCE: 25
caagaagcac acgactgagg c                                              21

<210> SEQ ID NO 26
<211> LENGTH: 34
<212> TYPE: DNA
<213> ORGANISM: Artificial Sequence
<220> FEATURE:
<223> OTHER INFORMATION: Synthetic Construct - CH1_Pro119_retour Primer
      for VH amplification with R=A/G; K=G/T; H=A/T/C

<400> SEQUENCE: 26
cggggcggga gtcgaccark ggatarachg atgg                                34

<210> SEQ ID NO 27
<211> LENGTH: 373
<212> TYPE: DNA
<213> ORGANISM: Homo sapiens

<400> SEQUENCE: 27

```
ggtaccctgg atatccggag cctacggcca gatcgtgctg acccagtccc ctgccatcat      60
gtccgccagc cctggcgaga aggtgaccat ctcctgctcc gcctcctcct ccgtgtccta     120
catgtactgg tatcagcaga agcctggctc ctcccctaag gcctggatct accggacctc     180
caacctggcc tccggcgtgc ctggccggtt ctccggctcc ggcagcggca cctcctactc     240
cctgaccatc agctccatgg aggccgagga cgccgccacc tactactgcc agcagtacca     300
gtccctgcct ctgaccttcg gctctggcac caagctggag atcaagcgta cggtggcggc     360
gccatccgag ctc                                                       373
```

<210> SEQ ID NO 28
<211> LENGTH: 6165
<212> TYPE: DNA
<213> ORGANISM: Artificial Sequence
<220> FEATURE:
<223> OTHER INFORMATION: Synthetic Construct - IgG1L+VL optimised
      sequence

<400> SEQUENCE: 28

```
tcaatattgg ccattagcca tattattcat tggttatata gcataaatca atattggcta      60
ttggccattg catacgttgt atctatatca taatatgtac attatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg acccccgccc attgacgtca ataatgacgt atgttcccat     300
agtaacgcca atagggactt tccattgacg tcaatgggtg gagtatttac ggtaaactgc     360
ccacttggca gtacatcaag tgtatcatat gccaagtccg ccccctattg acgtcaatga     420
cggtaaatgg cccgcctggc attatgccca gtacatgacc ttcgggact ttcctacttg     480
gcagtacatc tacgtattag tcatcgctat taccatggtg atgcggtttt ggcagtacac     540
caatgggcgt ggatagcggt ttgactcacg gggatttcca gtctccaccc cattgacgt     600
caatgggagt ttgttttggc accaaaatca acgggacttt ccaaaatgtc gtaacaactg     660
cgatcgcccg ccccgttgac gcaaatgggc ggtaggcgtg tacggtggga ggtctatata     720
agcagagctc gtttagtgaa ccgtcagatc actagaagct ttattgcggt agtttatcac     780
agttaaattg ctaacgcagt cagtgcttct gacacaacag tctcgaactt aagctgcagt     840
gactctctta aggtagcctt gcagaagttg gtcgtgaggc actgggcagg taagtatcaa     900
ggttacaaga caggtttaag gagaccaata gaaactgggc ttgtcgagac agagaagact     960
cttgcgtttc tgataggcac ctattggtct tactgacatc cactttgcct ttctctccac    1020
aggtgtccac tcccagttca attacagctc ttaaggctag agtacttaat acgactcact    1080
ataggctagc ctcgagaatt caccatggcc ctgcagaccc aggtgttcat cagcctgctg    1140
ctgtggatat ccggagccta cggccagatc gtgctgaccc agtcccctgc catcatgtcc    1200
gccagccctg gcgagaaggt gaccatctcc tgctccgcct cctcctccgt gtcctacatg    1260
tactggtatc agcagaagcc tggctcctcc cctaaggcct ggatctaccg gacctccaac    1320
ctggcctccg gcgtgcctgg ccggttctcc ggctccggca gcggcacctc ctactccctg    1380
```

```
accatcagct ccatggaggc cgaggacgcc gccacctact actgccagca gtaccagtcc    1440
ctgcctctga ccttcggctc tggcaccaag ctggagatca agcgtacggt ggcggcgcca    1500
agcgtgttca tcttcccccc cagcgacgag cagctgaaga gcggcaccgc cagcgtggtg    1560
tgcctgctga caacttctat ccccgggag gccaaggtgc agtggaaggt ggacaacgcc     1620
ctgcagagcg gcaacagcca ggagagcgtc accgagcagg acagcaagga ctccacctac    1680
agcctgagca gcaccctgac cctgagcaag gccgactacg agaagcacaa ggtgtacgcc    1740
tgcgaggtga cccaccaggg cctgtccagc cccgtgacca gagcttcaa caggggcgag     1800
tgctgactcg agtctagacc gcggccgctt ccctttagtg agggttaatg cttcgagcag    1860
acatgataag atacattgat gagtttggac aaaccacaac tagaatgcag tgaaaaaaat    1920
gctttatttg tgaaatttgt gatgctattg ctttatttgt aaccattata agctgcaata    1980
aacaagttaa caacaacaat tgcattcatt ttatgtttca ggttcagggg gagatgtggg    2040
aggttttta aagcaagtaa aacctctaca aatgtggtaa aatccgataa ggatcgatcc     2100
gggctggcgt aatagcgaag aggcccgcac cgatcgccct tcccaacagt tgcgcagcct    2160
gaatggcgaa tggacgcgcc ctgtagcggc gcattaagcg cggcgggtgt ggtggttacg    2220
cgcagcgtga ccgctacact tgccagcgcc ctagcgcccg ctcctttcgc tttcttccct    2280
tcctttctcg ccacgttcgc cggctttccc cgtcaagctc taaatcgggg gctcccttta    2340
gggttccgat ttagagcttt acggcacctc gaccgcaaaa aacttgattt gggtgatggt    2400
tcacgtagtg ggccatcgcc ctgatagacg gtttttcgcc ctttgacgtt ggagtccacg    2460
ttctttaata gtggactctt gttccaaact ggaacaacac tcaaccctat ctcggtctat    2520
tcttttgatt tataagggat tttgccgatt tcggcctatt ggttaaaaaa tgagctgatt    2580
taacaaatat ttaacgcgaa ttttaacaaa atattaacgt ttacaatttc gcctgatgcg    2640
gtattttctc cttacgcatc tgtgcggtat ttcacaccgc atacgcggat ctgcgcagca    2700
ccatggcctg aaataacctc tgaaagagga acttggttag gtaccttctg aggcggaaag    2760
aaccagctgt ggaatgtgtg tcagttaggg tgtggaaagt ccccaggctc cccagcaggc    2820
agaagtatgc aaagcatgca tctcaattag tcagcaacca ggtgtggaaa gtccccaggc    2880
tccccagcag gcagaagtat gcaaagcatg catctcaatt agtcagcaac catagtcccg    2940
cccctaactc cgcccatccc gcccctaact ccgcccagtt ccgcccattc tccgccccat    3000
ggctgactaa ttttttttat ttatgcagag gccgaggccg cctcggcctc tgagctattc    3060
cagaagtagt gaggaggctt ttttggaggc ctaggctttt gcaaaaagct tgattcttct    3120
gacacaacag tctcgaactt aaggctagag ccaccatgat tgaacaagat ggattgcacg    3180
caggttctcc ggccgcttgg gtggagaggc tattcggcta tgactgggca acagacaa     3240
tcggctgctc tgatgccgcc gtgttccggc tgtcagcgca ggggcgcccg gttctttttg    3300
tcaagaccga cctgtccggt gccctgaatg aactgcagga cgaggcagcg cggctatcgt    3360
ggctggccac gacgggcgtt ccttgcgcag ctgtgctcga cgttgtcact gaagcgggaa    3420
gggactggct gctattgggc gaagtgccgg ggcaggatct cctgtcatct caccttgctc    3480
ctgccgagaa agtatccatc atggctgatg caatgcggcg gctgcatacg cttgatccgg    3540
ctacctgccc attcgaccac caagcgaaac atcgcatcga gcgagcacgt actcggatgg    3600
aagccggtct tgtcgatcag gatgatctgg acgaagagca tcaggggctc gcgccagccg    3660
aactgttcgc caggctcaag gcgcgcatgc ccgacggcga ggatctcgtc gtgacccatg    3720
```

```
gcgatgcctg cttgccgaat atcatggtgg aaaatggccg ctttttctgga ttcatcgact    3780 gtggccggct gggtgtggcg gaccgctatc aggacatagc gttggctacc cgtgatattg    3840
ctgaagagct tggcggcgaa tgggctgacc gcttcctcgt gctttacggt atcgccgctc    3900
ccgattcgca gcgcatcgcc ttctatcgcc ttcttgacga gttcttctga gcgggactct    3960
ggggttcgaa atgaccgacc aagcgacgcc caacctgcca tcacgatggc cgcaataaaa    4020
tatctttatt ttcattacat ctgtgtgttg gttttttgtg tgaatcgata gcgataagga    4080
tccgcgtatg gtgcactctc agtacaatct gctctgatgc cgcatagtta agccagcccc    4140
gacacccgcc aacacccgct gacgcgcccct gacgggcttg tctgctcccg gcatccgctt    4200
acagacaagc tgtgaccgtc tccgggagct gcatgtgtca gaggttttca ccgtcatcac    4260
cgaaacgcgc gagacgaaag ggcctcgtga tacgcctatt tttataggtt aatgtcatga    4320
taataatggt ttcttagacg tcaggtggca cttttcgggg aaatgtgcgc ggaacccccta   4380 tttgtttatt tttctaaata cattcaaata tgtatccgct catgagacaa taaccctgat    4440
aaatgcttca ataatattga aaaggaaga gtatgagtat tcaacatttc cgtgtcgccc     4500
ttattccctt ttttgcggca ttttgccttc ctgttttttgc tcacccagaa acgctggtga   4560
aagtaaaaga tgctgaagat cagttgggtg cacgagtggg ttacatcgaa ctggatctca    4620
acagcggtaa gatccttgag agttttcgcc ccgaagaacg ttttccaatg atgagcactt    4680
ttaaagttct gctatgtggc gcggtattat cccgtattga cgccgggcaa gagcaactcg    4740
gtcgccgcat acactattct cagaatgact tggttgagta ctcaccagtc acagaaaagc    4800
atcttacgga tggcatgaca gtaagagaat tatgcagtgc tgccataacc atgagtgata    4860
acactgcggc caacttactt ctgacaacga tcggaggacc gaaggagcta accgcttttt    4920
tgcacaacat gggggatcat gtaactcgcc ttgatcgttg ggaaccggag ctgaatgaag    4980
ccataccaaa cgacgagcgt gacaccacga tgcctgtagc aatggcaaca acgttgcgca    5040
aactattaac tggcgaacta cttactctag cttcccggca acaattaata gactggatgg    5100
aggcggataa agttgcagga ccacttctgc gctcggccct tccggctggc tggtttattg    5160
ctgataaatc tggagccggt gagcgtgggt ctcgcggtat cattgcagca ctggggccag    5220
atggtaagcc ctcccgtatc gtagttatct acacgacggg gagtcaggca actatggatg    5280
aacgaaatag acagatcgct gagataggtg cctcactgat taagcattgg taactgtcag    5340
accaagttta ctcatatata ctttagattg atttaaaact tcatttttaa tttaaaagga    5400
tctaggtgaa gatcctttt gataatctca tgaccaaaat cccttaacgt gagttttcgt    5460
tccactgagc gtcagacccc gtagaaaaga tcaaaggatc ttcttgagat cctttttttc    5520
tgcgcgtaat ctgctgcttg caaacaaaaa aaccaccgct accagcggtg gtttgtttgc    5580
cggatcaaga gctaccaact cttttttccga aggtaactgg cttcagcaga gcgcagatac    5640
caaatactgt ccttctagtg tagccgtagt taggccacca cttcaagaac tctgtagcac    5700
cgcctacata cctcgctctg ctaatcctgt taccagtggc tgctgccagt ggcgataagt    5760
cgtgtcttac cgggttggac tcaagacgat agttaccgga taaggcgcag cggtcgggct    5820
gaacgggggg ttcgtgcaca cagcccagct tggagcgaac gacctacacc gaactgagat    5880
acctacagcg tgagctatga gaaagcgcca cgcttcccga agggagaaag gcggacaggt    5940
atccggtaag cggcagggtc ggaacaggag agcgcacgag ggagcttcca gggggaaacg    6000
cctggtatct ttatagtcct gtcgggtttc gccacctctg acttgagcgt cgatttttgt    6060
gatgctcgtc agggggggcgg agcctatgga aaaacgccag caacgcggcc ttttacggt    6120
```

```
<210> SEQ ID NO 29
<211> LENGTH: 400
<212> TYPE: DNA
<213> ORGANISM: Homo sapiens

<400> SEQUENCE: 29
ggtaccagcc accggtgtcc acagccaggt gcagctgcag cagtctggcg ccgagctggt      60
ccggcctggc gcctccgtga ccctgtcctg caaggcctcc ggctacacct tcaccgacta     120
cgagatgcac tgggtgaagc agaccccgt gcacggcctg gagtggatcg cgccgtggc      180
ccctgagacc ggcggcaccg cctacaacca gaagttcaag ggcaaggcca ccctgaccgc     240
cgccaagtcc tcctctaccg cctacatgga gctgcggtcc ctgacctccg aggactccgc     300
cgtgtactac tgcacctcca ccgtggtgcc tttcgcctac tggggccagg gcaccctggt     360
gaccgtgtcc gccgctagca ccaagggccc atccgagctc                            400

<210> SEQ ID NO 30
<211> LENGTH: 6682
<212> TYPE: DNA
<213> ORGANISM: Artificial Sequence
<220> FEATURE:
<223> OTHER INFORMATION: Synthetic Construct - IgG1H+VH optimised
      sequence

<400> SEQUENCE: 30
cttgaagacg aaagggcctc gtgatacgcc tatttttata ggttaatgtc atgataataa      60
tggtttctta gacgtcaggt ggcacttttc ggggaaatgt gcgcggaacc cctatttgtt     120
tatttttcta atacattca aatatgtatc cgctcatgag acaataaccc tgataaatgc      180
ttcaataata ttgaaaaagg aagagtatga gtattcaaca tttccgtgtc gcccttattc      240
ccttttttgc ggcattttgc cttcctgttt tgctcaccc agaaacgctg gtgaaagtaa      300
aagatgctga agatcagttg ggtgcacgag tgggttacat cgaactggat ctcaacagcg     360
gtaagatcct tgagagtttt cgccccgaag aacgttttcc aatgatgagc acttttaaag     420
ttctgctatg tggcgcggta ttatcccgtg ttgacgccgg gcaagagcaa ctcggtcgcc     480
gcatacacta ttctcagaat gacttggttg agtactcacc agtcacagaa aagcatctta     540
cggatggcat gacagtaaga gaattatgca gtgctgccat aaccatgagt gataacactg     600
cggccaactt acttctgaca acgatcggag gaccgaagga gctaaccgct ttttgcaca     660
acatggggga tcatgtaact cgccttgatc gttgggaacc ggagctgaat gaagccatac     720
caaacgacga gcgtgacacc acgatgcctg cagcaatggc aacaacgttg cgcaaactat      780
taactggcga actacttact ctagcttccc ggcaacaatt aatagactgg atggaggcgg      840
ataaagttgc aggaccactt ctgcgctcgg cccttccggc tggctggttt attgctgata      900
aatctggagc cggtgagcgt gggtctcgcg gtatcattgc agcactgggg ccagatggta      960
agccctcccg tatcgtagtt atctacacga cggggagtca ggcaactatg gatgaacgaa     1020
atagacagat cgctgagata ggtgcctcac tgattaagca ttggtaactg tcagaccaag     1080
tttactcata tatactttag attgatttaa aacttcattt ttaatttaaa aggatctagg     1140
tgaagatcct ttttgataat ctcatgacca aaatccctta acgtgagttt cgttccact     1200
gagcgtcaga ccccgtagaa aagatcaaag gatcttcttg agatcctttt tttctgcgcg     1260
taatctgctg cttgcaaaca aaaaaaccac cgctaccagc ggtggtttgt ttgccggatc     1320
```

```
aagagctacc aactcttttt ccgaaggtaa ctggcttcag cagagcgcag ataccaaata    1380
ctgtccttct agtgtagccg tagttaggcc accacttcaa gaactctgta gcaccgccta    1440
catacctcgc tctgctaatc ctgttaccag tggctgctgc cagtggcgat aagtcgtgtc    1500 ttaccggggtt ggactcaaga cgatagttac cggataaggc gcagcggtcg ggctgaacgg    1560
ggggttcgtg cacacagccc agcttggagc gaacgaccta caccgaactg agatacctac    1620
agcgtgagct atgagaaagc gccacgcttc ccgaagggag aaaggcggac aggtatccgg    1680
taagcggcag ggtcggaaca ggagagcgca cgagggagct tccagggggga aacgcctggt    1740 atctttatag tcctgtcggg tttcgccacc tctgacttga gcgtcgattt ttgtgatgct    1800
cgtcaggggg gcggagccta tggaaaaacg ccagcaacgc ggccttttta cggttcctgg    1860
ccttttgctg gccttttgct cacatgttct ttcctgcgtt atccctgat  tctgtggata    1920 accgtattac cgcctttgag tgagctgata ccgctcgccg cagccgaacg accgagcgca    1980
gcgagtcagt gagcgaggaa gcggaagagc gcctgatgcg gtattttctc cttacgcatc    2040
tgtgcggtat ttcacaccgc atatggtgca ctctcagtac aatctgctct gatgccgcat    2100
agttaagcca gtatacactc cgctatcgct acgtgactgg gtcatggctg cgccccgaca    2160
cccgccaaca cccgctgacg cgccctgacg ggcttgtctg ctcccggcat ccgcttacag    2220
acaagctgtg accgtctccg ggagctgcat gtgtcagagg ttttcaccgt catcaccgaa    2280
acgcgcgagg cagctgtgga atgtgtgtca gttagggtgt ggaaagtccc caggctcccc    2340
agcaggcaga agtatgcaaa gcatgcatct caattagtca gcaaccaggt gtggaaagtc    2400
cccaggctcc ccagcaggca agtatgcaa aagcatgcat ctcaattagt cagcaaccat    2460
agtcccgccc ctaactccgc ccatcccgcc cctaactccg cccagttccg cccattctcc    2520
gccccatggc tgactaattt tttttattta tgcagaggcc gaggccgcct cggcctctga    2580
gctattccag aagtagtgag gaggcttttt tggaggccta ggcttttgca aaaagcttat    2640
ggttcgacca ttgaactgca tcgtcgccgt gtcccaaaat atggggattg caagaacgg    2700 agacctaccc tggcctccgc tcaggaacga gttcaagtac ttccaaagaa tgaccacaac    2760
ctcttcagtg gaaggtaaac agaatctggt gattatgggt aggaaaacct ggttctccat    2820
tcctgagaag aatcgacctt taaaggacag aattaatata gttctcagta gagaactcaa    2880
agaaccacca cgaggagctc atttcttgc caaaagtttg gatgatgcct taagacttat    2940
tgaacaaccg gaattggcaa gtaaagtaga catggtttgg atagtcggag gcagttctgt    3000
ttaccaggaa gccatgaatc aaccaggcca ccttagactc tttgtgacaa ggatcatgca    3060
ggaatttgaa agtgacacgt ttttcccaga aattgatttg gggaaatata aacttctccc    3120
agaataccca ggcgtcctct ctgaggtcca ggaggaaaaa ggcatcaagt ataagtttga    3180
agtctacgag aagaaagact aactagtttg tgaaggaacc ttacttctgt ggtgtgacat    3240
aattggacaa actacctaca gagatttaaa gctctaaggt aaatataaaa ttttaagtg    3300 tataatgtgt taaactactg attctaattg tttgtgtatt ttagattcca acctatggaa    3360
ctgatgaatg ggagcagtgg tggaatgcct ttaatgagga aaacctgttt tgctcagaag    3420
aaatgccatc tagtgatgat gaggctactg ctgactctca acattctact cctccaaaaa    3480
agaagagaaa ggtagaagac cccaaggact tccttcaga  attgctaagt tttttgagtc    3540
atgctgtgtt tagtaataga actcttgctt gctttgctat ttacaccaca aaggaaaaag    3600
ctgcactgct atacaagaaa attatggaaa aatattctgt aacctttata agtaggcata    3660
```

```
acagttataa tcataacata ctgttttttc ttactccaca caggcataga gtgtctgcta    3720
ttaataacta tgctcaaaaa ttgtgtacct ttagcttttt aatttgtaaa ggggttaata    3780
aggaatattt gatgtatagt gccttgacta gagatcataa tcagccatac cacatttgta    3840
gaggttttac ttgcttttaaa aaacctccca cacctccccc tgaacctgaa acataaaatg    3900
aatgcaattg ttgttgttaa cttgtttatt gcagcttata atggttacaa ataaagcaat    3960
agcatcacaa atttcacaaa taaagcattt ttttcactgc attctagttg tggtttgtcc    4020
aaactcatca atgtatctta tcatgtctgg atcctgtgga atgtgtgtca gttagggtgt    4080
ggaaagtccc caggctcccc agcaggcaga agtatgcaaa gcatgcatct caattagtca    4140
gcaaccaggt gtggaaagtc cccaggctcc ccagcaggca gaagtatgca aagcatgcat    4200
ctcaattagt cagcaaccat agtcccgccc ctaactccgc ccatcccgcc cctaactccg    4260
cccagttccg cccattctcc gccccatggc tgactaattt ttttattta tgcagaggcc    4320 gaggccgcct cggcctctga gctattccag aagtagtgag gaggcttttt tggaggccta    4380
ggcttttgca aaaagctgcg gccgcgaatt caccatggac tggacctggc ggatcctgtt    4440
cctggtggcc gctgccaccg gtgtccacag ccaggtgcag ctgcagcagt ctggcgccga    4500
gctggtccgg cctggcgcct ccgtgaccct gtcctgcaag gcctccggct acaccttcac    4560
cgactacgag atgcactggg tgaagcagac ccctgtgcac ggcctggagt ggatcggcgc    4620
cgtggcccct gagaccggcg gcaccgccta aaccagaag ttcaagggca aggccaccct    4680
gaccgccgcc aagtcctcct ctaccgccta catggagctg cggtccctga cctccgagga    4740
ctccgccgtg tactactgca cctccaccgt ggtgcctttc gcctactggg gccagggcac    4800
cctggtgacc gtgtccgccg ctagcaccaa gggccccagc gtgttccccc tggcgcccag    4860
cagcaagagc accagcggcg gcacagccgc cctgggctgc ctggtgaagg actacttccc    4920
cgagcccgtg accgtgagct ggaacagcgg agccctgacc tccggcgtgc acaccttccc    4980
cgccgtgctg cagagcagcg gcctgtacag cctgagcagc gtggtgaccg tgcccagcag    5040
cagcctgggc acccagacct acatctgcaa cgtgaaccac aagcccagca caccaaggt    5100 ggacaagaag gtggagccca gagctgcga caagacccac acctgccccc ctgcccagc    5160 cccagagctg ctgggcggac cctccgtgtt cctgttcccc cccaagccca aggacaccct    5220
gatgatcagc aggacccccg aggtgacctg cgtggtggtg gacgtgagcc acgaggaccc    5280
agaggtgaag ttcaactggt acgtggacgg cgtggaggtg cacaacgcca agaccaagcc    5340
cagagaggag cagtacaaca gcacctacag ggtggtgtcc gtgctgaccg tgctgcacca    5400
ggactggctg aacggcaagg aatacaagtg caaggtctcc aacaaggccc tgccagcccc    5460
catcgaaaag accatcagca aggccaaggg ccagccacgg gagccccagg tgtacccct    5520 gccccctcc cggacgagc tgaccaagaa ccaggtgtcc ctgacctgtc tggtgaaggg    5580
cttctacccc agcgacatcg ccgtggagtg ggagagcaac ggccagcccg agaacaacta    5640
caagaccacc cccccagtgc tggacagcga cggcagcttc ttcctgtaca gcaagctgac    5700
cgtggacaag agcaggtggc agcagggcaa cgtgttcagc tgcagcgtga tgcacgaggc    5760
cctgcacaac cactacaccc agaagagcct gagcctgtcc cccggcaagt gactcgagtc    5820
tagaccgcgg tttgtgaagg aaccttactt ctgtggtgtg ataattgg acaaactacc    5880 tacagagatt taaagctcta aggtaaatat aaaattttta agtgtataat gtgttaaact    5940
actgattcta attgttgtg tatttttagat tccaacctat ggaactgatg aatgggagca    6000
gtggtggaat gcctttaatg aggaaaacct gttttgctca gaagaaatgc catctagtga    6060
```

| | |
|---|---|
| tgatgaggct actgctgact ctcaacattc tactcctcca aaaaagaaga gaaaggtaga | 6120 |
| agaccccaag gactttcctt cagaattgct aagttttttg agtcatgctg tgtttagtaa | 6180 |
| tagaactctt gcttgctttg ctatttacac cacaaaggaa aaagctgcac tgctatacaa | 6240 |
| gaaaattatg gaaaaatatt ctgtaacctt tataagtagg cataacagtt ataatcataa | 6300 |
| catactgttt tttcttactc cacacaggca tagagtgtct gctattaata actatgctca | 6360 |
| aaaattgtgt acctttagct ttttaatttg taaaggggtt aataaggaat atttgatgta | 6420 |
| tagtgccttg actagagatc ataatcagcc ataccacatt tgtagaggtt ttacttgctt | 6480 |
| taaaaaacct cccacacctc ccctgaacc tgaaacataa aatgaatgca attgttgttg | 6540 |
| ttaacttgtt tattgcagct tataatggtt acaaataaag caatagcatc acaaatttca | 6600 |
| caaataaagc attttttca ctgcattcta gttgtggttt gtccaaactc atcaatgtat | 6660 |
| cttatcatgt ctggatcgaa tt | 6682 |

<210> SEQ ID NO 31
<211> LENGTH: 1441
<212> TYPE: DNA
<213> ORGANISM: Artificial Sequence
<220> FEATURE:
<223> OTHER INFORMATION: Synthetic Construct - IgG4H+VH optimised sequence

<400> SEQUENCE: 31

| | |
|---|---|
| ggtacctggc ggccgcgaat tcaccatgga ttggacctgg cggatcctgt tcctggtggc | 60 |
| tgctgccacc ggtgtccaca gccaggtgca gctgcagcag tctggcgccg agctggtccg | 120 |
| gcctggcgcc tccgtgaccc tgtcctgcaa ggcctccggc tacaccttca ccgactacga | 180 |
| gatgcactgg gtgaagcaga cccctgtgca cggcctggag tggatcggcg ccgtggcccc | 240 |
| tgagaccggc ggcaccgcct acaaccagaa gttcaagggc aaggccaccc tgaccgccgc | 300 |
| caagtcctcc tctaccgcct acatggagct gcggtccctg acctccgagg actccgccgt | 360 |
| gtactactgc acctccaccg tggtgccttt cgcctactgg ggccagggca cctggtgac | 420 |
| cgtgtccgcc gctagcacca agggcccatc cgtgttccct ctggcccctt gctcccggtc | 480 |
| cacctccgag tccaccgccg ctctgggctg cctggtgaag gactacttcc ctgagcctgt | 540 |
| gaccgtgagc tggaactccg gcgccctgac cagcggcgtg cacaccttcc ctgccgtgct | 600 |
| gcagtcctcc ggcctgtact ccctgtcctc cgtggtgaca gtgccttcct cctccctggg | 660 |
| caccaagacc tacacctgca acgtggacca caagccttcc aacaccaagg tggacaagcg | 720 |
| ggtggagtcc aagtacggcc ctccttgccc ttcctgccct gcccctgagt tcctgggcgg | 780 |
| accttccgtg ttcctgttcc ctcctaagcc taaggacacc ctgatgatct cccggacccc | 840 |
| tgaggtgacc tgcgtggtgg tggacgtgtc ccaggaagat cctgaggtcc agttcaattg | 900 |
| gtacgtggac ggcgtggaag tccacaacgc caagaccaag cctcgggagg aacagttcaa | 960 |
| ctccacctac cgggtggtgt ccgtgctgac cgtgctgcac caggactggc tgaacggcaa | 1020 |
| ggaatacaag tgcaaggtct ccaacaaggg cctgcccctc ccatcgaga aaccatctc | 1080 |
| caaggccaag ggccagcctc gcgagcctca ggtgtacacc ctgcctccta gccaagaaga | 1140 |
| gatgaccaag aaccaggtgt ccctgacatg tctggtgaag ggcttctacc cttccgacat | 1200 |
| cgccgtggag tgggagtcca acggccagcc tgagaacaac tacaagacca ccctcctgt | 1260 |
| gctggactcc gacggctcct tcttcctgta ctccaggctg accgtggaca agtcccggtg | 1320 |
| gcaggaaggc aacgtctttt cctgctccgt gatgcacgag gccctgcaca accactacac | 1380 |

```
ccagaagtcc ctgtccctga gcctgggcaa gtgactcgag tctagaccgc ggccggagct    1440
c                                                                    1441
```

<210> SEQ ID NO 32
<211> LENGTH: 22
<212> TYPE: PRT
<213> ORGANISM: Homo sapiens

<400> SEQUENCE: 32

```
Pro Pro Met Thr Ile Tyr Thr Glu Gln Asp Leu Tyr Asn His Val Val
1               5                   10                  15

Pro Lys Pro His Asn Lys
            20
```

<210> SEQ ID NO 33
<211> LENGTH: 10
<212> TYPE: PRT
<213> ORGANISM: Homo sapiens

<400> SEQUENCE: 33

```
Gly Tyr Thr Pro Thr Asp Tyr Glu Met His
1               5                   10
```

<210> SEQ ID NO 34
<211> LENGTH: 17
<212> TYPE: PRT
<213> ORGANISM: Homo sapiens

<400> SEQUENCE: 34

```
Ala Val Ala Pro Glu Thr Gly Gly Thr Ala Tyr Trp Gln Lys Phe Lys
1               5                   10                  15

Gly
```

<210> SEQ ID NO 35
<211> LENGTH: 7
<212> TYPE: PRT
<213> ORGANISM: Homo sapiens

<400> SEQUENCE: 35

```
Thr Val Val Pro Phe Ala Tyr
1               5
```

<210> SEQ ID NO 36
<211> LENGTH: 10
<212> TYPE: PRT
<213> ORGANISM: Homo sapiens

<400> SEQUENCE: 36

```
Ser Ala Ser Ser Ser Val Ser Tyr Met Tyr
1               5                   10
```

<210> SEQ ID NO 37
<211> LENGTH: 7
<212> TYPE: PRT
<213> ORGANISM: Homo sapiens

<400> SEQUENCE: 37

```
Arg Thr Ser Asn Leu Ala Ser
1               5
```

<210> SEQ ID NO 38
<211> LENGTH: 9

<212> TYPE: PRT
<213> ORGANISM: Homo sapiens

<400> SEQUENCE: 38

Gln Gln Tyr Gln Ser Leu Pro Leu Thr
1               5

<210> SEQ ID NO 39
<211> LENGTH: 116
<212> TYPE: PRT
<213> ORGANISM: Homo sapiens

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Val Ala Pro Glu Thr Gly Gly Thr Ala Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Thr Val Val Pro Phe Ala Tyr Trp Gly Gln Gly Thr Leu Val
            100                 105                 110

Thr Val Ser Ser
        115

<210> SEQ ID NO 40
<211> LENGTH: 116
<212> TYPE: PRT
<213> ORGANISM: Homo sapiens

<400> SEQUENCE: 40

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Ile
        35                  40                  45

Gly Ala Val Ala Pro Glu Thr Gly Gly Thr Ala Tyr Asn Gln Lys Phe
    50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Thr Val Val Pro Phe Ala Tyr Trp Gly Gln Gly Thr Leu Val
            100                 105                 110

Thr Val Ser Ser
        115

<210> SEQ ID NO 41
<211> LENGTH: 116
<212> TYPE: PRT
<213> ORGANISM: Homo sapiens

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Ile
            35                  40                  45

Gly Ala Val Ala Pro Glu Thr Gly Thr Ala Tyr Asn Gln Lys Phe
    50                  55                  60

Lys Gly Arg Ala Thr Leu Thr Ala Ala Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Thr Val Val Pro Phe Ala Tyr Trp Gly Gln Gly Thr Leu Val
                100                 105                 110

Thr Val Ser Ser
            115

<210> SEQ ID NO 42
<211> LENGTH: 116
<212> TYPE: PRT
<213> ORGANISM: Homo sapiens

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Ile
            35                  40                  45

Gly Ala Val Ala Pro Glu Thr Gly Thr Ala Tyr Asn Gln Lys Phe
    50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Thr Val Val Pro Phe Ala Tyr Trp Gly Gln Gly Thr Leu Val
                100                 105                 110

Thr Val Ser Ser
            115

<210> SEQ ID NO 43
<211> LENGTH: 116
<212> TYPE: PRT
<213> ORGANISM: Homo sapiens

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Glu Met His Trp Val Lys Gln Ala Pro Gly Gln Gly Leu Glu Trp Ile
            35                  40                  45

Gly Ala Val Ala Pro Glu Thr Gly Thr Ala Tyr Asn Gln Lys Phe
    50                  55                  60

Lys Gly Arg Ala Thr Ile Thr Ala Asp Lys Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Ser Thr Val Val Pro Phe Ala Tyr Trp Gly Gln Gly Thr Leu Val
            100                 105                 110

Thr Val Ser Ser
        115

<210> SEQ ID NO 44
<211> LENGTH: 116
<212> TYPE: PRT
<213> ORGANISM: Homo sapiens

<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Ile
        35                  40                  45

Gly Ala Val Ala Pro Glu Thr Gly Gly Thr Ala Tyr Asn Gln Lys Phe
    50                  55                  60

Lys Gly Lys Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Thr Val Val Pro Phe Ala Tyr Trp Gly Gln Gly Thr Leu Val
            100                 105                 110

Thr Val Ser Ser
        115

<210> SEQ ID NO 45
<211> LENGTH: 116
<212> TYPE: PRT
<213> ORGANISM: Homo sapiens

<400> SEQUENCE: 45

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Ile
        35                  40                  45

Gly Ala Val Ala Pro Glu Thr Gly Gly Thr Ala Tyr Asn Gln Lys Phe
    50                  55                  60

Lys Gly Arg Ala Thr Ile Thr Ala Asp Lys Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Ser Thr Val Val Pro Phe Ala Tyr Trp Gly Gln Gly Thr Leu Val
            100                 105                 110

Thr Val Ser Ser
        115

<210> SEQ ID NO 46
<211> LENGTH: 106
<212> TYPE: PRT
<213> ORGANISM: Homo sapiens
```

```
<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Tyr Trp Tyr Gln Gln Lys Pro Gly Lys Ala Pro Lys Leu Leu Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Tyr Gln Ser Leu Pro Leu Thr
                85                  90                  95

Phe Gly Gly Gly Thr Lys Val Glu Ile Lys
            100                 105

<210> SEQ ID NO 47
<211> LENGTH: 106
<212> TYPE: PRT
<213> ORGANISM: Homo sapiens

<400> SEQUENCE: 47

Gln Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Tyr Trp Tyr Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Tyr Gln Ser Leu Pro Leu Thr
                85                  90                  95

Phe Gly Gly Gly Thr Lys Val Glu Ile Lys
            100                 105

<210> SEQ ID NO 48
<211> LENGTH: 106
<212> TYPE: PRT
<213> ORGANISM: Homo sapiens

<400> SEQUENCE: 48

Gln Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Tyr Trp Tyr Gln Gln Lys Pro Gly Lys Ala Pro Lys Ala Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Tyr Gln Ser Leu Pro Leu Thr
                85                  90                  95
```

-continued

Phe Gly Gly Gly Thr Lys Val Glu Ile Lys
            100                 105

<210> SEQ ID NO 49
<211> LENGTH: 5
<212> TYPE: PRT
<213> ORGANISM: Homo sapiens

<400> SEQUENCE: 49

Asp Tyr Glu Met His
1               5

<210> SEQ ID NO 50
<211> LENGTH: 17
<212> TYPE: PRT
<213> ORGANISM: Homo sapiens

<400> SEQUENCE: 50

Ala Val Ala Pro Glu Thr Gly Gly Thr Ala Tyr Asn Gln Lys Phe Lys
1               5                   10                  15

Gly

<210> SEQ ID NO 51
<211> LENGTH: 7
<212> TYPE: PRT
<213> ORGANISM: Homo sapiens

<400> SEQUENCE: 51

Thr Val Val Pro Phe Ala Tyr
1               5

<210> SEQ ID NO 52
<211> LENGTH: 10
<212> TYPE: PRT
<213> ORGANISM: Homo sapiens

<400> SEQUENCE: 52

Ser Ala Ser Ser Ser Val Ser Tyr Met Tyr
1               5                   10

<210> SEQ ID NO 53
<211> LENGTH: 7
<212> TYPE: PRT
<213> ORGANISM: Homo sapiens

<400> SEQUENCE: 53

Arg Thr Ser Asn Leu Ala Ser
1               5

<210> SEQ ID NO 54
<211> LENGTH: 9
<212> TYPE: PRT
<213> ORGANISM: Homo sapiens

<400> SEQUENCE: 54

Gln Gln Tyr Gln Ser Leu Pro Leu Thr
1               5

<210> SEQ ID NO 55
<211> LENGTH: 1386
<212> TYPE: DNA
<213> ORGANISM: Homo sapiens

<400> SEQUENCE: 55

| | | | | | | |
|---|---|---|---|---|---|---|
| atggacttcg | ggctcagctg | ggttttcctt | gccctcattt | taaaaggtgt | ccagtgtcag | 60 |
| gtgcagctgg | tgcagtctgg | ggctgaggtg | aagaagcctg | gtcctcggt | gaaggtctcc | 120 |
| tgcaaggctt | ctggatacac | cttcaccgac | tacgagatgc | actgggtgcg | acaggcccct | 180 |
| ggacaagggc | ttgagtggat | ggagctgtg | gcccctgaaa | ctggtggtac | tgcctacaat | 240 |
| cagaagttca | agggcagagc | cacgattacc | gcggacaaat | ccacgagcac | agcctacatg | 300 |
| gagctgagca | gcctgagatc | tgaggacacg | gccgtgtatt | actgtacctc | caccgtggtg | 360 |
| cctttcgcct | actggggcca | aggaaccctg | gtcaccgtct | cctcagcttc | caccaagggc | 420 |
| ccatccgtct | tccccctggc | gccctgctcc | aggagcacct | ccgagagcac | agccgccctg | 480 |
| ggctgcctgg | tcaaggacta | cttccccgaa | ccggtgacgg | tgtcgtggaa | ctcaggcgcc | 540 |
| ctgaccagcg | gcgtgcacac | cttcccggct | gtcctacagt | cctcaggact | ctactccctc | 600 |
| agcagcgtgg | tgaccgtgcc | ctccagcagc | ttgggcacga | agacctacac | ctgcaacgta | 660 |
| gatcacaagc | ccagcaacac | caaggtggac | aagagagttg | agtccaaata | tggtccccca | 720 |
| tgcccaccat | gcccagcacc | tgagttcctg | ggggaccat | cagtcttcct | gttccccca | 780 |
| aaacccaagg | acactctcat | gatctcccgg | acccctgagg | tcacgtgcgt | ggtggtggac | 840 |
| gtgagccagg | aagaccccga | ggtccagttc | aactggtacg | tggatggcgt | ggaggtgcat | 900 |
| aatgccaaga | caaagccgcg | ggaggagcag | ttcaacagca | cgtaccgtgt | ggtcagcgtc | 960 |
| ctcaccgtcc | tgcaccagga | ctggctgaac | ggcaaggagt | acaagtgcaa | ggtctccaac | 1020 |
| aaaggcctcc | cgtcctccat | cgagaaaacc | atctccaaag | ccaaagggca | gccccgagag | 1080 |
| ccacaggtgt | acaccctgcc | cccatcccag | gaggagatga | ccaagaacca | ggtcagcctg | 1140 |
| acctgcctgg | tcaaaggctt | ctaccccagc | gacatcgccg | tggagtggga | gagcaatggg | 1200 |
| cagccggaga | acaactacaa | gaccacgcct | cccgtgctgg | actccgacgg | ctccttcttc | 1260 |
| ctctacagca | ggctaaccgt | ggacaagagc | aggtggcagg | aggggaatgt | cttctcatgc | 1320 |
| tccgtgatgc | atgaggctct | gcacaaccac | tacacacaga | agagcctctc | cctgtctctg | 1380 |
| ggtaaa | | | | | | 1386 |

<210> SEQ ID NO 56
<211> LENGTH: 462
<212> TYPE: PRT
<213> ORGANISM: Homo sapiens

<400> SEQUENCE: 56

Met Asp Phe Gly Leu Ser Trp Val Phe Leu Ala Leu Ile Leu Lys Gly
1               5                   10                  15

Val Gln Cys Gln Val Gln Leu Val Gln Ser Gly Ala Glu Val Lys Lys
                20                  25                  30

Pro Gly Ser Ser Val Lys Val Ser Cys Lys Ala Ser Gly Tyr Thr Phe
            35                  40                  45

Thr Asp Tyr Glu Met His Trp Val Arg Gln Ala Pro Gly Gln Gly Leu
        50                  55                  60

Glu Trp Ile Gly Ala Val Ala Pro Glu Thr Gly Gly Thr Ala Tyr Asn
65                  70                  75                  80

Gln Lys Phe Lys Gly Arg Ala Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Thr Ser Thr Val Val Pro Phe Ala Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Lys Thr Tyr Thr Cys Asn Val Asp His Lys Pro
    210                 215                 220

Ser Asn Thr Lys Val Asp Lys Arg Val Glu Ser Lys Tyr Gly Pro Pro
225                 230                 235                 240

Cys Pro Pro Cys Pro Ala Pro Glu Phe Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser Gln Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Gly Leu Pro Ser Ser Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Gln Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Arg Leu Thr Val Asp Lys Ser Arg Trp
            420                 425                 430

Gln Glu Gly Asn Val Phe Ser Cys Ser Val Met His Glu Ala Leu His
        435                 440                 445

Asn His Tyr Thr Gln Lys Ser Leu Ser Leu Ser Leu Gly Lys
    450                 455                 460

<210> SEQ ID NO 57
<211> LENGTH: 817
<212> TYPE: DNA
<213> ORGANISM: Homo sapiens

<400> SEQUENCE: 57
atggacttcg ggctcagctg ggttttcctt gccctcattt taaaggtgt ccagtgtcaa      60 atccagctca cccagtctcc atcctccctg tctgcatctg taggagacag agtcaccatc    120
acttgctccg cctcctcctc cgtgtcctac atgtactggt atcagcagaa accagggaaa    180
gcccctaagg cctggatcta tgcacatcc aacttggcta gtggggtccc atcaaggttc    240

```
agtggcagtg atctgggac agattacact ctcaccatca gcagtctgca acctgaagat      300
tttgcaactt actactgtca acagtatcag agtctgcctc tcactttcgg cggagggacc      360
aaggtggaga tcaaacgtaa gtcgacttct agattgtcga ctgtccctaa catgccctgt      420
gattatccgc aaacaacaca cccaagggca aactttgtt acttaaacac catcctgttt       480
gcttctttcc tcaggaactg tggctgcacc atctgtcttc atcttcccgc catctgatga      540
gcagttgaaa tctggaactg cctctgttgt gtgcctgctg aataacttct atcccagaga      600
ggccaaagta cagtggaagg tggataacgc cctccaatcg ggtaactccc aggagagtgt      660
cacagagcag acagcaagg acagcaccta cagcctcagc agcaccctga cgctgagcaa       720
agcagactac gagaaacaca agtctacgc ctgcgaagtc acccatcagg gcctgagctc       780
gcccgtcaca aagagcttca cagggga gtgttag                                  817

<210> SEQ ID NO 58
<211> LENGTH: 118
<212> TYPE: DNA
<213> ORGANISM: Homo sapiens

<400> SEQUENCE: 58
gtaagtcgac ttctagattg tcgactgtcc ctaacatgcc ctgtgattat ccgcaaacaa       60
cacacccaag ggcagaactt tgttacttaa acaccatcct gtttgcttct ttcctcag       118

<210> SEQ ID NO 59
<211> LENGTH: 696
<212> TYPE: DNA
<213> ORGANISM: Homo sapiens

<400> SEQUENCE: 59
atggacttcg ggctcagctg ggttttcctt gccctcattt taaaggtgt ccagtgtcaa        60 atccagctca cccagtctcc atcctccctg tctgcatctg taggagacag agtcaccatc      120
acttgctccg cctcctcctc cgtgtcctac atgtactggt atcagcagaa accagggaaa      180
gcccctaagg cctggatcta tgcacatcc aacttggcta gtgggtcc atcaaggttc         240 agtggcagtg gatctgggac agattacact ctcaccatca gcagtctgca acctgaagat      300
tttgcaactt actactgtca acagtatcag agtctgcctc tcactttcgg cggagggacc      360
aaggtggaga tcaaacgaac tgtggctgca ccatctgtct tcatcttccc gccatctgat      420
gagcagttga atctggaac tgcctctgtt gtgtgcctgc tgaataactt ctatcccaga       480
gaggccaaag tacagtggaa ggtggataac gccctccaat cgggtaactc ccaggagagt      540
gtcacagagc aggacagcaa ggacagcacc tacagcctca gcagcaccct gacgctgagc      600
aaagcagact acgagaaaca caagtctacg cctgcgaag tcacccatca gggcctgagc       660
tcgcccgtca caaagagctt caacagggga gagtgt                                696

<210> SEQ ID NO 60
<211> LENGTH: 232
<212> TYPE: PRT
<213> ORGANISM: Homo sapiens

<400> SEQUENCE: 60

Met Asp Phe Gly Leu Ser Trp Val Phe Leu Ala Leu Ile Leu Lys Gly
1               5                   10                  15

Val Gln Cys Gln Ile Gln Leu Thr Gln Ser Pro Ser Ser Leu Ser Ala
            20                  25                  30
```

Ser Val Gly Asp Arg Val Thr Ile Thr Cys Ser Ala Ser Ser Ser Val
            35                  40                  45

Ser Tyr Met Tyr Trp Tyr Gln Gln Lys Pro Gly Lys Ala Pro Lys Ala
 50                  55                  60

Trp Ile Tyr Arg Thr Ser Asn Leu Ala Ser Gly Val Pro Ser Arg Phe
 65                  70                  75                  80

Ser Gly Ser Gly Ser Gly Thr Asp Tyr Thr Leu Thr Ile Ser Ser Leu
            85                  90                  95

Gln Pro Glu Asp Phe Ala Thr Tyr Tyr Cys Gln Gln Tyr Gln Ser Leu
            100                 105                 110

Pro Leu Thr Phe Gly Gly Gly Thr Lys Val Glu Ile Lys Arg Thr Val
            115                 120                 125

Ala Ala Pro Ser Val Phe Ile Phe Pro Pro Ser Asp Glu Gln Leu Lys
 130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
            165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
            195                 200                 205

Val Tyr Ala Cys Glu Val Thr His Gln Gly Leu Ser Ser Pro Val Thr
 210                 215                 220

Lys Ser Phe Asn Arg Gly Glu Cys
225                 230

<210> SEQ ID NO 61
<211> LENGTH: 443
<212> TYPE: PRT
<213> ORGANISM: Artificial Sequence
<220> FEATURE:
<223> OTHER INFORMATION: Synthetic Construct - Chimeric GNbAC1 IgG4

<400> SEQUENCE: 61

Gln Val Gln Leu Gln Gln Ser Gly Ala Glu Leu Val Arg Pro Gly Ala
 1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
            35                  40                  45

Gly Ala Val Ala Pro Glu Thr Gly Gly Thr Ala Tyr Asn Gln Lys Phe
 50                  55                  60

Lys Gly Lys Ala Thr Leu Thr Ala Ala Lys Ser Ser Ser Thr Ala Tyr
 65                  70                  75                  80

Met Glu Leu Arg Ser Leu Thr Ser Glu Asp Ser Ala Val Tyr Tyr Cys
            85                  90                  95

Thr Ser Thr Val Val Pro Phe Ala Tyr Trp Gly Gln Gly Thr Leu Val
            100                 105                 110

Thr Val Ser Ala Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
 130                 135                 140

Val Lys Asp Tyr Phe Pro Glu Pro Val Thr Val Ser Trp Asn Ser Gly
145                 150                 155                 160

```
Ala Leu Thr Ser Gly Val His Thr Phe Pro Ala Val Leu Gln Ser Ser
            165                 170                 175

Gly Leu Tyr Ser Leu Ser Ser Val Thr Val Pro Ser Ser Ser Leu
        180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Ser
210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
                260                 265                 270

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440

<210> SEQ ID NO 62
<211> LENGTH: 213
<212> TYPE: PRT
<213> ORGANISM: Artificial Sequence
<220> FEATURE:
<223> OTHER INFORMATION: Synthetic Construct - Chimeric GNbAC1 Light
      Chain

<400> SEQUENCE: 62

Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Ser Val Ser Tyr Met
                20                  25                  30

Tyr Trp Tyr Gln Gln Lys Pro Gly Ser Ser Pro Lys Ala Trp Ile Tyr
            35                  40                  45

Arg Thr Ser Asn Leu Ala Ser Gly Val Pro Gly Arg Phe Ser Gly Ser
        50                  55                  60

Gly Ser Gly Thr Ser Tyr Ser Leu Thr Ile Ser Ser Met Glu Ala Glu
65                  70                  75                  80
```

```
Asp Ala Ala Thr Tyr Tyr Cys Gln Gln Tyr Gln Ser Leu Pro Leu Thr
                85                  90                  95

Phe Gly Ser Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 63
<211> LENGTH: 443
<212> TYPE: PRT
<213> ORGANISM: Homo sapiens

<400> SEQUENCE: 63

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Ile
        35                  40                  45

Gly Ala Val Ala Pro Glu Thr Gly Gly Thr Ala Tyr Asn Gln Lys Phe
    50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Thr Val Val Pro Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
```

-continued

```
                225                 230                 235                 240
Pro Lys Pro Lys Asp Thr Leu Met Ile Ser Arg Thr Pro Glu Val Thr
                245                 250                 255

Cys Val Val Asp Val Ser Gln Glu Asp Pro Glu Val Gln Phe Asn
                260                 265                 270

Trp Tyr Val Asp Gly Val Glu Val His Asn Ala Lys Thr Lys Pro Arg
                275                 280                 285

Glu Glu Gln Phe Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
                340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
        370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
                420                 425                 430

Thr Gln Lys Ser Leu Ser Leu Ser Leu Gly Lys
        435                 440

<210> SEQ ID NO 64
<211> LENGTH: 213
<212> TYPE: PRT
<213> ORGANISM: Homo sapiens

<400> SEQUENCE: 64

Gln Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
                20                  25                  30

Tyr Trp Tyr Gln Gln Lys Pro Gly Lys Ala Pro Lys Ala Trp Ile Tyr
            35                  40                  45

Arg Thr Ser Asn Leu Ala Ser Gly Val Pro Ser Arg Phe Ser Gly Ser
        50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Tyr Gln Ser Leu Pro Leu Thr
                85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160
```

```
Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
        180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 65
<211> LENGTH: 702
<212> TYPE: DNA
<213> ORGANISM: Homo sapiens

<400> SEQUENCE: 65
atggccctgc agacccaggt gttcatctcc ctgctgctgt ggatatccgg agcctacggc     60
cagatccagc tgacccagtc cccttcctcc ctgtctgcct ccgtgggcga cagagtgacc    120
atcacctgtt ccgcctcttc cagcgtgtcc tacatgtact ggtatcagca gaagcctggc    180
aaggccccta aggcctggat ctaccggacc tccaacctgg cctccggcgt gccttccagg    240
ttctccggct ccggctctgg caccgactac accctgacca tctccagcct gcagcctgag    300
gacttcgcca cctactactg ccagcagtac cagtccctgc ctctgacctt cggcggaggc    360
accaaggtgg agatcaagcg tacggtggcg gcgccatctg tgttcatctt cccccttcc    420 gacgagcagc tgaagtccgg caccgcctct gtggtgtgcc tgctgaacaa cttctaccct    480
cgggaggcca aggtgcagtg gaaggtggac aacgccctgc agtccggcaa ctcccaggaa    540
tccgtcaccg agcaggactc caaggactct acctactccc tgtcctccac cctgaccctg    600
tccaaggcca actacgagaa gcacaaggtg tacgcctgcg aagtgaccca ccagggcctg    660
agttctcccg tgaccaagtc cttcaaccgg ggcgagtgct ga                       702

<210> SEQ ID NO 66
<211> LENGTH: 1389
<212> TYPE: DNA
<213> ORGANISM: Homo sapiens

<400> SEQUENCE: 66
atggactgga cctggcggat cctgtttctg gtggccgctg ccaccggtgt gcactcccag     60
gtgcagctgg tgcagtctgg cgccgaagtg aagaaacctg gctcctccgt gaaggtgtcc    120
tgcaaggcct ccggctacac cttcaccgac tacgagatgc actgggtgcg ccaggctcca    180
ggacagggcc tggaatggat cggcgccgtg gctcctgaaa ccggcggcac cgcctacaac    240
cagaagttca gggcagggc caccatcacc gccgacaagt ccacctctac cgcctacatg    300
gaactgtcct ccctgcggtc tgaggacacc gccgtgtact actgcacctc caccgtggtg    360
cctttcgctt actggggcca gggcaccctg gtgaccgtgt cctccgctag caccaagggc    420
ccttccgtgt tccctctggc cccttgctcc cggtccacct tgagtctac gccgctctg    480 ggctgcctgg tgaaggacta cttccctgag cctgtgacag tgtcttggaa ctctggcgcc    540
ctgacctctg gcgtgcacac cttccctgcc gtgctgcagt cctccggcct gtactccctg    600
tcctccgtgg tgacagtgcc ttcctcctcc ctgggcacca gacctacac ctgtaacgtg    660 gaccacaagc cttccaacac caaggtggac aagcgggtgg agtccaagta cggccctcct    720
tgccctccat gccctgcccc tgagttcctg ggaggcccct ccgtgttcct gttccctcct    780
aagcctaagg acaccctgat gatctcccgg acccctgaag tgacctgcgt ggtggtggac    840
```

```
gtgtcccagg aagatcctga ggtccagttc aattggtacg tggacggcgt ggaggtgcac    900
aacgccaaga ccaagcctag agaggaacag ttcaactcca cctaccgggt ggtgtccgtg    960
ctgaccgtgc tgcaccagga ctggctgaac ggcaaagaat acaagtgcaa ggtgtccaac   1020
aagggcctgc cctcctccat cgaaaagacc atctccaagg ccaagggcca gcctcgggaa   1080
cctcaggtgt acaccctgcc tccctctcag gaagagatga ccaagaacca ggtgtccctg   1140
acctgtctgg tgaagggctt ctacccttcc gatatcgccg tggagtggga gtctaacggc   1200
cagcctgaga acaactacaa gaccacccct cctgtgctgg actccgacgg ctccttcttc   1260
ctgtactcca ggctgaccgt ggacaagtcc cggtggcagg aaggcaacgt cttttcctgc   1320
tccgtgatgc acgaggccct gcacaaccac tacacccaga gtccctgtc  cctgtctctg   1380 ggcaagtga                                                           1389
```